(12) United States Patent
Miyazaki et al.

(10) Patent No.: US 12,240,817 B2
(45) Date of Patent: Mar. 4, 2025

(54) HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

(71) Applicant: Samsung Electronics Co., Ltd., Suwon-si (KR)

(72) Inventors: Eigo Miyazaki, Kanagawa (JP); Satoshi Inayama, Kanagawa (JP); Atsushi Imamura, Kanagawa (JP); Hosuk Kang, Suwon-si (KR); Sangmo Kim, Hwaseong-si (KR); Mitsunori Ito, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 793 days.

(21) Appl. No.: 17/472,807

(22) Filed: Sep. 13, 2021

(65) Prior Publication Data

US 2022/0204453 A1    Jun. 30, 2022

(30) Foreign Application Priority Data

Dec. 25, 2020  (JP) .................................. 2020-216562
Apr. 26, 2021  (KR) ........................ 10-2021-0053758

(51) Int. Cl.
*H01L 51/50* (2006.01)
*C07D 221/18* (2006.01)
(Continued)

(52) U.S. Cl.
CPC ....... *C07D 221/18* (2013.01); *H10K 85/6572* (2023.02); *H10K 50/11* (2023.02);
(Continued)

(58) Field of Classification Search
None
See application file for complete search history.

(56) References Cited

U.S. PATENT DOCUMENTS 5,227,252 A    7/1993   Murayama et al.
8,872,422 B2  10/2014   Qiu et al.
(Continued)

FOREIGN PATENT DOCUMENTS

CN    107501311 A    12/2017
CN    109456326 A     3/2019
(Continued)

OTHER PUBLICATIONS

David Hall et al., "Improving Processability and Efficiency of Resonant TADF Emitters: A Design Strategy," Adv. Optical Mater. 2020, 8, 1901627, 10 pp.
(Continued)

*Primary Examiner* — Gregory D Clark
(74) *Attorney, Agent, or Firm* — CANTOR COLBURN LLP

(57) ABSTRACT

Provided are a heterocyclic compound represented by Formula 1 and Formula 2, an organic light-emitting device including the heterocyclic compound, and an electronic apparatus including the organic light-emitting device:
(Continued)

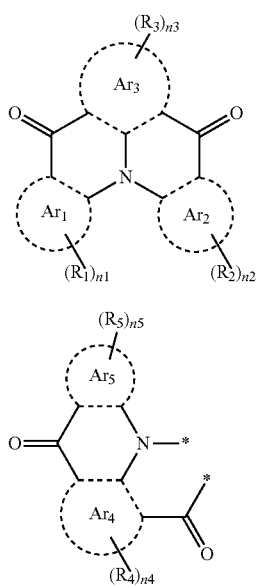

Formula 1

Formula 2 wherein, in Formula 1 and Formula 2, the substituents may be understood by referring to the detailed description.

13 Claims, 10 Drawing Sheets

(51) Int. Cl.
 H10K 85/60 (2023.01)
 H10K 50/11 (2023.01)
 H10K 50/12 (2023.01)
 H10K 101/10 (2023.01)
 H10K 101/30 (2023.01)
 H10K 101/40 (2023.01)
(52) U.S. Cl.
 CPC ......... H10K 50/12 (2023.02); H10K 2101/10 (2023.02); H10K 2101/30 (2023.02); H10K 2101/40 (2023.02)

(56) References Cited

U.S. PATENT DOCUMENTS

| 9,923,297 | B2 | 3/2018 | Sekino et al. |
| 2016/0315259 | A1 | 10/2016 | Fennimore et al. |
| 2020/0052212 | A1 | 2/2020 | Tasaki et al. |
| 2022/0181556 | A1 | 6/2022 | Miyazaki et al. |
| 2022/0359833 | A1 | 11/2022 | Jeon et al. |
| 2023/0097695 | A1 | 3/2023 | Jeon et al. |

FOREIGN PATENT DOCUMENTS

| CN | 110437229 A | 11/2019 | |
| CN | 110790782 A | 2/2020 | |
| CN | 110981871 A | 4/2020 | |
| CN | 111574519 A | * 8/2020 | ............. H01L 51/54 |
| CN | 111606906 A | 9/2020 | |
| EP | 3109253 B1 | 10/2018 | |
| EP | 3787056 A1 | 3/2021 | |
| JP | 2815472 A | 10/1998 | |
| JP | 2008247887 A | 10/2008 | |
| JP | 2015054426 A | 3/2015 | |
| JP | 2018018731 A | 2/2018 | |
| JP | 2022091124 A | 6/2022 | |
| KR | 20220119909 A | 8/2022 | |
| WO | 2011159872 A1 | 12/2011 | |
| WO | 2015102118 A1 | 7/2015 | |
| WO | 2018186404 A1 | 10/2018 | |

OTHER PUBLICATIONS

Extended European Search Report dated May 17, 2022, issued in EP Patent Application No. 21210112.5, 6 pp.
Taisei Taniguchi et al., "Construction of Nitrogen-containing Polycyclic Aromatic Compounds by Intramolecular Oxidative C—H/C—H Coupling of Bis(9H-carbazol-9-yl)benzenes and Their Properties," Chem. Lett. 2019, 48, 1160-1163.
Takuji Hatakeyama et al., "Ultrapure Blue Thermally Activated Delayed Fluorescence Molecules: Efficient HOMO-LUMO Separation by the Multiple Resonance Effect," Adv. Mater. 2016, 28, 2777-2781.
Xing Li et al., "Thermally Activated Delayed Fluorescence Carbonyl Derivatives for Organic Light-Emitting Diodes with Extremely Narrow Full Width at Half-Maximum ," ACS Appl. Mater. & Interfaces 2019, 11, 13472-13480.
Yasuhiro Kondo et al., "Narrowband deep-blue organic light-emitting diode featuring an organoboron-based emitter," Nature. Photonics 2019, 13, 678-682.
Yi Yuan et al., "The Design of Fused Amine/Carbonyl System for Efficient Thermally Activated Delayed Fluorescence: Novel Multiple Resonance Core and Electron Acceptor," Adv. Optical Mater. 2019, 7, 1801536, 6 pp.
English Abstract of CN 110981871.
English Abstract of CN 111606906.
English Translation of Office Action dated Dec. 3, 2024, issued in corresponding JP Patent Application No. 2020-216562, 3 pp.
English Translation of Office Action dated Oct. 8, 2024, issued in corresponding JP Patent Application No. 2020-216562, 4 pp.
Office Action dated Dec. 3, 2024, issued in corresponding JP Patent Application No. 2020-216562, 3 pp.
Office Action dated Oct. 8, 2024, issued in corresponding JP Patent Application No. 2020-216562, 4 pp.

* cited by examiner

HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

CROSS-REFERENCE TO RELATED APPLICATIONS

This application claims priority under 35 U.S.C. § 119 to Japanese Patent Application No. 2020-216562, filed on Dec. 25, 2020, in the Japanese Patent Office and to Korean Patent Application No. 10-2021-0053758, filed on Apr. 26, 2021, in the Korean Intellectual Property Office, the disclosures of which are incorporated by reference herein in their entirety.

BACKGROUND

1. Field

The present disclosure relates to a heterocyclic compound, an organic light-emitting device including the heterocyclic compound, and an electronic apparatus including the organic light-emitting device.

2. Description of the Related Art

Organic light-emitting devices (OLEDs) are self-emissive devices that, as compared with conventional devices, have wide viewing angles, high contrast ratios, short response times, and excellent brightness, driving voltage, and response speed characteristics, and produce full-color images.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. The excitons may transition from an excited state to a ground state, thus generating light.

SUMMARY

One or more embodiments relate to a heterocyclic compound, an organic light-emitting device including the heterocyclic compound, and an electronic apparatus including the organic light-emitting device, and more particularly to a heterocyclic compound that may improve luminescence efficiency of an organic light-emitting device, the heterocyclic compound having a narrow width of an emission spectrum and improved colorimetric purity and emitting blue light.

Additional aspects will be set forth in part in the description which follows and, in part, will be apparent from the description, or may be learned by practice of the presented embodiments of the disclosure.

According to an aspect of an embodiment, a heterocyclic compound is represented by Formula 1 and Formula 2:

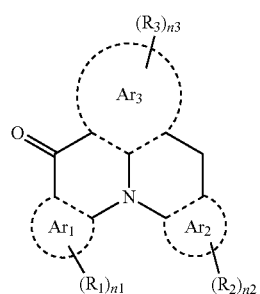

Formula 1

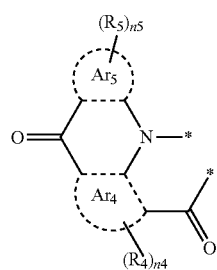

Formula 2 wherein, in Formulae 1 and 2, $Ar_1$ to $Ar_5$ are each independently an aromatic hydrocarbon ring having 6 or more and 14 or fewer ring-forming atoms or a heteroaromatic ring having 5 or more and 14 or fewer ring-forming atoms, $R_1$ to $R_5$ are each independently a hydrogen atom, a deuterium atom, a halogen atom, a substituted or unsubstituted alkyl group, a substituted or unsubstituted alkenyl group, a substituted or unsubstituted alkynyl group, a substituted or unsubstituted cycloalkyl group, a substituted or unsubstituted alkyl cycloalkyl group, a substituted or unsubstituted cycloalkenyl group, a substituted or unsubstituted alkyl cycloalkenyl group, a substituted or unsubstituted heterocycloalkyl group, a substituted or unsubstituted heterocycloalkenyl group, a substituted or unsubstituted haloalkyl group, a substituted or unsubstituted halocycloalkyl group, a substituted or unsubstituted alkoxy group, a substituted or unsubstituted cycloalkoxy group, a substituted or unsubstituted alkylthio group, a substituted or unsubstituted cycloalkylthio group, a substituted or unsubstituted aryl group, a substituted or unsubstituted alkyl aryl group, a substituted or unsubstituted heteroaryl group, a substituted or unsubstituted alkyl heteroaryl group, a substituted or unsubstituted aryloxy group, a substituted or unsubstituted heteroaryloxy group, a substituted or unsubstituted arylthio group, a substituted or unsubstituted heteroarylthio group, or a substituted or unsubstituted amino group, n1 is 0, 1, 2, 3, 4, 5, or 6, n2 and n5 are each independently 0, 1, 2, 3, 4, 5, 6, 7, or 8, n3 and n4 are each independently 0, 1, 2, 3, 4, 5, 6, or 7, when one of n1 to n5 is 2 or greater, each of $R_1(s)$ to $R_5(s)$ may be identical to or different from each other, and

* in Formula 2 indicates a binding site to a ring-forming atom of $Ar_1$ in Formula 1, a ring-forming atom of $Ar_2$ in Formula 1, or a ring-forming atom of $Ar_3$ in Formula 1, or a combination thereof.

According to an aspect of another embodiment, an organic light-emitting device includes a first electrode, a second electrode, and an organic layer between the first electrode and the second electrode and including an emission layer, and the organic light-emitting device includes the heterocyclic compound.

According to an aspect of another embodiment, an electronic apparatus includes the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
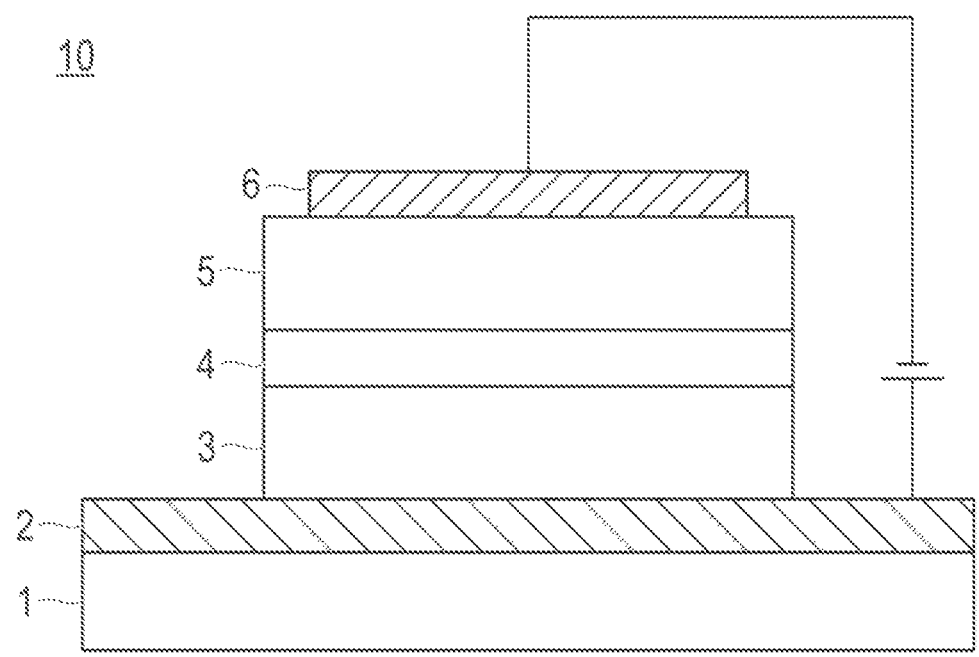
FIG. 1 is a schematic cross-sectional view illustrating an organic light-emitting device according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures It will be understood that relative terms are intended to encompass different orientations of the device in addition to the orientation depicted in the Figures For example, if the device in one of the figures is turned over, elements described as being on the "lower" side of other elements would then be oriented on "upper" sides of the other elements The exemplary term "lower," can therefore, encompasses both an orientation of "lower" and "upper," depending on the particular orientation of the figure Similarly, if the device in one of the figures is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

Unless otherwise defined, handling and measurement of physical properties may be performed at room temperature (from about 20° C. or higher and about 25° C. or lower) and at relative humidity (RH) from about 40% or greater and about 50% or less.

The term "X and Y may each independently be", as used herein, may be understood that X and Y may be identical to or different from each other.

The term "group derived from a ring", as used herein, refers to a group obtained by removing a hydrogen atom bound to a ring-forming atom in a ring structure.

Heterocyclic Compound

The heterocyclic compound may be represented by Formula 1 and Formula 2:

Formula 1

$$\begin{array}{c} (R_3)_{n3} \\ Ar_3 \\ O \\ Ar_1 \quad N \quad Ar_2 \\ (R_1)_{n1} \quad (R_2)_{n2} \end{array}$$

Formula 2

$$\begin{array}{c} (R_5)_{n5} \\ Ar_5 \\ O \\ Ar_4 \\ (R_4)_{n4} \end{array} N - *$$

wherein, in Formulae 1 and 2, $Ar_1$ to $Ar_5$ may each independently be an aromatic hydrocarbon ring having 6 or more and 14 or fewer ring-forming atoms or a heteroaromatic ring having 5 or more and 14 or fewer ring-forming atoms, $R_1$ to $R_5$ may each independently be a hydrogen atom, a deuterium atom, a halogen atom, a substituted or unsubstituted alkyl group, a substituted or unsubstituted cycloalkyl group, a substituted or unsubstituted alkenyl group, a substituted or unsubstituted alkynyl group, a substituted or unsubstituted cycloalkyl group, a substituted or unsubstituted alkyl cycloalkyl group, a substituted or unsubstituted cycloalkenyl group, a substituted or unsubstituted alkyl cycloalkenyl group, a substituted or unsubstituted heterocycloalkyl group, a substituted or unsubstituted heterocycloalkenyl group, a substituted or unsubstituted haloalkyl group, a substituted or unsubstituted halocycloalkyl group, a substituted or unsubstituted alkoxy group, a substituted or unsubstituted cycloalkoxy group, a substituted or unsubstituted alkylthio group, a substituted or unsubstituted cycloalkylthio group, a substituted or unsubstituted aryl group, a substituted or unsubstituted alkyl aryl group, a substituted or unsubstituted heteroaryl group, a substituted or unsubstituted alkyl heteroaryl group, a substituted or unsubstituted aryloxy group, a substituted or unsubstituted heteroaryloxy group, a substituted or unsubstituted arylthio group, a substituted or unsubstituted heteroarylthio group, or a substituted or unsubstituted amino group, n1 may be 0, 1, 2, 3, 4, 5, or 6, n2 and n5 may each independently be 0, 1, 2, 3, 4, 5, 6, 7, or 8, n3 and n4 may each independently be 0, 1, 2, 3, 4, 5, 6, or 7, when one of n1 to n5 is 2 or greater, each of $R_1(s)$ to $R_5(s)$ may be identical to or different from each other, and

* in Formula 2 indicates a binding site to a ring-forming atom of $Ar_1$ in Formula 1, a ring-forming atom of $Ar_2$ in Formula 1, a ring-forming atom of $Ar_3$ in Formula 1, or a combination thereof.

In Formulae 1 and 2, two or more neighboring groups of $R_1$, $R_2$, $R_3$, $R_4$, or $R_5$ are optionally linked to each other to form a substituted or unsubstituted $C_5$-$C_{30}$ carbocyclic group or a substituted or unsubstituted $C_1$-$C_{30}$ heterocyclic group.

In Formulae 1 and 2, when n1 to n5 are each 0, $R_1$ to $R_5$, corresponding to n1 to n5, may not be present, and each ring including $R_1$ to $R_5$ may not be substituted with $R_1$ to $R_5$, and a hydrogen atom is bound to the ring instead.

The heterocyclic compound may include one, two, or three instances of Formula 2. For example, Formula 2 may be bound to Formula 1 as follows:

1. When the heterocyclic compound includes one instance of Formula 2,
   (1-1) Formula 2 may be only bound to ring-forming atoms of $Ar_1$ in Formula 1,
   (1-2) Formula 2 may be only bound to ring-forming atoms of $Ar_2$ in Formula 1, or
   (1-3) Formula 2 may be only bound to ring-forming atoms of $Ar_3$ in Formula 1.

2. When the heterocyclic compound includes two instances of Formula 2,
   (2-1) one instance of Formula 2 may be bound to ring-forming atoms of $Ar_1$ in Formula 1, and another instance of Formula 2 may be bound to ring-forming atoms of $Ar_2$ in Formula 1,
   (2-2) one instance of Formula 2 may be bound to ring-forming atoms of $Ar_1$ in Formula 1, and another instance of Formula 2 may be bound to ring-forming atoms of $Ar_3$ in Formula 1,
   (2-3) one instance of Formula 2 may be bound to ring-forming atoms of $Ar_2$ in Formula 1, and another instance of Formula 2 may be bound to ring-forming atoms of $Ar_3$ in Formula 1,
   (2-4) one instance of Formula 2 may be bound to ring-forming atoms of $Ar_1$ in Formula 1, and another instance of Formula 2 may be bound to ring-forming atoms of An in Formula 1,
   (2-5) one instance of Formula 2 may be bound to ring-forming atoms of $Ar_2$ in Formula 1, and another instance of Formula 2 may be bound to ring-forming atoms of $Ar_2$ in Formula 1, or
   (2-6) one instance of Formula 2 may be bound to ring-forming atoms of $Ar_3$ in Formula 1, and another instance of Formula 2 may be bound to ring-forming atoms of $Ar_3$ in Formula 1.

3. When the heterocyclic compound includes three structures of Formula 2,
   (3-1) one instance of Formula 2 may be bound to ring-forming atoms of $Ar_1$ in Formula 1, another instance of Formula 2 may be bound to ring-forming atom of $Ar_2$ in Formula 1, and still another instance of Formula 2 may be bound to a ring-forming atom of Ar$_3$ in Formula 1.

In some embodiments, the heterocyclic compound may be in the form of (1-1).

In some embodiments, the heterocyclic compound represented by Formula 1 and Formula 2 may be represented by one of Formulae 1-1 to 1-4. When the heterocyclic compound is represented by one of Formulae 1-1 to 1-4, the heterocyclic compound may have a narrower blue emission spectrum and a higher colorimetric purity. Thus, an organic light-emitting device including the heterocyclic compound may have improved luminescence efficiency:

Formula 1-1

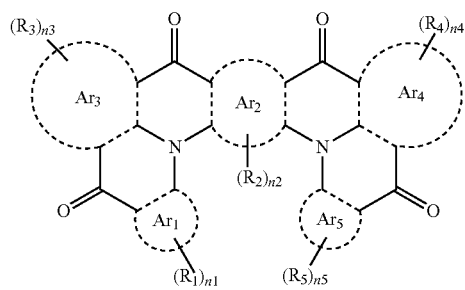

Formula 1-2

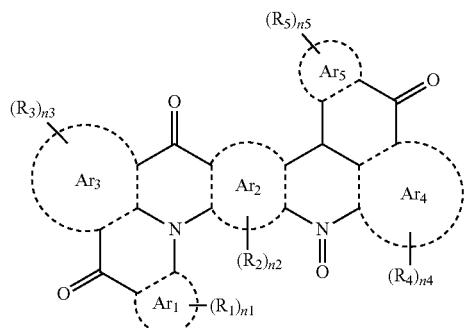

Formula 1-3

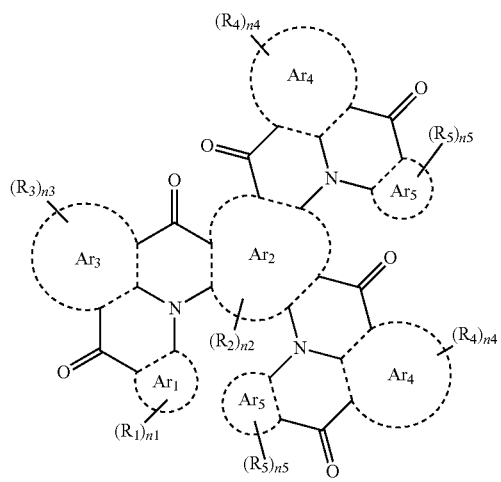

Formula 1-4

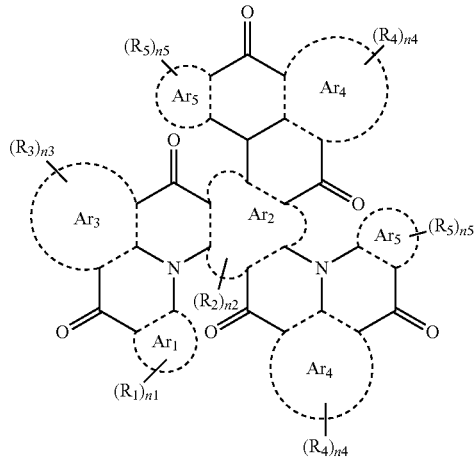

wherein, in Formulae 1-1 to 1-4,

Ar$_1$ to Ar$_5$, R$_1$ to R$_5$, and n1 to n5 may each be understood by referring to the descriptions of Ar$_1$ to Ar$_5$, R$_1$ to R$_5$, and n1 to n5 provided herein.

Ar$_1$ to Ar$_5$ in Formulae 1, 2, and 1-1 to 1-4 may each independently be an aromatic hydrocarbon ring having 6 or more and 14 or fewer ring-forming atoms or a heteroaromatic ring having 5 or more and 14 or fewer ring-forming atoms.

R$_1$ to R$_5$ in Formulae 1, 2, and 1-1 to 1-4 may each independently be a hydrogen atom, a deuterium atom, a halogen atom, a substituted or unsubstituted alkyl group, a substituted or unsubstituted alkenyl group, a substituted or unsubstituted alkynyl group, a substituted or unsubstituted cycloalkyl group, a substituted or unsubstituted alkyl cycloalkyl group, a substituted or unsubstituted cycloalkenyl group, a substituted or unsubstituted alkyl cycloalkenyl group, a substituted or unsubstituted heterocycloalkyl group, a substituted or unsubstituted heterocycloalkenyl group, a substituted or unsubstituted haloalkyl group, a substituted or unsubstituted halocycloalkyl group, a substituted or unsubstituted alkoxy group, a substituted or unsubstituted cycloalkoxy group, a substituted or unsubstituted alkylthio group, a substituted or unsubstituted cycloalkylthio group, a substituted or unsubstituted aryl group, a substituted or unsubstituted alkyl aryl group, a substituted or unsubstituted heteroaryl group, a substituted or unsubstituted alkyl heteroaryl group, a substituted or unsubstituted aryloxy group, a substituted or unsubstituted heteroaryloxy group, a substituted or unsubstituted arylthio group, a substituted or unsubstituted heteroarylthio group, or a substituted or unsubstituted amino group.

In Formulae 1, 2, and 1-1 to 1-4, the aromatic hydrocarbon ring may be a single ring or a condensed ring comprised of two or more rings. The number of ring-forming atoms in the aromatic hydrocarbon ring may be 6 or more and 14 or fewer, 6 or more and 10 or fewer, or 6. For example, the aromatic hydrocarbon ring may be a benzene ring, a naphthalene ring, an anthracene ring, or a phenanthrene ring. In some embodiments, the aromatic hydrocarbon ring may be a benzene ring.

In Formulae 1, 2, and 1-1 to 1-4, the heteroaromatic ring may be a single ring or a condensed ring comprised of two or more rings. The heteroaromatic ring may include at least one heteroatom (e.g., N, O, P, S, or Si) as a ring-forming atom, and the other ring-forming atoms may be C. The heteroatom may be N, O, or S. In some embodiments, the heteroatom may be N. The number of ring-forming atoms in the heteroaromatic ring may be 5 or more and 14 or fewer, 5 or more and 13 or fewer, 5 or more and 12 or fewer, or 5 or more and 10 or fewer. The number of heteroatoms in the heteroaromatic ring may be 1 or more and 3 or fewer, 1 or more and 2 or fewer, or 1. For example, the heteroaromatic ring may be a furan ring, a benzofuran ring, an isobenzofuran ring, a pyrrole ring, an indole ring, an isoindole ring, a thiophene ring, a benzothiophene ring, a benzo(c)thiophene ring, a selenophene ring, a benzoselenophene ring, a benzo(c)selenophene ring, an imidazole ring, a benzimidazole ring, a purine ring, a pyrazole ring, an indazole ring, an oxazole ring, a benzoxazole ring, an isooxazole ring, a benzoisooxazole ring, a thiazole ring, a benzothiazole ring, a pyridine ring, a quinoline ring, an isoquinoline ring, a pyrazine ring, a quinoxaline ring, an acridine ring, a pyrimidine ring, a quinazoline ring, a pyridazine ring, a cinnoline ring, a 1,2,3-triazine ring, a 1,2,4-triazine ring, a 1,3,5-triazine ring, a dibenzofuran ring, or a dibenzothiophene ring. For example, the heteroaromatic ring may be a pyridine ring, a pyridazine ring, a pyrimidine ring or a pyrazine ring.

In some embodiments, in Formulae 1, 2, and 1-1 to 1-4, $Ar_1$ to $Ar_5$ may each independently be a benzene ring, a naphthalene ring, an anthracene ring, a phenanthrene ring, a pyridine ring, a pyridazine ring, a pyrimidine ring, or a pyrazine ring.

In some embodiments, in Formulae 1, 2, and 1-1 to 1-4, $Ar_1$ to $Ar_5$ may each independently be a benzene ring, a pyridine ring, a pyridazine ring, a pyrimidine ring, or a pyrazine ring.

In some embodiments, in Formulae 1, 2, and 1-1 to 1-4, $Ar_1$ to $Ar_5$ may each be a benzene ring at the same time.

As used herein, the term "alkyl group" refers to a linear or branched saturated aliphatic hydrocarbon monovalent group. As used herein, the term "cycloalkyl group" refers to a monovalent saturated hydrocarbon monocyclic group. Examples of the alkyl group and the cycloalkyl group include a methyl group, an ethyl group, an n-propyl group, an iso-propyl group, an n-butyl group, a sec-butyl group, a tert-butyl group, an isobutyl group, a 2-ethylbutyl group, a 3,3-dimethylbutyl group, an n-pentyl group, an isopentyl group, a neopentyl group, a tert-pentyl group, a pentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-tert-butylcyclohexyl group, an n-heptyl group, a 1-methylheptyl group, a 2,2-dimethylheptyl group, a 2-ethylheptyl group, a 2-butylheptyl group, an n-octyl group, a tert-octyl group, a 2-ethyloctyl group, a 2-butyloctyl group, a 2-hexyloctyl group, a 3,7-dimethyloctyl group, a cyclooctyl group, an n-nonyl group, an n-decyl group, or an adamantyl group.

As used herein, the term "alkenyl group" refers to a hydrocarbon group formed by including at least one carbon-carbon double bond in the middle or at the terminus of an alkyl group, and examples thereof include an ethenyl group, a propenyl group, and a butenyl group.

As used herein, the term "cycloalkenyl group" refers to a monovalent monocyclic group that has at least one carbon-carbon double bond in the ring thereof and that has no aromaticity, and non-limiting examples thereof include a cyclopentenyl group, a cyclohexenyl group, and a cycloheptenyl group.

As used herein, the term "alkylnyl group" refers to a hydrocarbon group formed by including at least one carbon-carbon triple bond in the middle or at the terminus of an alkyl group, and examples thereof include an ethynyl group, and a propynyl group.

As used herein, the term "alkyl cycloalkyl group" refers to a monovalent saturated hydrocarbon monocyclic group attached to an alkylene group. As used herein, an "alkylene group" refers to a divalent group having the same structure as the alkyl group. A non-limiting example includes a —$CH_2$-cyclopropyl group.

As used herein, the term "heterocycloalkyl group" refers to a monovalent saturated monocyclic group having at least one heteroatom as a ring-forming atom. Non-limiting examples thereof include a tetrahydrofuranyl group, and a tetrahydrothiophenyl group.

As used herein, the term "heterocycloalkenyl group" refers to a monovalent monocyclic group that has at least one heteroatom as a ring-forming atom and at least one carbon-carbon double bond in its ring. Examples of the $C_1$-$C_{10}$ heterocycloalkenyl group are a 2,3-dihydrofuranyl group, and a 2,3-dihydrothiophenyl group.

As used herein, the term "alkyl heterocycloalkyl group" refers to a monovalent saturated monocyclic group having at least one heteroatom as a ring-forming atom attached to an alkylene group. A non-limiting example includes a —$CH_2$— tetrahydrofuranyl group.

As used herein, the term "haloalkyl group" refers to an alkylene group substituted with a halogen. The alkyl group may be a linear form or a branched form. The number of carbon atoms in the haloalkyl group is not particularly limited and may be 1 or more and 20 or fewer, or for example, 10 or fewer or 4 or fewer. In Formulae 1, 2, and 1-1 to 1-4, the term "halocycloalkyl group" refers to a monovalent cycloalkyl group substituted with a halogen. The halocycloalkyl group may be substituted with linear or branched alkyl groups.

The number of carbon atoms in the halocycloalkyl group is not particularly limited and may be 3 or more and 10 or fewer, or for example, 8 or fewer or 6 or fewer. Examples of the haloalkyl group and the halocycloalkyl group are not particularly limited. At least one hydrogen atom in the alkyl group and the cycloalkyl group may be substituted with a halogen atom. The halogen atom may be a fluorine atom, a chlorine atom, a bromine atom, or an iodine atom. In some embodiments, examples of the haloalkyl group include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a chloroethyl group, a bromoethyl group, and an iodoethyl group.

As used herein, the term "alkoxy group" refers to a monovalent group represented by —$OA_{101}$ (wherein $A_{101}$ is the alkyl group). The alkyl group may be a linear form or a branched form. The number of carbon atoms in the alkoxy group is not particularly limited and may be 1 or more and 20 or fewer, or for example, 10 or fewer or 4 or fewer. As used herein, the term "cycloalkoxy group" refers to a monovalent group represented by —$OA_{102}$ (wherein $A_{102}$ is the cycloalkyl group). The cycloalkoxy group may be substituted with linear or branched alkyl groups. The number of carbon atoms in the cycloalkoxy group is not particularly limited and may be 3 or more and 10 or fewer, or for example, 8 or fewer or 6 or fewer. Examples of the alkoxy group and the cycloalkoxy group are not particularly limited. Examples of the alkoxy group and the cycloalkoxy group may include a methoxy group, an ethoxy group, a n-propyloxy group, an isopropyloxy group, an n-butyloxy group, a sec-butyloxy group, a tert-butyloxy group, an isobutyloxy group, a 2-ethylbutyloxy group, a 3,3-dimethylbutyloxy group, an n-pentyloxy group, an isopentyloxy group, a neopentyloxy group, a tert-pentyloxy group, a cyclopentyloxy group, a 1-methylpentyloxy group, a 3-methylpentyloxy group, a 2-ethylpentyloxy group, a 4-methyl-2-pentyloxy group, an n-hexyloxy group, a 1-methylhexyloxy group, a 2-ethylhexyloxy group, a 2-butylhexyloxy group, a cyclohexyloxy group, a 4-methylcyclohexyloxy group, a 4-tert-butylcyclohexyloxy group, an n-heptyloxy group, a 1-methylheptyloxy group, a 2,2-dimethylheptyloxy group, a 2-ethylheptyloxy group, a 2-butylheptyloxy group, an n-octyloxy group, a tert-octyloxy group, a 2-ethyloctyloxy group, a 2-butyloctyloxy group, a 2-hexyloctyloxy group, a 3,7-dimethyloctyloxy group, a cyclooxy group, an n-nonyloxy group, an n-decyloxy group, and an adamantyloxy group.

As used herein, the term "alkylthio group" refers to a monovalent group represented by —$SA_{110}$ (wherein $A_{110}$ is the alkyl group). The alkyl group may be a linear form or a branched form. The number of carbon atoms in the alkylthio group is not particularly limited and may be 1 or more and 20 or fewer, or for example, 10 or fewer or 4 or fewer. As used herein, the term "cycloalkylthio group" refers to a monovalent group represented by —$SA_{111}$ (wherein $A_{111}$ is the cycloalkyl group). The cycloalkylthio group may be substituted with linear or branched alkyl groups. The number of carbon atoms in the cycloalkylthio group is not particularly limited and may be 3 or more and 10 or fewer, or for example, 8 or fewer or 6 or fewer.

As used herein, the term "aryl group" refers to a group derived from a hydrocarbon ring having aromaticity partially or as a whole. When the aryl group includes a hydrocarbon ring having aromaticity partially or as a whole, the hydrocarbon ring may be bound via a single bond or condensed. When the aryl group includes a hydrocarbon ring having aromaticity partially or as a whole, a plurality of hydrocarbon rings may share one atom. The number of carbon atoms in the aryl group is not particularly limited and may be 6 or more and 30 or fewer, 6 or more and 12 or fewer, or 6 or fewer. Examples of the aryl group are not particularly limited. Examples of the aryl group include a phenyl group, a biphenyl group, a terphenyl group, a naphthyl group, a fluorenyl group, an anthracenyl group, a terphenyl group, a quaterphenyl group, a pentaphenyl group, a hexyphenyl group, a triphenylenyl group, a pyrenyl group, a benzofluorenyl group, and a chrysenyl group. In some embodiments, the aryl group may be a phenyl group.

As used herein, the term "alkyl aryl group" refers to a monovalent aryl group attached to an alkylene group. A non-limiting example of an alkyl aryl group includes a —$CH_2$-phenyl group.

As used herein, the term "heteroaryl group" refers to a group derived from a hetero ring having aromaticity partially or as a whole. When the heteroaryl group includes a hetero ring having aromaticity partially or as a whole, the hetero ring may be bound via a single bond or condensed. When the heteroaryl group includes a hetero ring having aromaticity partially or as a whole, a plurality of hetero rings may share one atom. The heteroatom included in the heteroaryl group is not particularly limited. For example, the heteroaryl group may include at least one heteroatom (e.g., N, O, P, S, Si, Se, or Ge) as a ring-forming atom and 3 to 30 carbon atoms. The number of ring-forming atoms in the heteroaryl group is not particularly limited. The number of ring-forming atoms may be 5 or more and 30 or fewer, 5 or more and 14 or fewer, or 5 or more and 13 or fewer. The number of heteroatoms in the heteroaryl group is not particularly limited. The number of ring-forming atoms may be 1 or more and 3 or fewer, 1 or more and 2 or fewer, or 1.

Examples of the heteroaryl group include a thienyl group, a furanyl group, a pyrrolyl group, an imidazole group, a thiazolyl group, an oxazolyl group, an oxadiazolyl group, a triazolyl group, a pyridyl group, a bipyridyl group, a pyrimidyl group, a triazinyl group, a triazolyl group, an acridinyl group, a pyridazinyl group, a pyridinyl group, a quinolinyl group, a quinazolinyl group, a quinoxalinyl group, a phenoxazinyl group, a phthalazinyl group, a pyridopyrimidinyl group, a pyridopyrazinyl group, a pyrazinopyrazinyl group, an isoquinolinyl group, an indolyl group, a carbazolyl group, a benzocarbazolyl group, a benzoxazolyl group, a benzimidazolyl group, a benzothiazolyl group, a benzothiophenyl group, a dibenzothiophenyl group, a thienothiophenyl group, a benzofuranyl group, a phenanthrolinyl group, a thiazolyl group, an isoxazolyl group, an oxadiazolyl group, a thiadiazolyl group, a phenothiazinyl group, a dibenzosilolyl group, a dibenzofuranyl group, and a xanthonyl group.

As used herein, the term "alkyl heteroaryl group" refers to a monovalent hetero aryl group attached to an alkylene group. A non-limiting example of an alkyl heteroaryl group includes a —$CH_2$-pyridyl group.

As used herein, the term "aryloxy" refers to a monovalent group represented by —$OA_{104}$ (wherein $A_{104}$ is the aryl group). The number of carbon atoms in the aryloxy group is not particularly limited and may be 6 or more and 30 or fewer, 6 or more and 12 or fewer, or 6 or fewer. Examples of the aryloxy group include a phenyloxy group, a biphenyloxy group, a terphenyloxy group, a naphthyloxy group, a fluorenyloxy group, an anthracenyloxy group, a terphenyloxy group, a quaterphenyloxy group, a pentaphenyloxy group, a triphenyloxy group, a pyrenyloxy group, a benzofluoreneoxy group, and a chrysenyloxy group.

As used herein, the term "arylthio" refers to a monovalent group represented by —$SA_{105}$ (wherein $A_{105}$ is the aryl group). The number of carbon atoms in the arylthio group is not particularly limited and may be 6 or more and 30 or fewer, 6 or more and 12 or fewer, or 6 or fewer. Examples of the arylthio group are not particularly limited. The arylthio group may be a phenylthio group, a biphenylthio group, a terphenylthio group, a naphthylthio group, a fluorenylthio group, anthracenylthio group, a quaterphenylthio group, a pentaphenylthio group, a triphenylthio group, a pyrenylthio group, a benzofluorenethio group, a chrysenylthio group, or a combination thereof.

As used herein, the term "heteroaryloxy" refers to a monovalent group represented by —$OA_{106}$ (wherein $A_{106}$ is the heteroaryl group). Heteroatom(s) included in the heteroaryloxy group are not particularly limited. For example, the heteroaryloxy group may include at least one heteroatom (e.g., N, O, P, S, Si, Se, or Ge) as a ring-forming atom and 3 to 30 carbon atoms. The number of ring-forming atoms in the heteroaryloxy group is not particularly limited. The number of ring-forming atoms may be 5 or more and 30 or fewer, 5 or more and 14 or fewer, or 5 or more and 13 or fewer. The number of heteroatoms in the heteroaryloxy group is not particularly limited. The number of ring-forming atoms may be 1 or more and 3 or fewer, 1 or more and 2 or fewer, or 1. Examples of the heteroaryloxy group are not particularly limited. Examples of the heteroaryloxy group include a thienyloxy group, a furanyloxy group, a pyrrolyloxy group, an imidazoloxy group, a thiazolyloxy group, an oxazolyloxy group, an oxadiazolyloxy group, a triazolyloxy group, a pyridyloxy group, a bipyridyloxy group, a pyrimidyloxy group, a triazinyloxy group, a triazolyloxy group, an acridinyloxy group, a pyridazinyloxy group, a pyridinyloxy group, a quinolinyloxy group, a quinazolinyloxy group, a quinoxalinyloxy group, a phenoxazinyloxy group, a phthalazinyloxy group, a pyridopyrimidinyloxy group, a pyridopyrazinyloxy group, a pyrazinopyrazinyloxy group, an isoquinolinyloxy group, an indolyloxy group, a carbazolyloxy group, a benzocarbazolyloxy group, a benzoxazolyloxy group, a benzimidazolyloxy group, a benzothiazolyloxy group, a benzothiophenyloxy group, a dibenzothiophenyloxy group, a thienothiophenyloxy group, a benzofuranyloxy group, a phenanthrolinyloxy group, a thiazolyloxy group, an isooxazolyloxy group, an oxadiazolyloxy group, a thiadiazolyloxy group, a phenothiazinyloxy group, a dibenzosilolyloxy group, a dibenzofuranyloxy group, and a xanthonyloxy group.

In Formulae 1, 2, and 1-1 to 1-4, the term "heteroarylthio" refers to a monovalent group represented by —$SA_{107}$ (wherein $A_{107}$ is the heteroaryl group). Heteroatom(s) included in the heteroarylthio group are not particularly limited. For example, the heteroarylthio group may include at least one heteroatom (e.g., N, O, P, S, Si, Se, or Ge) as a ring-forming atom and 3 to 30 carbon atoms. The number of ring-forming atoms in the heteroarylthio group is not particularly limited and may be 5 or more and 30 or fewer, 5 or more and 14 or fewer, or 5 or more and 13 or fewer. The number of heteroatoms in the heteroarylthio group is not particularly limited. The number of ring-forming atoms may be 1 or more and 3 or fewer, 1 or more and 2 or fewer, or 1. Examples of the heteroarylthio group are not particularly limited and include a thienylthio group, a furanylthio group, a pyrrolylthio group, an imidazolylthio group, a thiazolylthio group, an oxazolylthio group, an oxadiazolylthio group, a triazolylthio group, a pyridylthio group, a bipyridylthio group, a pyrimidylthio group, a triazinylthio group, a triazolylthio group, an acridinylthio group, a pyridazinylthio group, a pyridinylthio group, a quinolinylthio group, a quinazolinylthio group, a quinoxalinylthio group, a phenoxazinylthio group, a phthalazinylthio group, a pyridopyrimidinylthio group, a pyridopyrazinylthio group, a pyrazinopyrazinylthio group, an isoquinolinylthio group, an indolylthio group, a carbazolylthio group, a benzocarbazolylthio group, a benzoxazolylthio group, a benzimidazolylthio group, a benzothiazolylthio group, a benzothiophenylthio group, a dibenzothiophenylthio group, a thienothiophenylthio group, a benzofuranylthio group, a phenanthrolinylthio group, a thiazolylthio group, an isooxazolylthio group, an oxadiazolylthio group, a thiadiazolylthio group, a phenothiazinylthio group, a dibenzosilolylthio group, a dibenzofuranylthio group, and a xanthonylthio group.

In Formulae 1, 2, and 1-1 to 1-4, a halogen atom is not particularly limited. For example, the halogen atom may be a fluorine atom, a chlorine atom, a bromine atom, or an iodine atom. In some embodiments, a halogen atom may be a fluorine atom.

In Formulae 1, 2, and 1-1 to 1-4, an amino group may be a substituted amino group represented by —$NH_2$ or —NHR or a bisubstituted amino group represented by —NRR', wherein R and R' may each independently be an organic group. R and R' may not each be particularly limited. For example, R and R' may each be a substituted or unsubstituted alkyl group, a substituted or unsubstituted alkenyl group, a substituted or unsubstituted alkynyl group, a substituted or unsubstituted aryl group, or a substituted or unsubstituted heteroaryl group, and R and R' may be identical to or different from each other.

The alkyl group, the alkenyl group, and the alkynyl group in R and R' may each be a linear form, a branched form, or a ring form, or for example, a linear form. The number of carbon atoms in the alkyl group, the alkenyl group, and the alkynyl group is not particularly limited and may be 1 or more and 20 or fewer, or for example, 10 or fewer or 4 or fewer. Examples of the alkyl group are not particularly limited, and the alkyl group may be a methyl group, an ethyl group, an n-propyl group, an iso-propyl group, an n-butyl group, a sec-butyl group, a tert-butyl group, an isobutyl group, a 2-ethylbutyl group, a 3,3-dimethylbutyl group, an n-pentyl group, an isopentyl group, a neopentyl group, a tert-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-tert-butylcyclohexyl group, an n-heptyl group, a 1-methylheptyl group, a 2,2-dimethylheptyl group, a 2-ethylheptyl group, a 2-butylheptyl group, an n-octyl group, a tert-octyl group, a 2-ethyloctyl group, a 2-butyloctyl group, a 2-hexyloctyl group, a 3,7-dimethyloctyl group, a cyclooctyl group, an n-nonyl group, an n-decyl group, or an adamantyl group. The alkenyl group is not particularly limited. The alkenyl group may be a vinyl group, a 2-prophenyl group, a 2-butenyl group, a 3-butenyl group, a 1-methyl-2-prophenyl group, a 2-methyl-2-prophenyl group, a 2-pentenyl group, a 3-pentenyl group, a 4-pentenyl group, a 1-methyl-2-butenyl group, a 2-methyl-2-butenyl group, a 3-methyl-2-butenyl group, a 1-methyl-3-butenyl group, a 2-methyl-3-butenyl group, a 3-methyl-3-butenyl group, a 1,1-dimethyl-2-prophenyl group, a 1,2-dimethyl-2-prophenyl group, or a 1-ethyl-2-prophenyl group. The alkynyl group is not particularly limited. The alkynyl group may be a 2-butynyl group, a 3-pentyl group, a hexynyl group, a heptynyl group, an octynyl group, or decynyl group.

The aryl group in R and R' may respectively be understood by referring to the description of the aryl group provided herein. In some embodiments, the aryl group in R and R' may be a monovalent group derived from an aromatic hydrocarbon ring having 6 or more ring-forming atoms. In addition, the aromatic hydrocarbon ring having 6 or more ring-forming atoms may be understood by referring to the description of the aromatic hydrocarbon ring provided herein.

The heteroaryl group in R and R' may respectively be understood by referring to the description of the heteroaryl group provided herein. In some embodiments, the heteroaryl group in R and R' may be a monovalent group derived from a heteroaromatic ring having 5 or more ring-forming atoms. In addition, the heteroaromatic ring having 5 or more ring-forming atoms may be understood by referring to the description of the heteroaromatic ring provided herein.

In some embodiments, an amino group may be a bisubstituted amino group represented by —NRR'. R and R' may each independently be an aryl group or a heteroaryl group. Examples of the amino group are not particularly limited. Examples of the amino group may include a N, N-diarylamino group, a N, N-diheteroarylamino group, or a N-aryl-N-heteroarylamino group. In addition, R and R' may each independently be a monovalent group derived from an aromatic hydrocarbon ring having 6 or more and 30 or fewer ring-forming atoms or a monovalent group derived from a heteroaromatic ring having 5 or more and 30 or fewer ring-forming atoms. In particular, R and R' may each independently be a monovalent group derived from an aromatic hydrocarbon ring having 6 or more and 30 or fewer ring-forming atoms. The aromatic hydrocarbon ring and the heteroaromatic ring may respectively be understood by referring to the descriptions of the aromatic hydrocarbon ring and the heteroaromatic ring provided herein. In some embodiments, the amino group may be a N, N-diphenylamino group.

In Formulae 1, 2, and 1-1 to 1-4, the alkyl group, the alkenyl group, the alkynyl group, the cycloalkyl group, the alkyl cycloalkyl group, the cycloalkenyl group, the alkyl cycloalkenyl group, the heterocycloalkyl group, the alkyl heterocycloalkyl group, the haloalkyl group, the halocycloalkyl group, the alkoxy group, the cycloalkyoxy group, the alkyl thio group, the cycloalkylthio group, the aryl group, the alkyl aryl group, the heteroaryl group, the alkyl heteroaryl group, the aryloxy group, the heteroaryloxy group, the arylthio group, the heteroarylthio group, and the amino group may each be substituted. A substituent is not particularly limited, and the substituent may be, for example, an alkyl group, a cycloalkyl group, an alkenyl group, an alkynyl group, a deuterium atom, a halogen atom, a cyano group, an alkyoxy group, an alkylthio group, a silyl group, a germanyl group, an alkyl group substituted with a halogen, and an alkyl group substituted with a deuterium atom. In some embodiments, the substituent may be a fluorine atom or an alkyl group, and the substituent may be a methyl group, a tert-butyl group, or a fluorine atom. In Formulae 1, 2, and 1-1 to 1-4, the amino group may be a substituted amino group or a bisubstituted amino group, and a substituent bound to an alkyl group, an alkenyl group, or an alkynyl group, forming the amino group, may be, for example, a deuterium atom, a halogen atom, or a cyano group. In Formulae 1, 2, and 1-1 to 1-4, the amino group may be a substituted amino group or a bisubstituted amino group, to the groups bound to the N atom of the substituted amino group and the bisubstituted amino group include an aryl group and/or a heteroaryl group. The aryl and/or heteroaryl groups bound to the N atom of the substituted amino group and the bisubstituted amino group may be substituted with at least one substituent. Substituents may include, for example, an alkyl group, a cycloalkyl group, an alkenyl group, an alkynyl group, a deuterium atom, a halogen atom, a cyano group, an alkyoxy group, an alkylthio group, a silyl group, a germanyl group, an alkyl group substituted with a halogen, and an alkyl group substituted with a deuterium atom. In some embodiments, the substituent may be a fluorine atom or an alkyl group, before example, a methyl group, a tert-butyl group, or a fluorine atom, or for example, a methyl group or a fluorine atom. In addition, the substituents including the alkyl group, the alkenyl group, the alkynyl group, the halogen atom, and the alkyl group substituted with a deuterium atom, may respectively be understood by referring to the descriptions of the alkyl group, the alkenyl group, the alkynyl group, the halogen atom, and the alkyl group substituted with a deuterium atom provided herein.

In some embodiments, the alkyl group may not be substituted with an alkyl group, and an alkylhalo group may not be further substituted with an alkyl group and/or a halogen atom.

In some embodiments, in Formulae 1, 2, and 1-1 to 1-4, $R_1$ to $R_5$ may each independently be a hydrogen atom, a deuterium atom, a halogen atom, a linear or branched unsubstituted alkyl group having 1 or more and 20 or fewer carbon atoms, a linear or branched unsubstituted alkenyl group having 2 or more and 20 or fewer carbon atoms, a linear or branched unsubstituted alkynyl group having 2 or more and 20 or fewer carbon atoms, a substituted or unsubstituted cycloalkyl group having 3 or more and 10 or fewer carbon atoms, a substituted or unsubstituted alkyl cycloalkyl group having 4 or more and 10 or fewer carbon atoms, a substituted or unsubstituted cycloalkenyl group having 3 or more and 10 or fewer carbon atoms, a substituted or unsubstituted alkyl cycloalkenyl group having 4 or more and 10 or fewer carbon atoms, a substituted or unsubstituted heterocycloalkyl group having 2 or more and 10 or fewer carbon atoms, a substituted or unsubstituted alkyl heterocycloalkyl group having 3 or more and 10 or fewer carbon atoms, a linear or branched unsubstituted haloalkyl group having 1 or more and 20 or fewer carbon atoms, a substituted or unsubstituted halocycloalkyl group having 3 or more and 10 or fewer carbon atoms, a linear or branched unsubstituted alkoxy group having 1 or more and 20 or fewer carbon atoms, a substituted or unsubstituted cycloalkyoxy group having 3 or more and 10 or fewer carbon atoms, a substituted or unsubstituted cycloalkylthio group having 3 or more and 10 or fewer carbon atoms, a substituted or unsubstituted aryl group having 6 or more and 30 or fewer carbon atoms, a substituted or unsubstituted alkyl aryl group having 7 or more and 30 or fewer carbon atoms, a substituted or unsubstituted aryloxy group having 6 or more and 30 or fewer carbon atoms, a substituted or unsubstituted arylthio group having 6 or more and 30 or fewer carbon atoms, a substituted or unsubstituted heteroaryl group having 3 or more and 30 or fewer carbon atoms, a substituted or unsubstituted alkyl heteroaryl group having 4 or more and 30 or fewer carbon atoms, a substituted or unsubstituted heteroaryloxy group having 3 or more and 30 or fewer carbon atoms, a substituted or unsubstituted heteroarylthio group having 3 or more and 30 or fewer carbon atoms, or a bisubstituted amino group represented by —NRR', and R and R' may each independently be a monovalent group derived from an aromatic hydrocarbon ring having 6 or more and 30 or fewer ring-forming atoms or a monovalent group derived from a heteroaromatic ring having 5 or more and 30 or fewer ring-forming atoms.

In some embodiments, in Formulae 1, 2, and 1-1 to 1-4, $R_1$ to $R_5$ may each independently be a hydrogen atom, a deuterium atom, a halogen atom, a linear or branched unsubstituted alkyl group having 1 or more and 20 or fewer carbon atoms, a substituted or unsubstituted cycloalkyl group having 3 or more and 10 or fewer carbon atoms, or a substituted or unsubstituted aryl group having 6 or more and 30 or fewer carbon atoms.

In some embodiments, in Formulae 1, 2, and 1-1 to 1-4, $R_1$ to $R_5$ may each independently be a hydrogen atom, a deuterium atom, —F, —CH$_3$, —CD$_3$, —CD$_2$H, —CDH$_2$, —CF$_3$, —CF$_2$H, —CFH$_2$, a group represented by one of Formulae 9-1 to 9-39, a group represented by one of Formulae 9-1 to 9-39 in which at least one hydrogen atom is substituted with a deuterium atom, a group represented by one of Formulae 9-1 to 9-39 in which at least one hydrogen atom is substituted with —F, a group represented by one of Formulae 10-12 to 10-130, a group represented by one of Formulae 10-12 to 10-130 in which at least one hydrogen atom is substituted with a deuterium atom, a group represented by one of Formulae 10-12 to 10-130 in which at least one hydrogen atom is substituted with —F, a group represented by one of Formulae 10-359 to 10-380, a group represented by one of Formulae 10-359 to 10-380 in which at least one hydrogen atom is substituted with a deuterium atom, a group represented by one of Formulae 10-359 to 10-380 in which at least one hydrogen atom is substituted with —F:
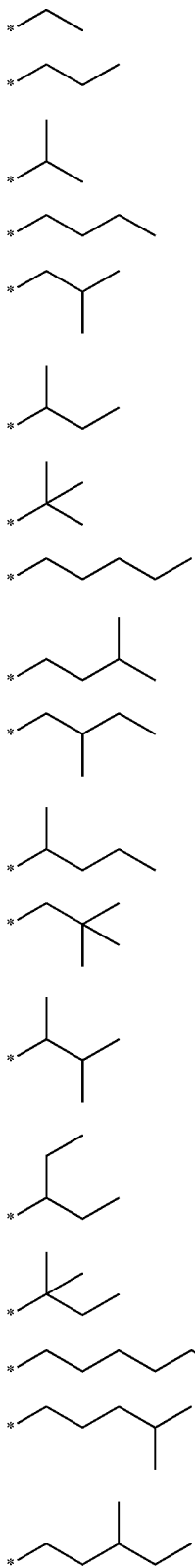
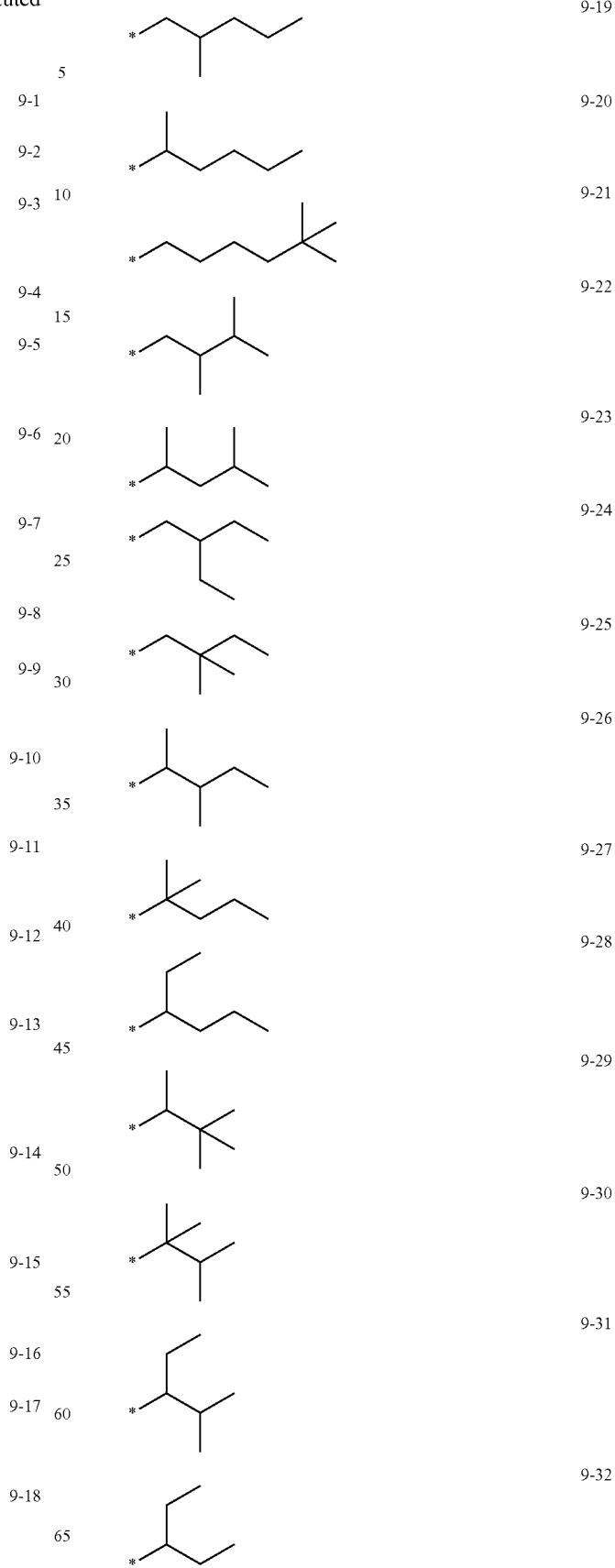

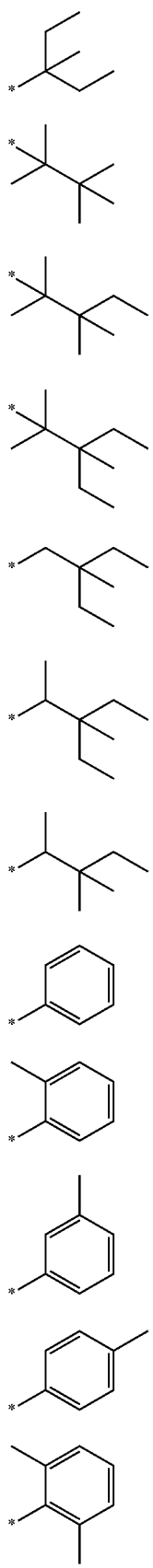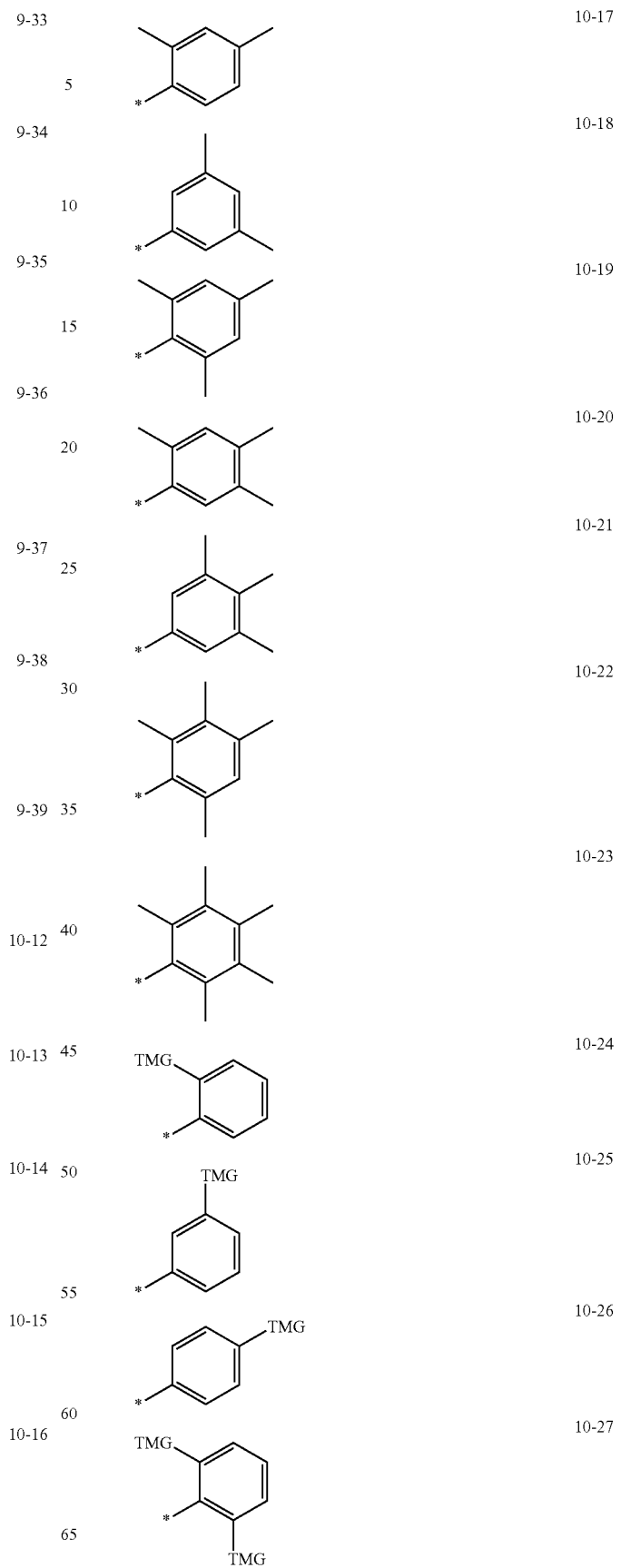

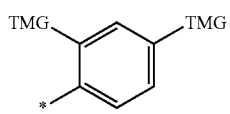
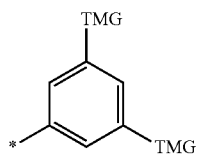
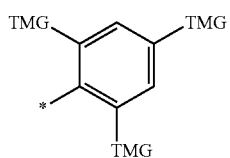
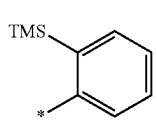
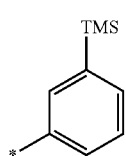
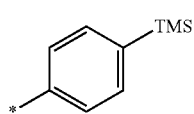
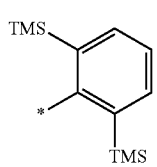
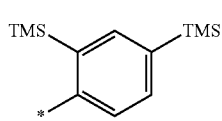
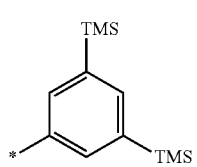
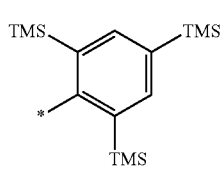
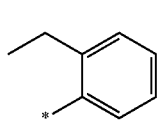
10-28
10-29
10-30
10-31
10-32
10-33
10-34
10-35
10-36
10-37
10-38
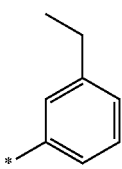
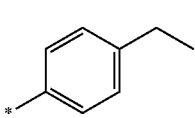
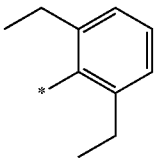
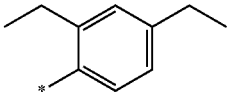
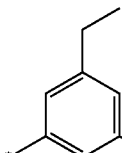
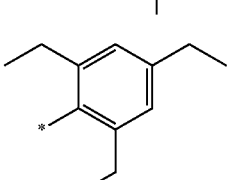
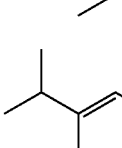
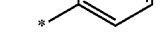
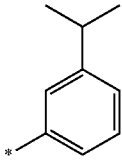
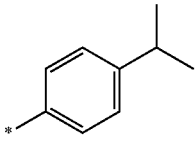
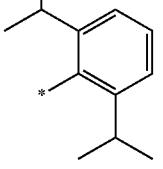
10-39
10-40
10-41
10-42
10-43
10-44
10-45
10-46
10-47
10-48

10-49
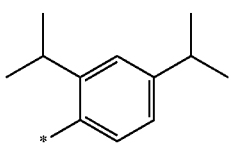
10-50
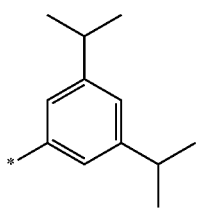
10-51
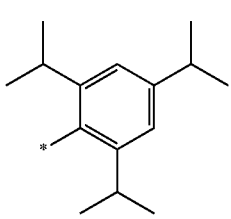
10-52
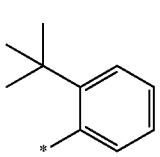
10-53
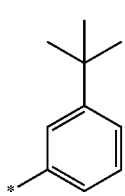
10-54
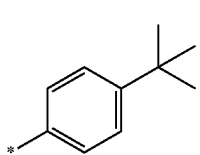
10-55
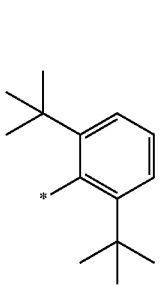
10-56
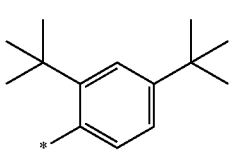
10-57
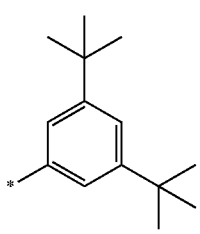
10-58
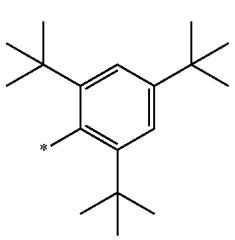
10-59
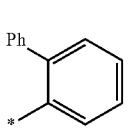
10-60
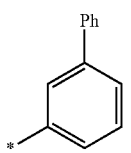
10-61
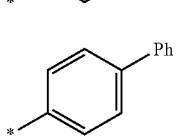
10-62
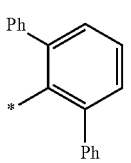
10-63
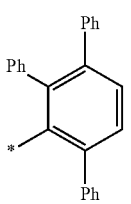
10-64
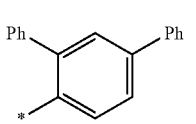
10-65
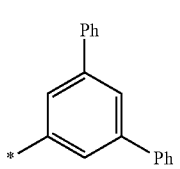

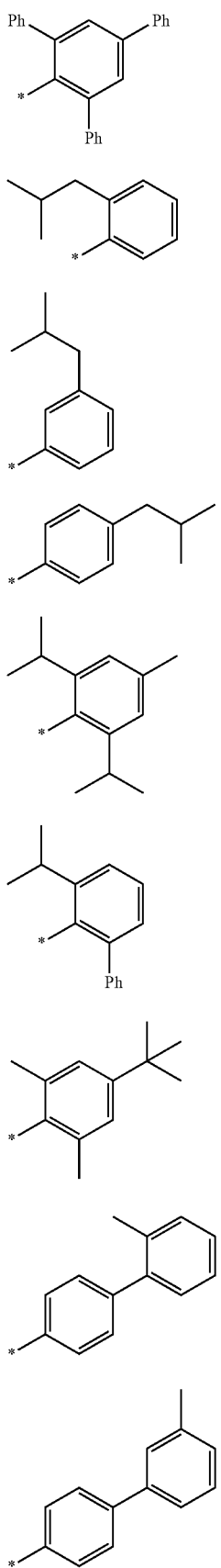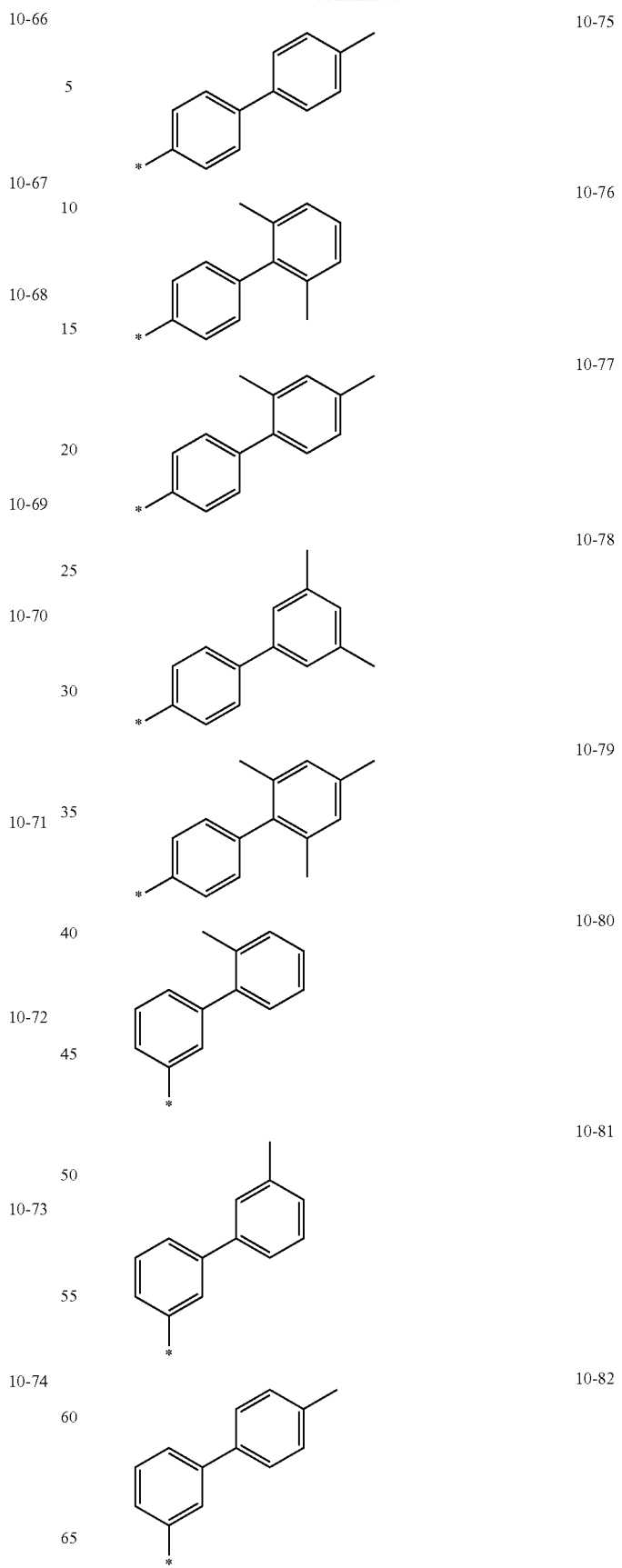

-continued
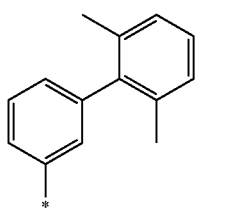
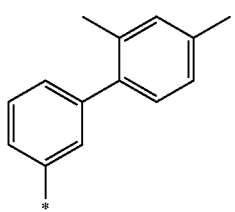
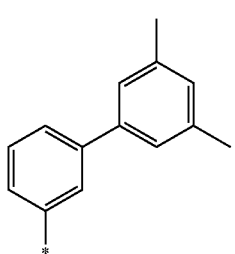
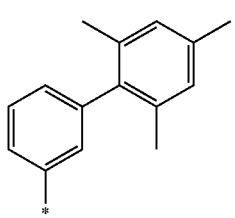
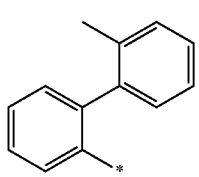
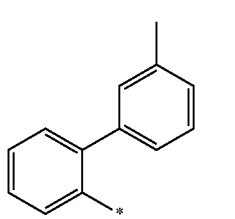
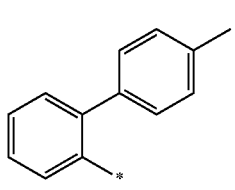
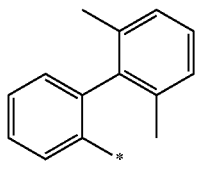
-continued
10-83
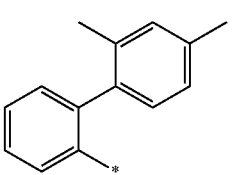
10-84
10-85
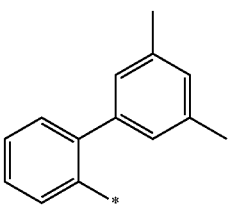
10-86
10-87
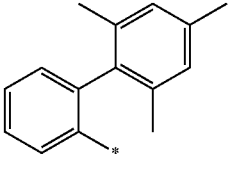
10-88
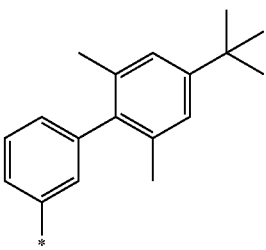
10-89
10-90
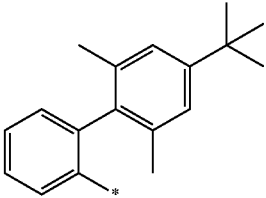
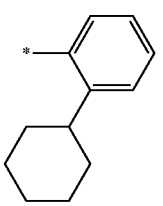
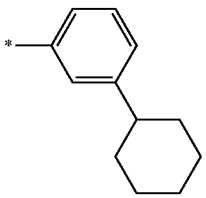
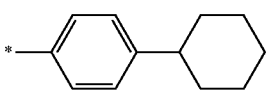
10-91
10-92
10-93
10-94
10-95
10-96
10-97
10-98

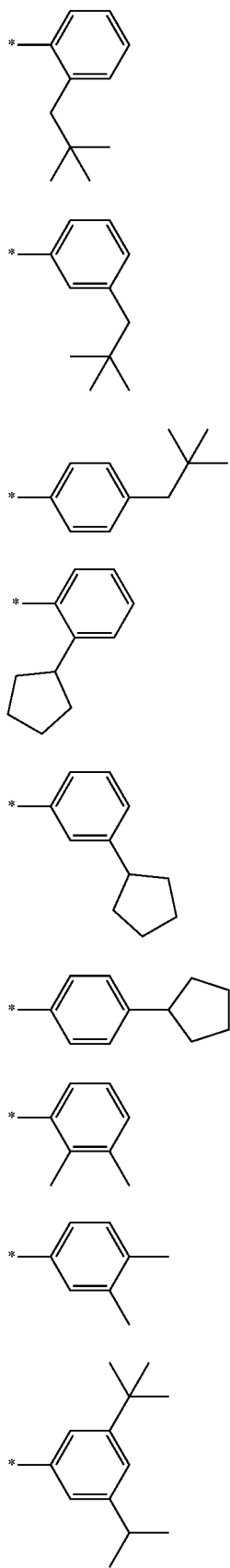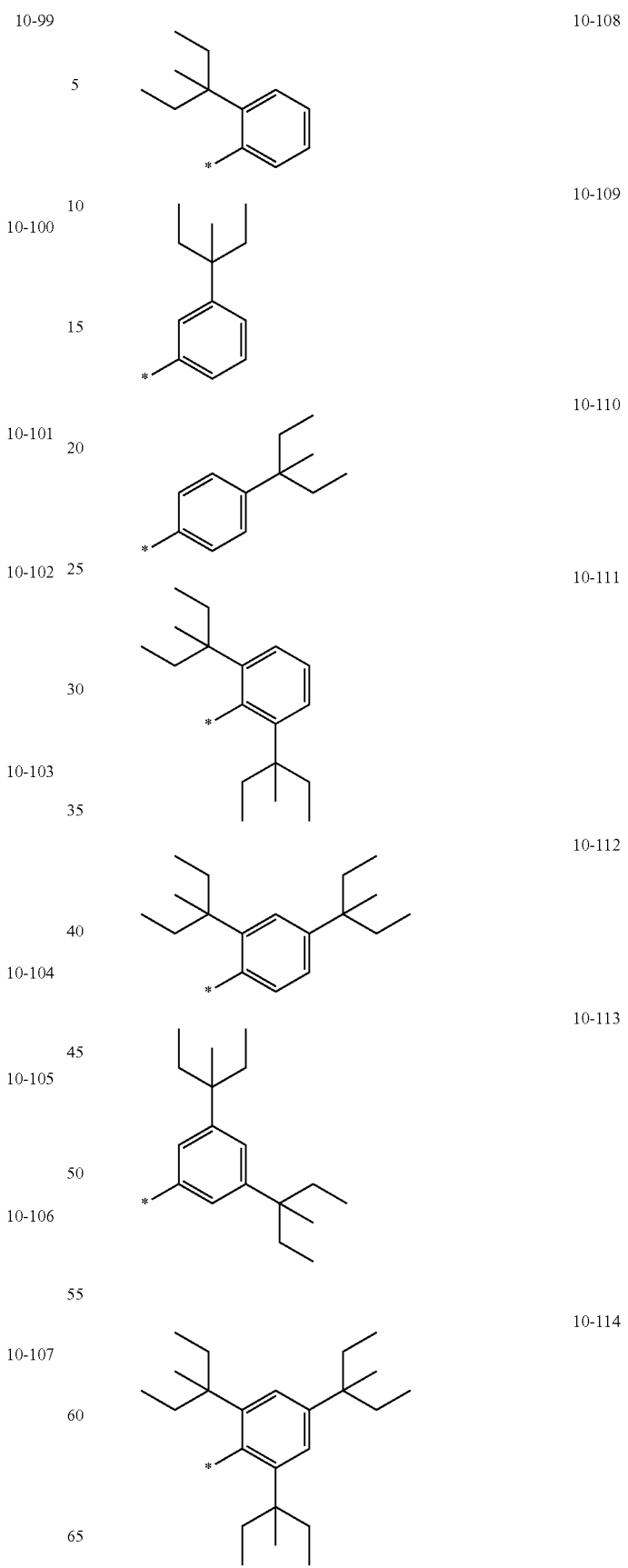

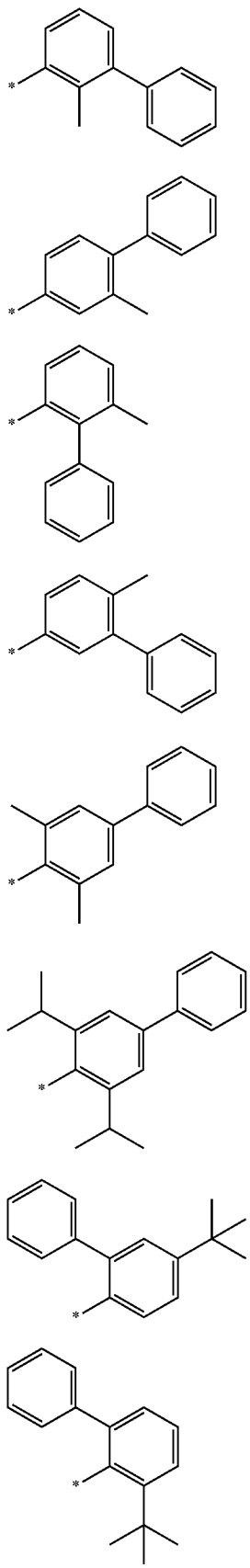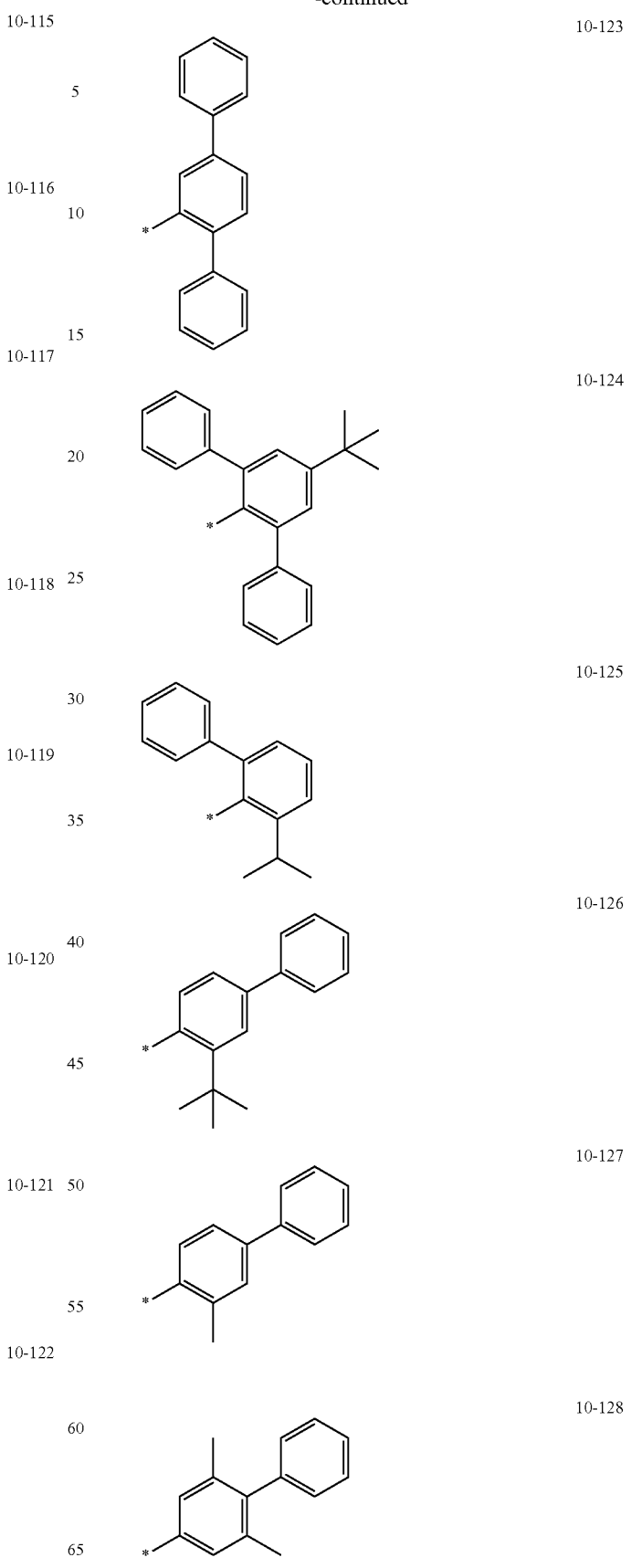

10-129
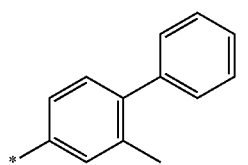
10-130
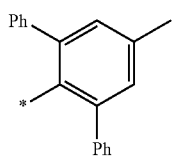
10-359
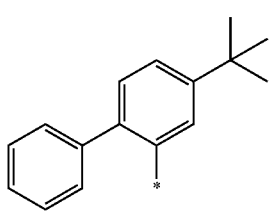
10-360
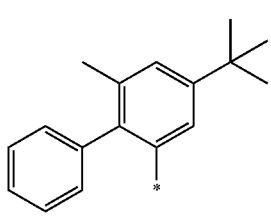
10-361
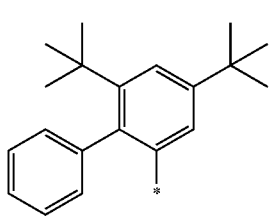
10-362
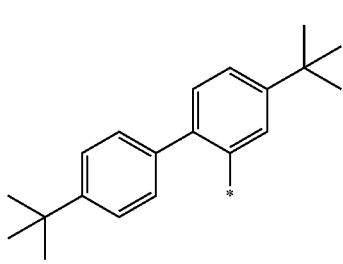
10-363
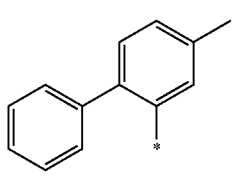
10-364
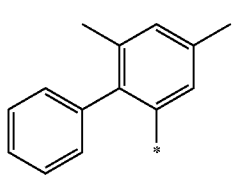
10-365
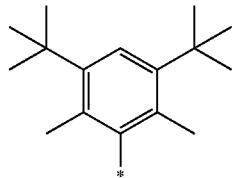
10-366
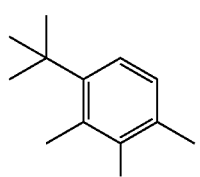
10-367
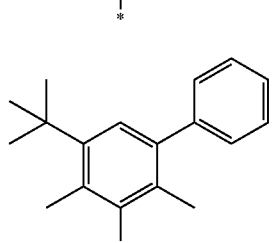
10-368
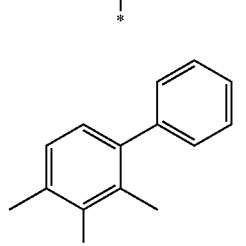
10-369
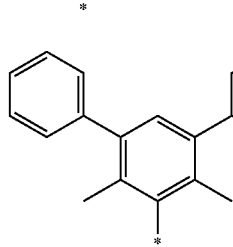
10-370
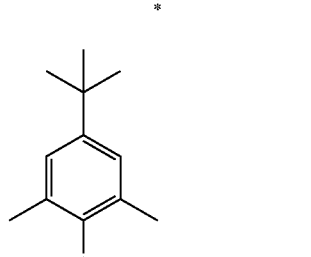
10-371
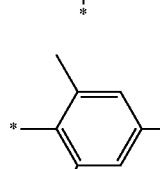
10-372
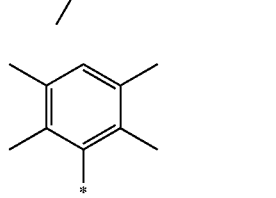

-continued 10-373 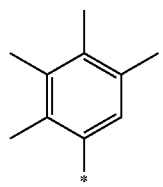

10-374 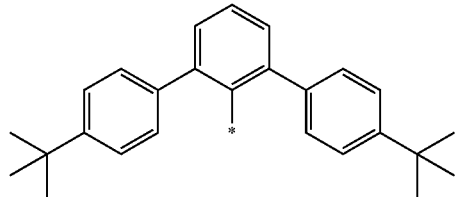

10-375 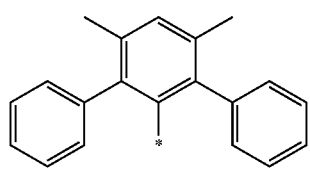

10-376 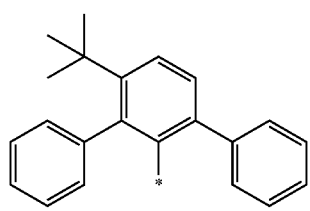

10-377 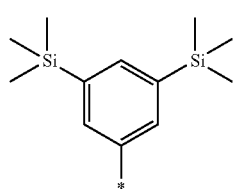

10-378 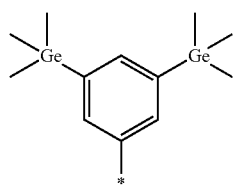

10-379 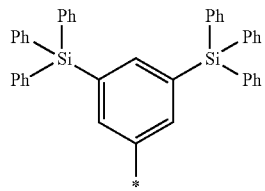

10-380 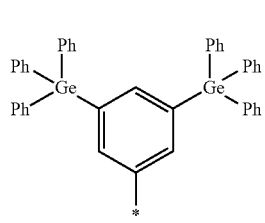

wherein, in Formulae 9-1 to 9-39, 10-12 to 10-130, and 10-359 to 10-380,

* indicates a binding site to an adjacent atom, "Ph" represents a phenyl group, "TMS" and "SiMe$_3$" each represent a trimethylsilyl group, and "TMG" and "GeMe$_3$" each represent a trimethylgermyl group.

The "group represented by Formulae 9-1 to 9-39 in which at least one hydrogen is substituted with deuterium" may be, for example, a group represented by one of Formulae 9-501 to 514:

9-501 

9-502 

9-503 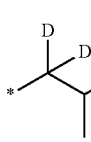

9-504 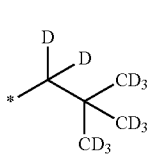

9-505 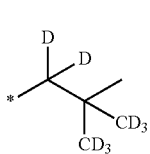

9-506 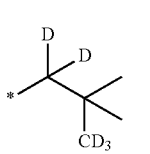

9-507 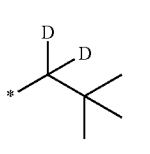

9-508 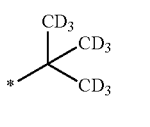

9-509 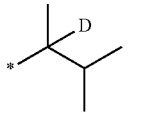

9-510 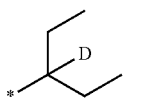

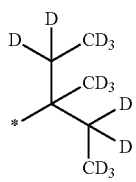
9-511
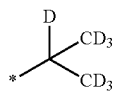
9-512
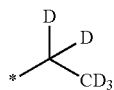
9-513
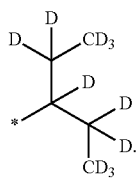
9-514
The "group represented by Formulae 9-1 to 9-39 in which at least one hydrogen is substituted with —F" may be, for example, a group represented by one of Formulae 9-701 to 710:
9-701
9-702
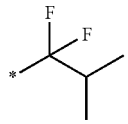
9-703
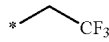
9-704
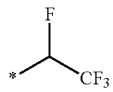
9-705
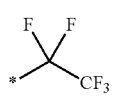
9-706
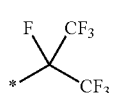
9-707
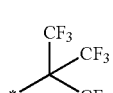
9-708
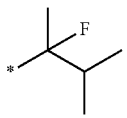
9-709
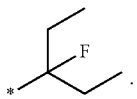
9-710
The "group represented by Formulae 10-12 to 10-130 in which at least one hydrogen is substituted with deuterium" may be, for example, a group represented by one of Formulae 10-505 to 10-576:
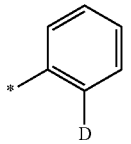
10-505
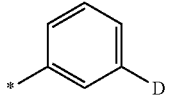
10-506
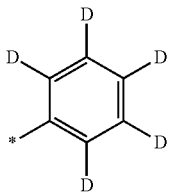
10-507
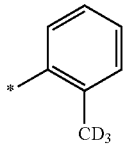
10-508
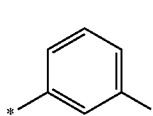
10-509
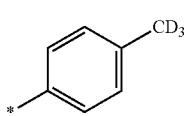
10-510
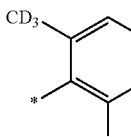
10-511
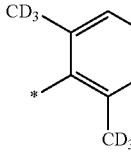
10-512

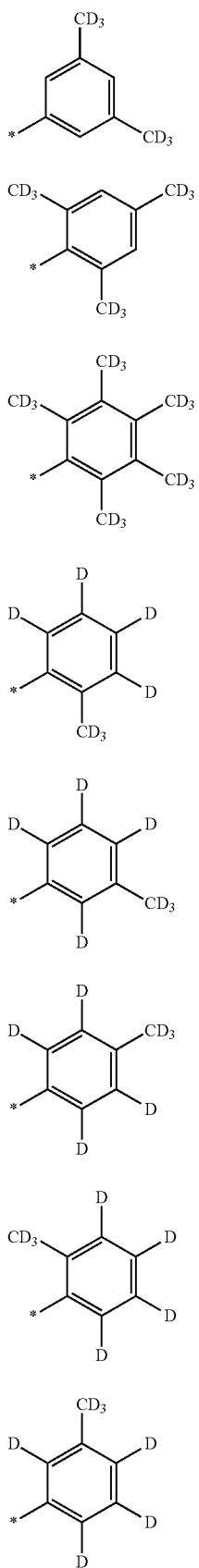
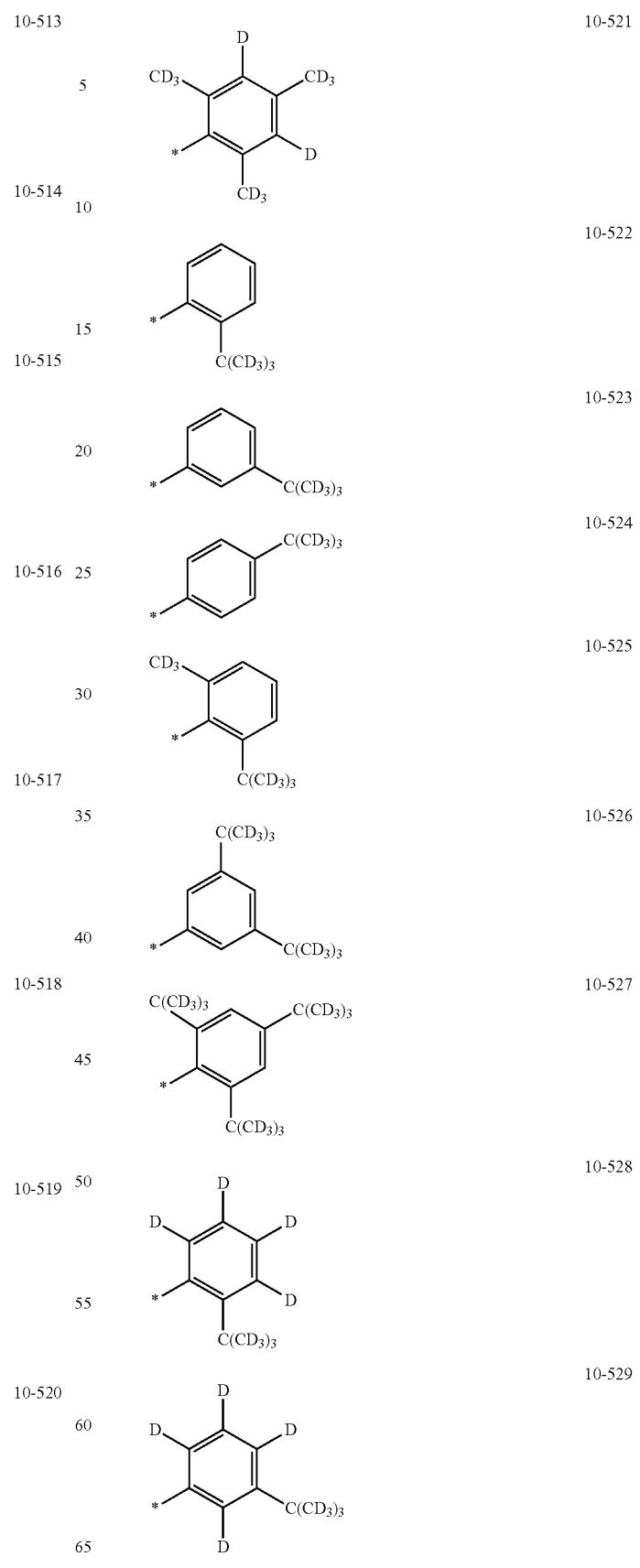

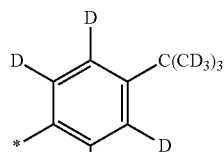
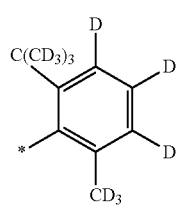
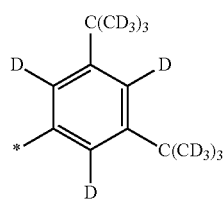
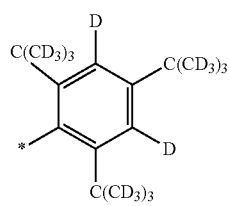
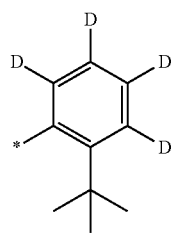
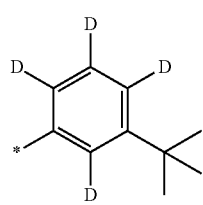
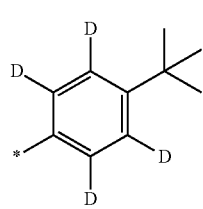
10-530
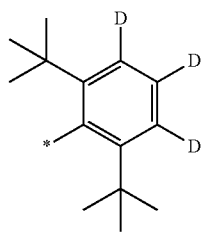
10-531
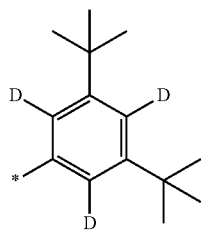
10-532
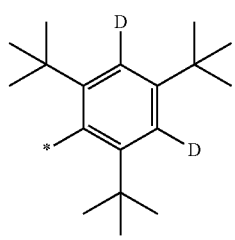
10-533
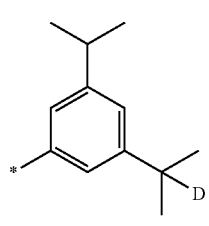
10-534
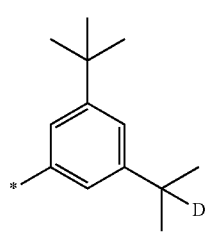
10-535
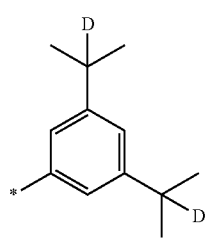
10-536
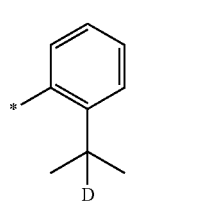
10-537
10-538
10-540
10-541
10-542
10-543
10-544

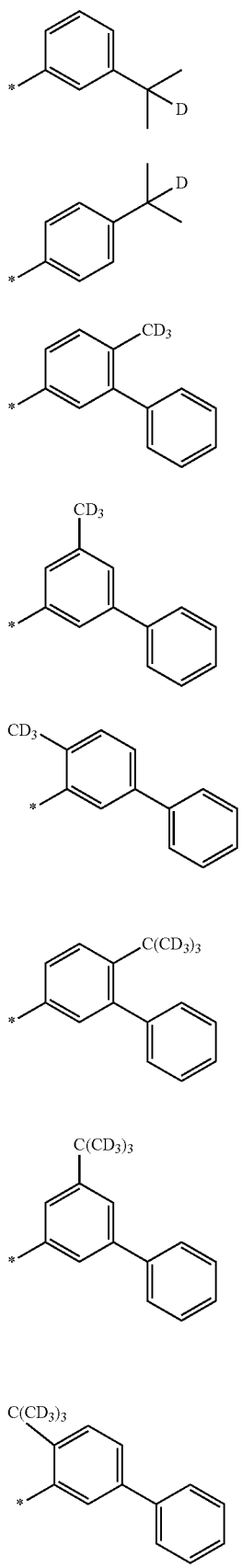
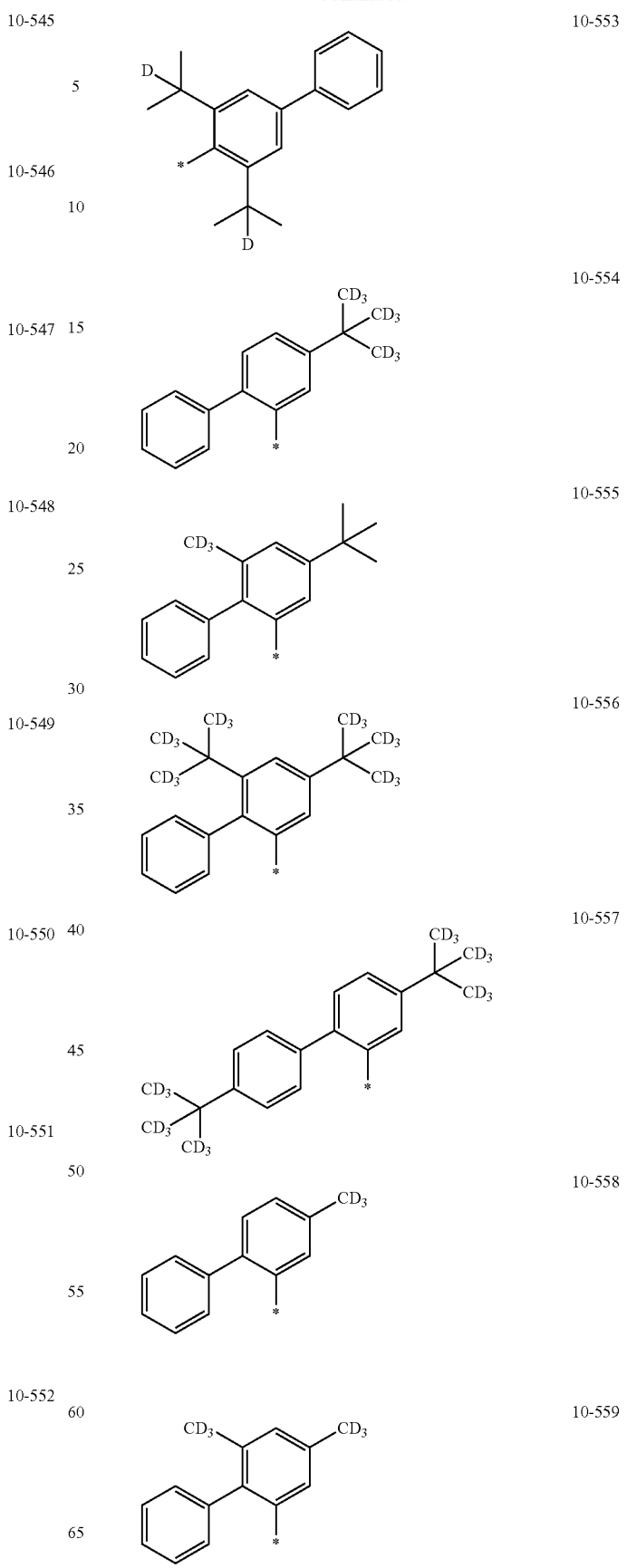

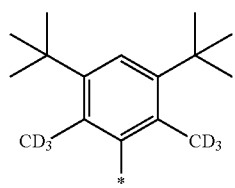
10-560
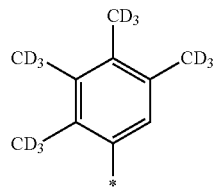
10-568
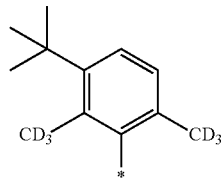
10-561
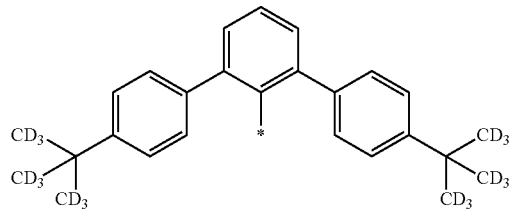
10-569
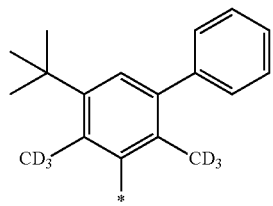
10-562
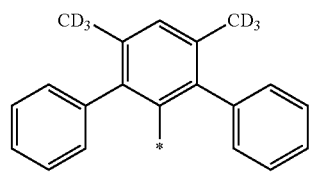
10-570
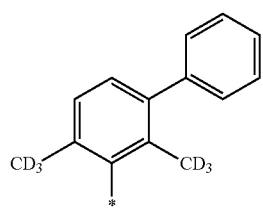
10-563
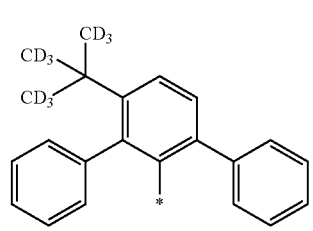
10-571
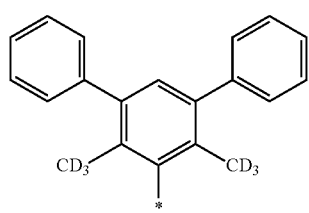
10-564
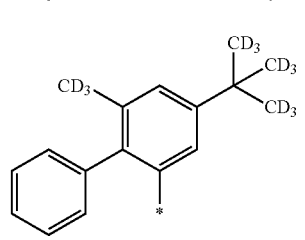
10-572
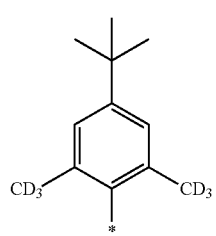
10-565
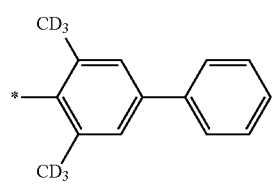
10-566
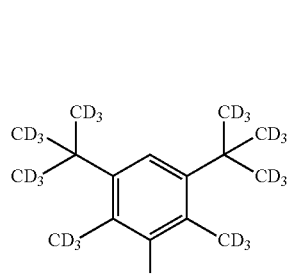
10-573
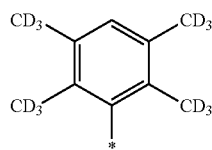
10-567
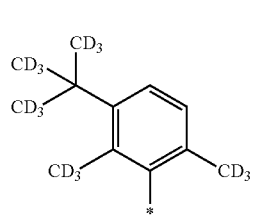
10-574

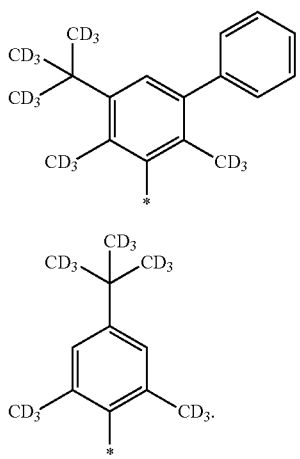

The "group represented by Formulae 10-1 to 10-130 in which at least one hydrogen is substituted with —F" may be, for example, a group represented by one of Formulae 10-601 to 10-617:

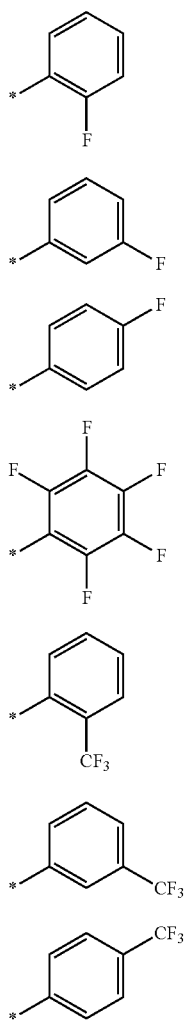

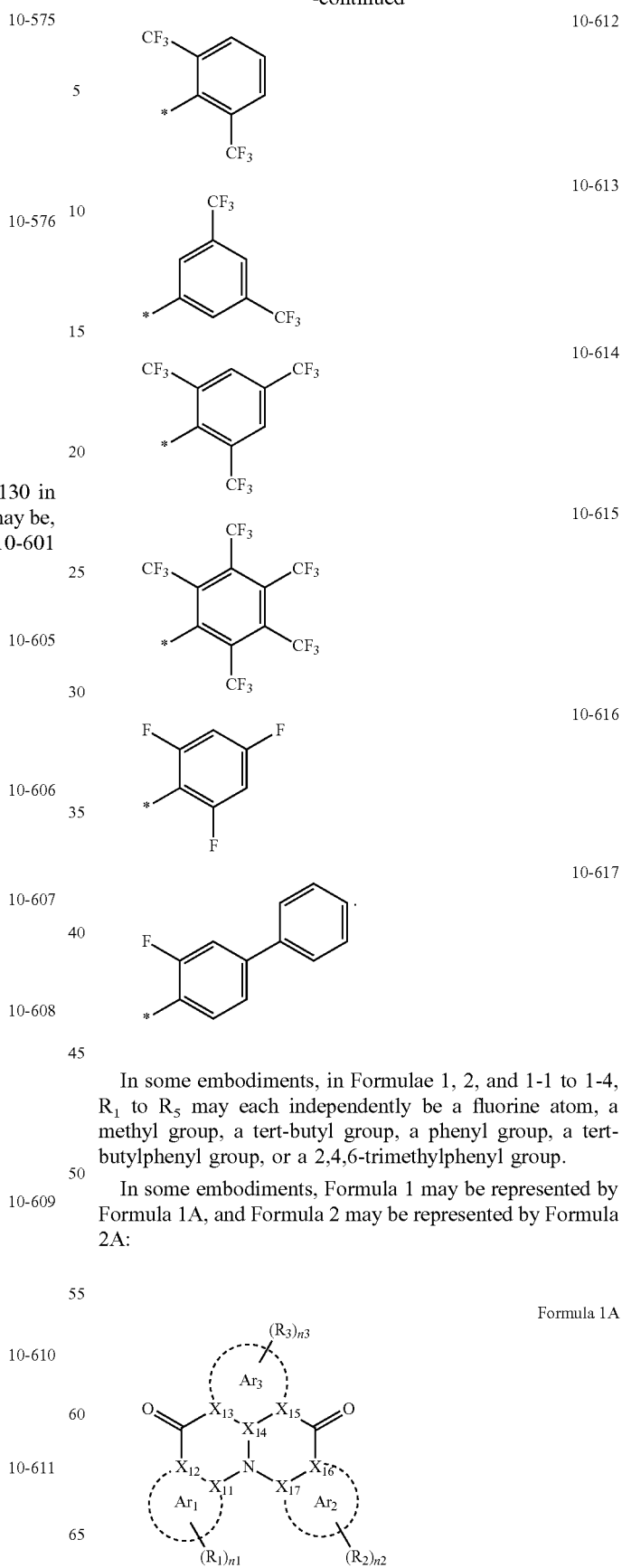

In some embodiments, in Formulae 1, 2, and 1-1 to 1-4, $R_1$ to $R_5$ may each independently be a fluorine atom, a methyl group, a tert-butyl group, a phenyl group, a tert-butylphenyl group, or a 2,4,6-trimethylphenyl group.

In some embodiments, Formula 1 may be represented by Formula 1A, and Formula 2 may be represented by Formula 2A:

-continued

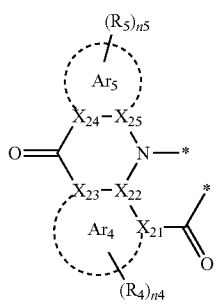

Formula 2A wherein, in Formulae 1A and 2A, $Ar_1$ to $Ar_5$, $R_1$ to $R_5$, and n1 to n5 may each be understood by referring to the descriptions of $Ar_1$ to $Ar_5$, $R_1$ to $R_5$, and n1 to n5 provided herein, in Formula 2A indicates a binding site to a ring-forming atom of $Ar_1$ in Formula 1A, a ring-forming atom of $Ar_2$ in Formula 1A, a ring-forming atom of $Ar_3$ in Formula 1A, or a combination thereof, $X_{11}$ to $X_{17}$ and $X_{21}$ to $X_{25}$ may each independently be a carbon atom, and a bond between $X_{11}$ and $X_{12}$, a bond between $X_{13}$ and $X_{14}$, a bond between $X_{14}$ and $X_{15}$, a bond between $X_{16}$ and $X_{17}$, a bond between $X_{21}$ and $X_{22}$, a bond between $X_{22}$ and $X_{23}$, and a bond between $X_{24}$ and $X_{25}$ may each independently be a single bond or a double bond.

For example, in Formulae 1A and 2A, $Ar_1$ to $Ar_5$ may each independently be a benzene ring, a naphthalene ring, an anthracene ring, a phenanthrene ring, a pyridine ring, a pyridazine ring, a pyrimidine ring, or a pyrazine ring.

In some embodiments, in Formulae 1A and 2A, $Ar_1$ to $Ar_5$ may each independently be a benzene ring, a pyridine ring, a pyridazine ring, a pyrimidine ring, or a pyrazine ring.

In some embodiments, in Formulae 1A and 2A, $Ar_1$ to $Ar_5$ may each be a benzene ring at the same time.

In Formulae 1A and 2A, when $Ar_1$ to $Ar_5$ are each independently a 6-membered ring, $Ar_1$ in Formula 1A may be represented by Formula 3-1,
$Ar_2$ in Formula 1A may be represented by Formula 3-2,
$Ar_3$ in Formula 1A may be represented by Formula 3-3,
$Ar_4$ in Formula 2A may be represented by Formula 3-4, and
$Ar_5$ in Formula 2A may be represented by Formula 3-5:

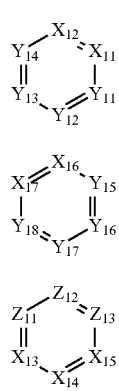

3-1

3-2

3-3

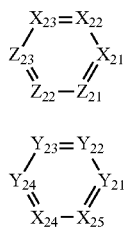

3-4

3-5 wherein, in Formulae 3-1 to 3-5, $Y_{11}$ may be $C(R_{101})$ or N, $Y_{12}$ may be $C(R_{102})$ or N, $Y_{13}$ may be $C(R_{103})$ or N, $Y_{14}$ may be $C(R_{104})$ or N, $Y_{15}$ may be $C(R_{105})$ or N, $Y_{16}$ may be $C(R_{106})$ or N, $Y_{17}$ may be $C(R_{107})$ or N, $Y_{18}$ may be $C(Rio)$ or N, $Z_{11}$ may be $C(R_{111})$ or N, $Z_{12}$ may be $C(R_{112})$ or N, $Z_{13}$ may be $C(R_{113})$ or N, $Y_{21}$ may be $C(R_{201})$ or N, $Y_{22}$ may be $C(R_{202})$ or N, $Y_{23}$ may be $C(R_{203})$ or N, $Y_{24}$ may be $C(R_{204})$ or N, $Z_{21}$ may be $C(R_{211})$ or N, $Z_{22}$ may be $C(R_{212})$ or N, and $Z_{23}$ may be $C(R_{213})$ or N,

* in Formula 2A indicates a bond to two selected from $Y_{11}$ to $Y_{18}$ and $Z_{11}$ to $Z_{13}$ in Formula 1A, and $R_{101}$ to $R_{111}$, $R_{111}$ to $R_{113}$, $R_{201}$ to $R_{204}$, and $R_{211}$ to $R_{21}$ may each be a binding site to * in Formula 2A, a deuterium atom, a halogen atom, a substituted or unsubstituted alkyl group, a substituted or unsubstituted haloalkyl group, a substituted or unsubstituted halocycloalkyl group, a substituted or unsubstituted alkoxy group, a substituted or unsubstituted cycloalkoxy group, a substituted or unsubstituted alkylthio group, a substituted or unsubstituted cycloalkylthio group, a substituted or unsubstituted aryl group, a substituted or unsubstituted heteroaryl group, a substituted or unsubstituted aryloxy group, a substituted or unsubstituted heteroaryloxy group, a substituted or unsubstituted arylthio group, a substituted or unsubstituted heteroarylthio group, or a substituted or unsubstituted amino group.

In some embodiments, in Formulae 3-1 to 3-5, $X_{11}$ to $X_{17}$, $X_{21}$ to $X_{25}$, $Y_{11}$ to $Y_{18}$, $Y_{21}$ to $Y_{24}$, $Z_{11}$ to $Z_{13}$, and $Z_{21}$ to $Z_{23}$ may each independently be a carbon atom.

In some embodiments, the heterocyclic compound represented by Formula 1 and Formula 2 may be represented by one of Formulae 1-11 to 1-13, 1-21 to 1-23, 1-31, and 1-41:

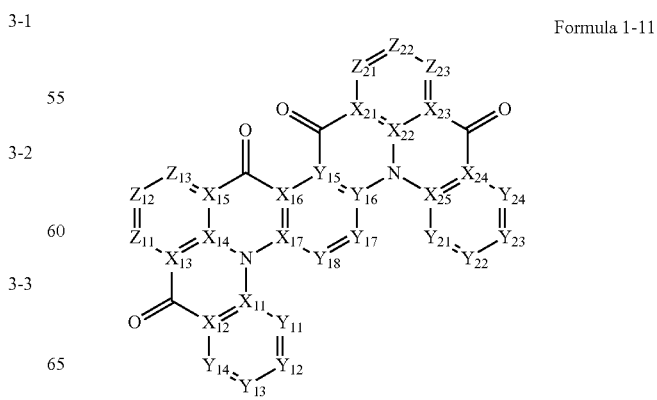

Formula 1-11

Formula 1-12
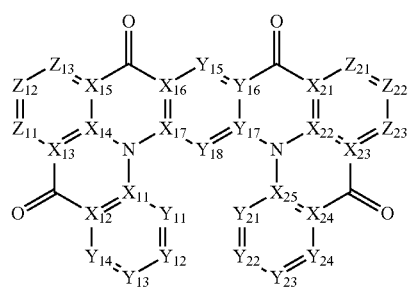

Formula 1-13
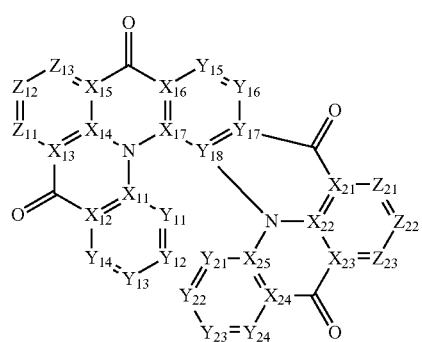

Formula 1-21
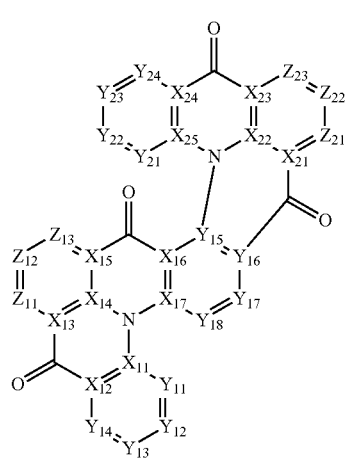

Formula 1-22
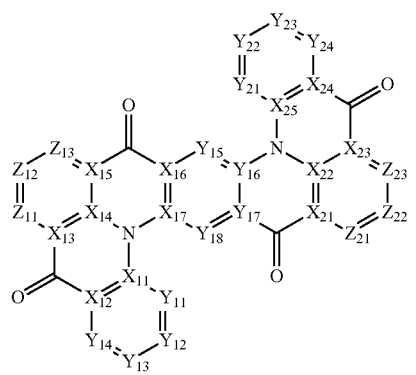

Formula 1-23
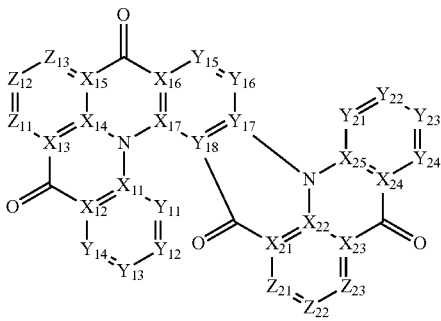

Formula 1-31
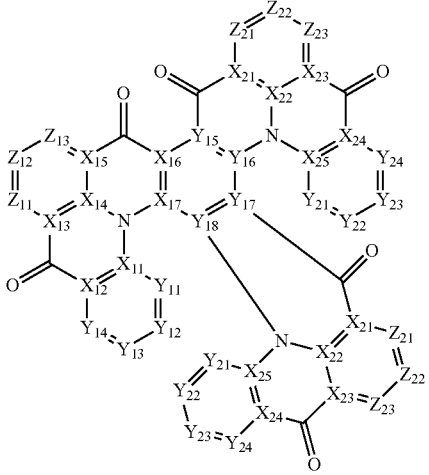

Formula 1-41
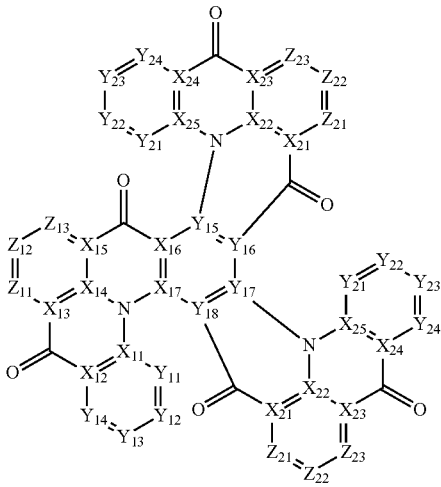

wherein, in Formulae 1-11 to 1-13, 1-21 to 1-23, 1-31, and 1-41, $Y_{11}$ may be $C(R_{101})$ or N, $Y_{12}$ may be $C(R_{102})$ or N, $Y_{13}$ may be $C(R_{103})$ or N, $Y_{14}$ may be $C(R_{104})$ or N, $Y_{15}$ may be $C(R_{105})$ or N, $Y_{16}$ may be $C(R_{106})$ or N, $Y_{17}$ may be $C(R_{107})$ or N, $Y_{18}$ may be $C(R_{108})$ or N, $Z_{11}$ may be $C(R_{111})$ or N, $Z_{12}$ may be $C(R_{112})$ or N, $Z_{13}$ may be $C(R_{113})$ or N, $Y_{21}$ may be $C(R_{201})$ or N, $Y_{22}$ may be $C(R_{202})$ or N, $Y_{23}$ may be $C(R_{203})$ or N, $Y_{24}$ may be $C(R_{204})$ or N, $Z_{21}$ may be $C(R_{211})$ or N, $Z_{22}$ may be $C(R_{212})$ or N, and $Z_{23}$ may be $C(R_{213})$ or N, and $R_{101}$ to $R_{108}$, $R_{111}$ to $R_{113}$, $R_{201}$ to $R_{204}$, and $R_{211}$ to $R_{21}$ may each be understood by referring to the description of $R_1$ provided herein.
In some embodiments, the heterocyclic compound may be selected from Compounds 1 to 27, but embodiments are not limited thereto:
1
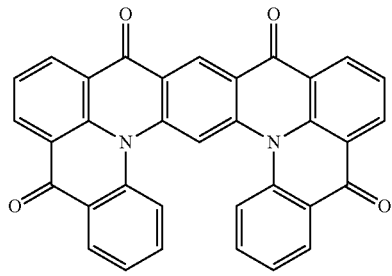
2
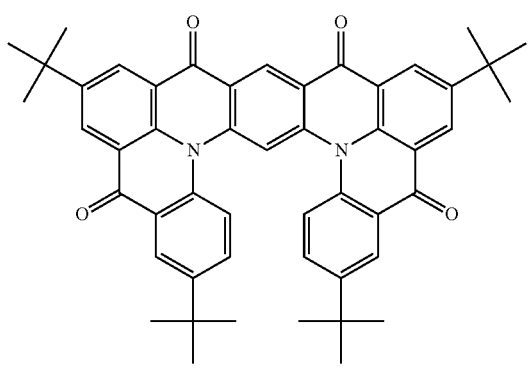
3
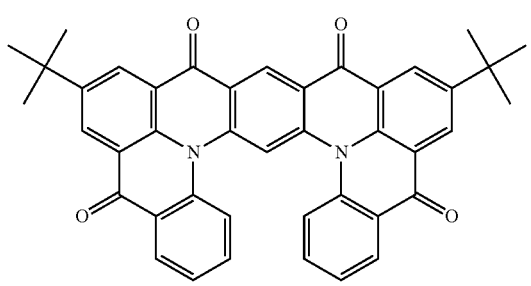
4
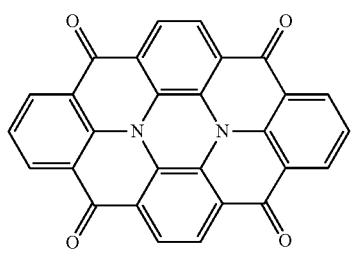
5
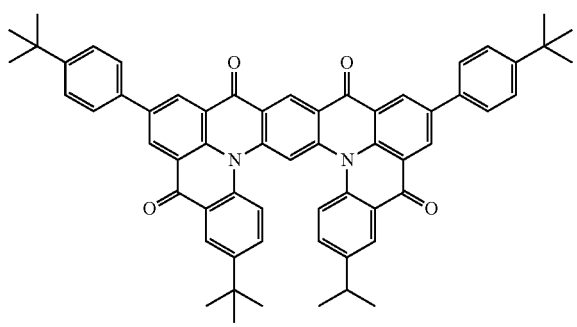
6
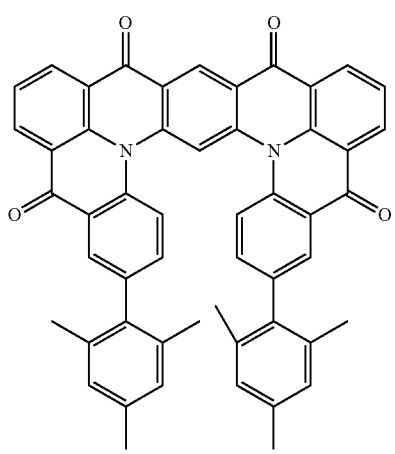
7
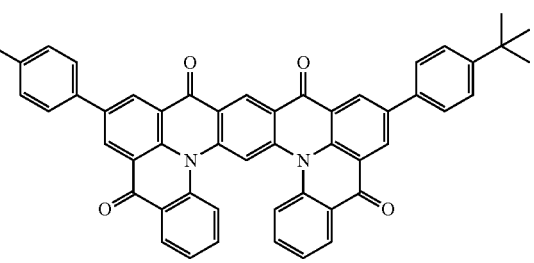
8
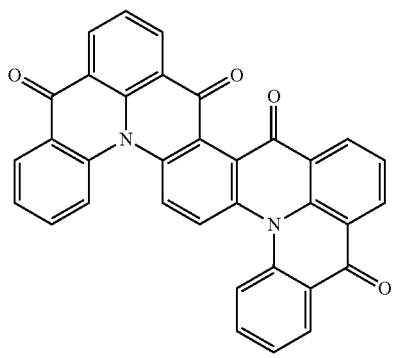

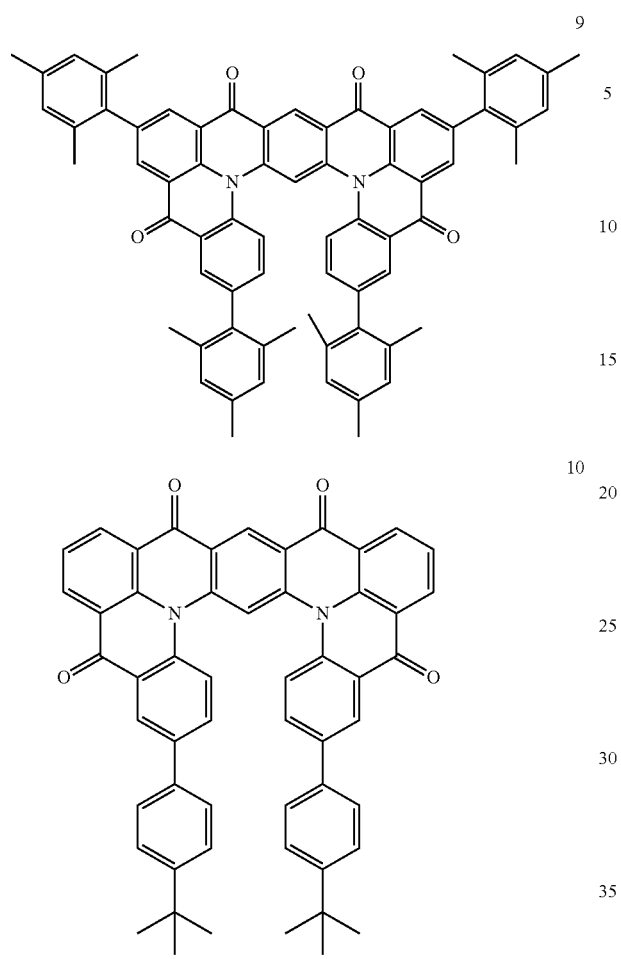
9
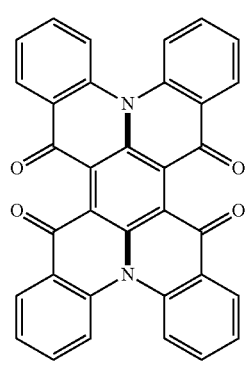
10
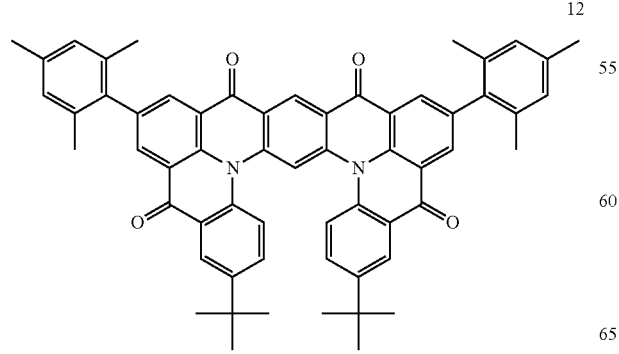
11
12
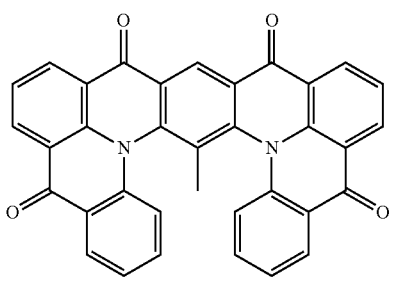
13
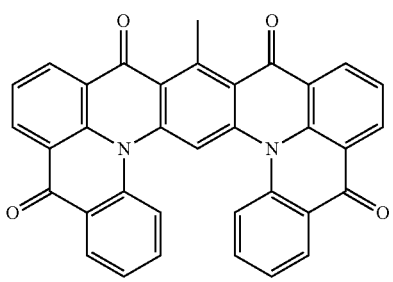
14
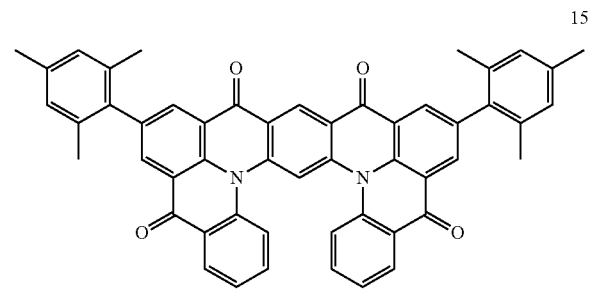
15
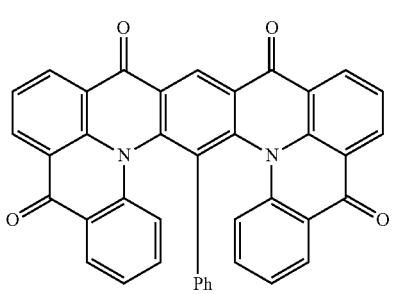
16
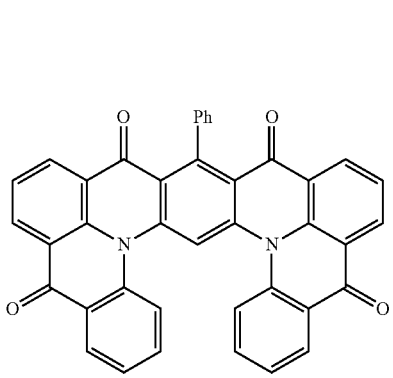
17

18
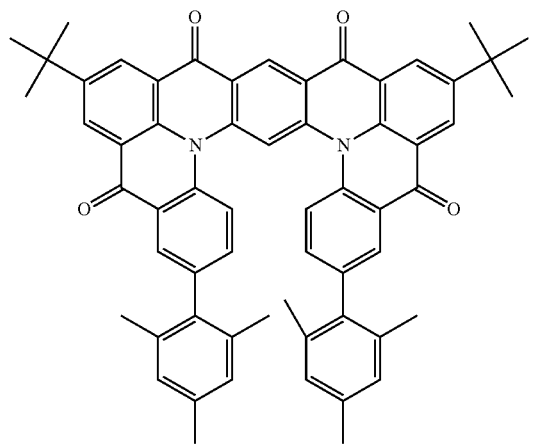
19
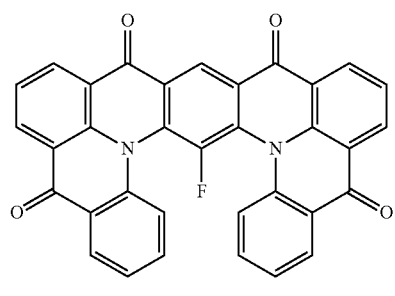
20
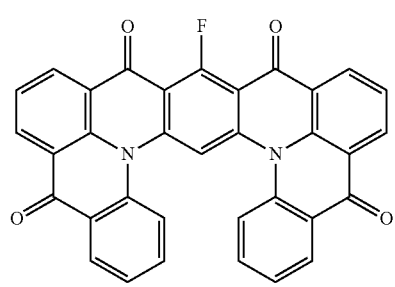
21
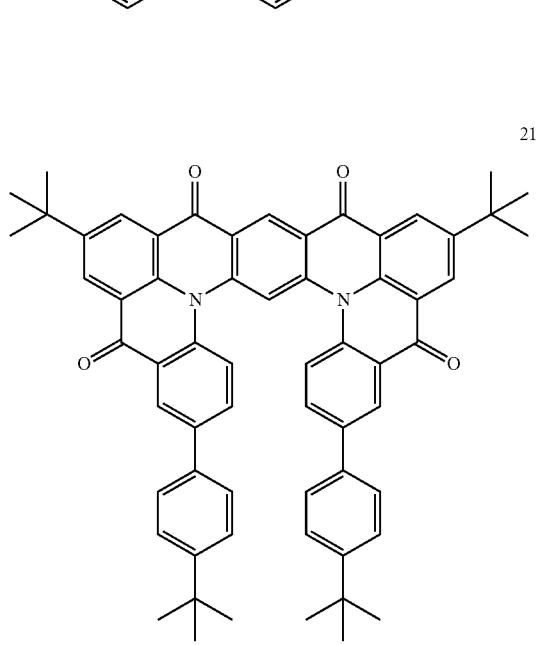
22
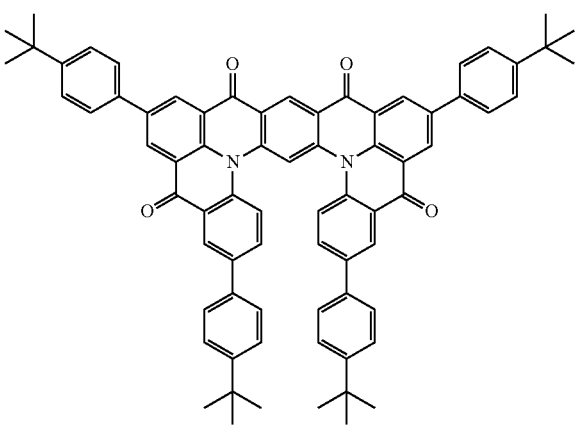
23
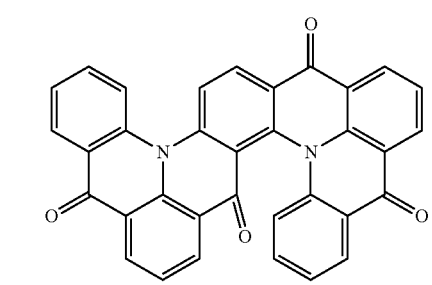
24
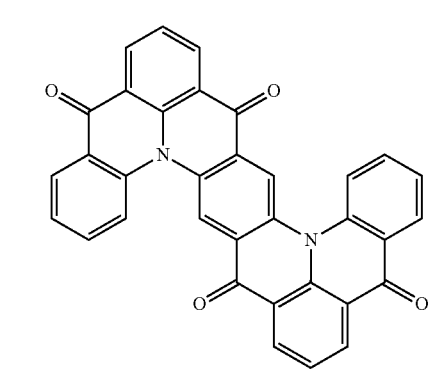
25
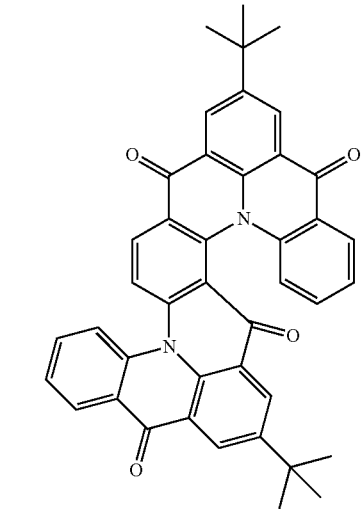

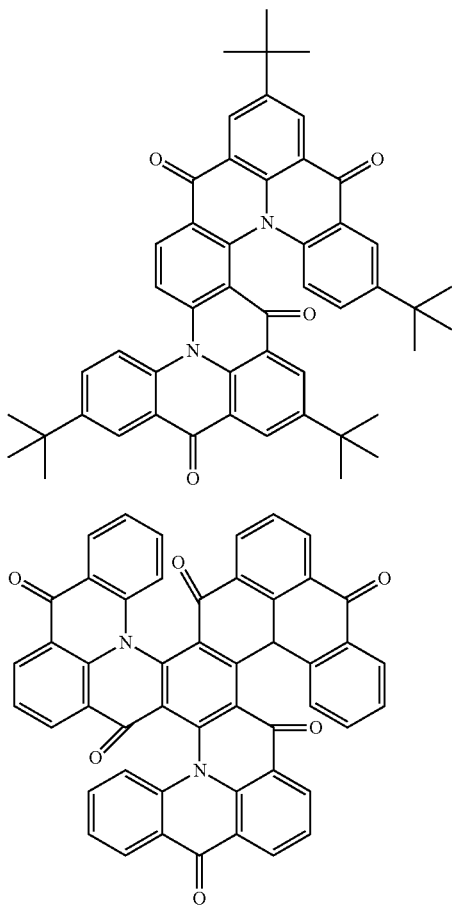

wherein, "Ph" in Compounds 16 and 17 represents an unsubstituted phenyl group.

In some embodiments, the heterocyclic compound may be selected from Compounds 1 to 3.

Various compounds are being considered as light-emitting materials used in organic light-emitting devices. In particular, as a blue light-emitting material, a heterocyclic compound containing a heteroatom is being considered. In addition, from the viewpoint of improving efficiency of organic light-emitting devices using not only singlet excitons but also using triplet excitons, research on materials emitting delayed fluorescence has been recently conducted.

In general, compounds having a relatively small $\Delta E_{ST}$ value may emit thermal activated delayed fluorescence (TADF). However, even though the $\Delta E_{ST}$ value of the heterocyclic compound is relatively large, the the heterocyclic compound may satisfy Conditions 1 to 4, the heterocyclic compound may emit TADF, and an organic light-emitting device including the heterocyclic compound may have improved efficiency:

$\Delta E_{ST} > \Delta E_{ST2} + \Delta E'_{TT}$  Condition 1

$0\ eV < \Delta E_{ST2} + \Delta E'_{TT} \leq 1.0\ eV$  Condition 2

$0\ eV < \Delta E'_{TT} \leq 0.15\ eV$  Condition 3

$\Delta E_{ST2} > 0\ eV$  Condition 4 wherein, in Conditions 1 to 4, $\Delta E_{ST}$ indicates a difference between a lowest excited singlet energy level calculated in an $S_1$ equilibrium structure of the heterocyclic compound and a lowest excited triplet energy level calculated in a $T_1$ equilibrium structure of the heterocyclic compound, $\Delta E_{ST2}$ indicates a difference between a lowest excited singlet energy level calculated in an $S_1$ equilibrium structure of the heterocyclic compound and a second lowest excited triplet energy level calculated in a $T_2$ equilibrium structure of the heterocyclic compound, and $\Delta E'_{TT}$ indicates a difference between a second lowest excited triplet energy level calculated in an $T_2$ equilibrium structure of the heterocyclic compound and a lowest excited triplet energy level calculated in a $T_2$ equilibrium structure of the heterocyclic compound.

Furthermore, by using the heterocyclic compound as a sensitizer, energy transferred to a triplet state may undergo reverse inter system crossing (RISC) to a singlet state. Then, the singlet energy of the heterocyclic compound may be transferred to a dopant by Förster energy transfer. Thus, the organic light-emitting device may have improved efficiency and lifespan at the same time.

In some embodiments, the heterocyclic compound may satisfy Condition 5:

$\Delta E_{ST2} \leq 0.1\ eV$  Condition 5 wherein, in Condition 5, $\Delta E_{ST2}$ indicates a difference between a lowest excited singlet energy level calculated in an Si equilibrium structure of the heterocyclic compound and a second lowest excited triplet energy level calculated in a $T_2$ equilibrium structure of the heterocyclic compound.

In some embodiments, the heterocyclic compound may satisfy Condition 6:

$\Delta E_{ST} > 0.2\ eV$  Condition 6 wherein, in Condition 6, $\Delta E_{ST}$ indicates a difference between a lowest excited singlet energy level calculated in an $S_1$ equilibrium structure of the heterocyclic compound and a lowest excited triplet energy level calculated in a $T_1$ equilibrium structure of the heterocyclic compound.

That is, the heterocyclic compound according to one or more embodiments may emit TADF even when $\Delta E_{ST}$ is greater than 0.2 eV.

Since the heterocyclic compound has a rigid structure in which aromatic hydrocarbon rings or heteroaromatic rings are condensed, structural relaxation in an excited state may be suppressed. As a result, the heterocyclic compound may have a narrow width of blue emission spectrum and improved colorimetric purity.

The highest occupied molecular orbital (HOMO) level of the heterocyclic compound according to one or more embodiments is not particularly limited and may be about −6.5 eV or higher, or for example, about −6.3 eV or higher. When the LUMO level is within this range, the organic light-emitting device may have a low driving voltage. In addition, the HOMO level of the heterocyclic compound according to an embodiment may be about −5.0 eV or lower from the viewpoint of consistency with an energy diagram of other general materials forming the emission layer and the stability in the atmosphere.

The lowest unoccupied molecular orbital (LUMO) level of the heterocyclic compound according to one or more embodiments is not particularly limited and may be about −2.5 eV or lower, or for example, about −2.6 eV or lower.

When the LUMO level is within this range, the organic light-emitting device may have a low driving voltage. In addition, the LUMO level of the heterocyclic compound according to an embodiment may be about −4.0 eV or higher from the viewpoint of consistency with an energy diagram of other general materials forming the emission layer.

The HOMO level may be measured and/or calculated using an atmospheric photoelectron spectrometer, and the LUMO level may be measured and/or calculated using an atmospheric photoelectron spectrometer and a spectrophotometer, respectively. The measurement and/or calculation methods are described in the Examples.

The peak wavelength in photoluminescence (PL) of the heterocyclic compound according to an embodiment is not particularly limited and may be about 430 nanometers (nm) or greater. In some embodiments, the peak wavelength may be about 435 nm or greater, about 440 nm or greater, about 500 nm or greater, about 490 nm or greater, or about 480 nm or greater. When the peak wavelength is within any of these ranges, the heterocyclic compound according to an embodiment may be more suitable for blue light emission.

The heterocyclic compound according to one or more embodiments may have a small the full width at half maximum (FWHM) of an emission intensity of a peak having a PL peak wavelength. In some embodiments, FWHM may be about 45 nm or less, about 40 nm or less, or about 35 nm or less. When the FWHM is within any of these ranges, the heterocyclic compound according to an embodiment may have more improved colorimetric purity.

The peak wavelength at PL and the FWHM at PL may be measured and/or calculated using a spectrofluorophotometer. The measurement and/or calculation methods are described in the Examples.

$\Delta E_{ST}$ of the heterocyclic compound according to one or more embodiments is a value obtained by subtracting a triplet energy (T1) of a phosphorescence spectrum from a singlet energy (S1) of a fluorescence spectrum. Singlet energy S1, triplet energy T1, and $\Delta E_{ST}$ may be measured and/or calculated by measuring a fluorescence spectrum and a phosphorescence spectrum at 77 K using a spectrofluorescence photometer. The measurement and/or calculation methods are described in the Examples.

The synthetic methods of the heterocyclic compound according to one or more embodiments is not particularly limited and may be synthesized according to a known synthesis method. In particular, it may be synthesized according to or in view of the method described in the Examples. For example, in the method described in the Examples, the heterocyclic compound according to one or more embodiments may be synthesized through modifications such as changing raw materials and reaction conditions, adding or excluding some processes, or appropriately combining with other known synthesis methods.

The method of identifying a structure of the heterocyclic compound according to one or more embodiments is not particularly limited. The heterocyclic compound containing nitrogen according to one or more embodiments may be identified by a known method, for example, NMR or LC-MS.

Figure 2:
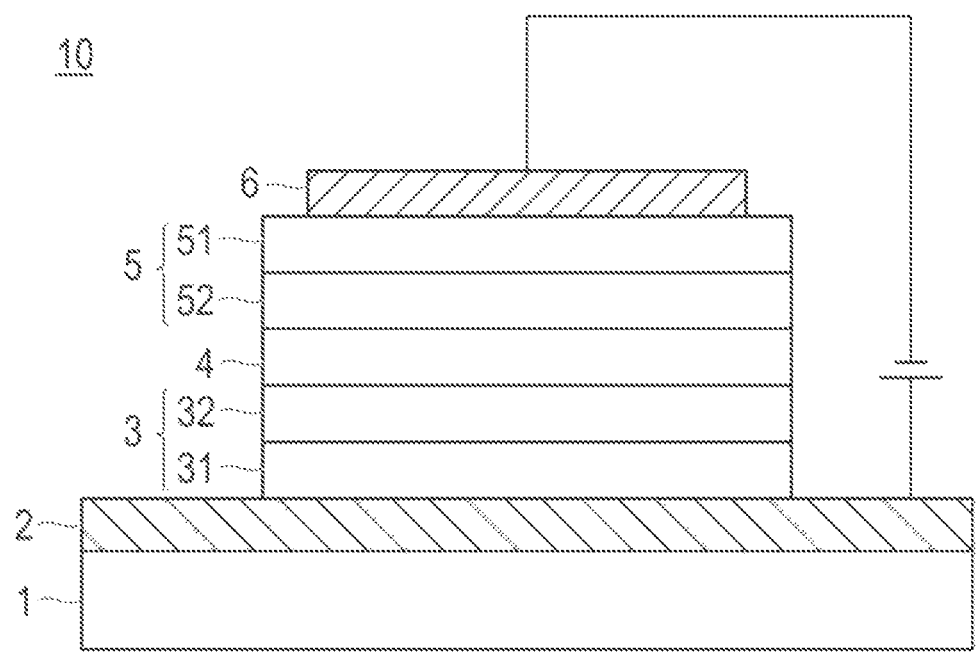
FIG. 2 is a schematic cross-sectional view illustrating an organic light-emitting device according to another exemplary embodiment.
Figure 3:
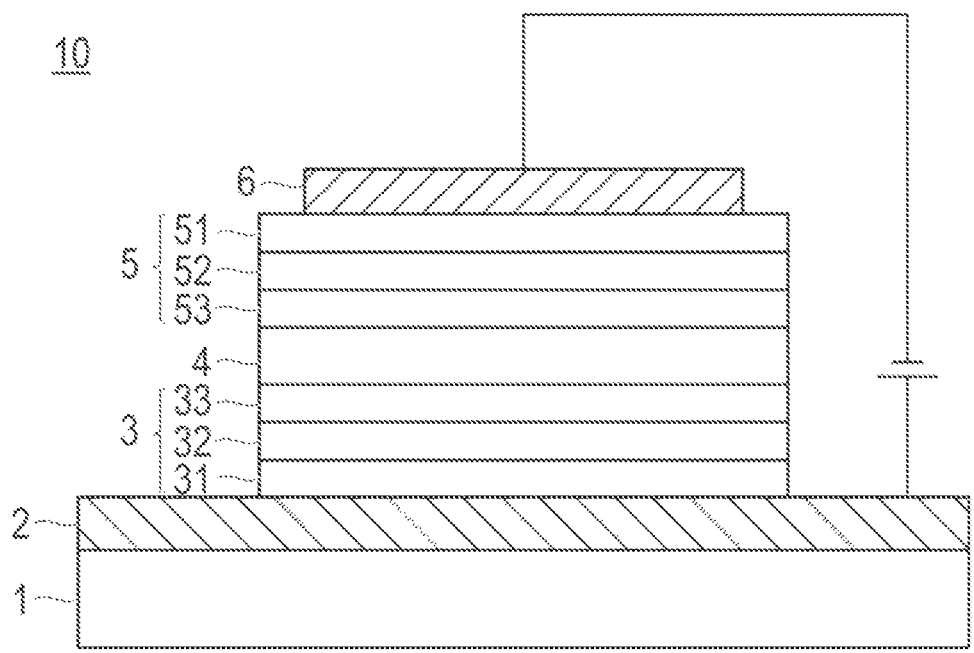
FIG. 3 is a schematic cross-sectional view illustrating an organic light-emitting device according to still another exemplary embodiment.

Descriptions of FIGS. 1 to 3

Hereinafter, with reference to FIGS. 1 to 3, an embodiment of an organic light-emitting device 10 will be described in detail.

FIG. 1 is a schematic view of an organic light-emitting device according to an exemplary embodiment. The organic light-emitting device 10 according to an embodiment may include a substrate 1, a first electrode 2, a hole transport region 3, an emission layer 4, an electron transport region 5, and a second electrode 6, which are sequentially layered in the stated order.

FIG. 2 is a schematic view of an organic light-emitting device according to another exemplary embodiment. The organic light-emitting device 10 according to an embodiment may include the substrate 1, the first electrode 2, the hole transport region 3, the emission layer 4, the electron transport region 5, and the second electrode 6. As shown in FIG. 2, the hole transport region 3 may include a hole injection layer 31 and a hole transport layer 32, which are sequentially layered in the stated order. In addition, as shown in FIG. 2, the electron transport region 5 may include an electron transport layer 52 and an electron injection layer 51, which are sequentially layered in the stated order.

FIG. 3 is a schematic view of an organic light-emitting device according to still another exemplary embodiment. The organic light-emitting device 10 according to an embodiment may include the substrate 1, the first electrode 2, the hole transport region 3, the emission layer 4, the electron transport region 5, and the second electrode 6. As shown in FIG. 3, the hole transport region 3 may include the hole injection layer 31, the hole transport layer 32, and an electron blocking layer 33, which are sequentially layered in the stated order. In addition, as shown in FIG. 3, the electron transport region 5 may include a hole blocking layer 53, the electron transport layer 52, and the electron injection layer 51, which are sequentially layered in the stated order.

$Ar_1$ embodiment may include, for example, an organic electroluminescence device including a first electrode, a second electrode, and a single or a plurality of emission layers. The second electrode may be one the first electrode.

In the present specification, "on" may not apply only to a case of "just on" another part and may also include a case where another part may be present therebetween. Similarly, when a part such as a layer, a membrane, a regions, a plate, or the like is described as being "below" or "under" another part, a case of "just under" another part and also a case where another part present therebetween may be included.

In the present specification, "arrangement" may include a case where a portion is arranged not only on an upper part but also on a lower part.

The organic light-emitting device 10 may include the heterocyclic compound according to one or more embodiments. For example, the heterocyclic compound according to one or more embodiments may be included in an organic layer between the first electrode 2 and the second electrode 6. In some embodiments, the heterocyclic compound may be included in the emission layer 4.

$Ar_1$ embodiment in which the emission layer includes the heterocyclic compound according to one or more embodiments will be described below.

Emission Layer 4

The emission layer 4 may emit light by fluorescence or phosphorescence.

The emission layer 4 may be a single layer including a single material or a single layer including a plurality of different materials. In addition, the emission layer 4 may have a multilayer structure having multiple layers including a single material or a plurality of different materials.

In the emission layer 4, the heterocyclic compound may be used alone or two or more thereof may be combined.

In some embodiments, the emission layer 4 may further include a host, the host and the heterocyclic compound may be different from each other, and the emission layer 4 may include the host and the heterocyclic compound. The host may not emit light, and the heterocyclic compound may emit light. That is, the heterocyclic compound may be a dopant.

In some embodiments, the emission layer 4 may further include a host and a dopant, wherein the host, the dopant, and the heterocyclic compound may be different from one another, and the emission layer 4 may include the host, the dopant, and the heterocyclic compound. In this embodiment, the host and the heterocyclic compound may not each emit light, and the dopant may emit light.

In the Examples, the host and the dopant will be described in more detail.

The emission layer 4 may include a known host material and a known dopant material.

For example, the host may include at least one of bis[2-(diphenylphosphino)phenyl]etheroxide (DPEPO), 4,4'-bis(carbazole-9-yl)biphenyl(4,4'-bis(carbazol-9-yl)biphenyl (CBP), 3,3'-bis(carbazol-9-yl)biphenyl (mCBP), 1,3-bis(carbazol-9-yl)benzene (mCP), 2,8-bis(diphenylphosphoryl) dibenzo[b,d]furan (PPF), 4,4',4''-tris(N-carbazolyl)triphenylamine (TCTA), 1,3,5-tris(N-phenyl-benzimidazol-2-yl)benzene (TPBi), tris(8-quinolinato)aluminium ($Alq_3$), poly(n-vinylcarbazole) (PVK), 9,10-di(naphthalene)anthracene (ADN), 3-tert-butyl-9,10-di(naphth-2-yl)anthracene (TBADN), distyrylarylene (DSA), 4,4'-bis(9-carbazole)-2,2'-dimethyl-biphenyl (dmCBP), 4,5'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenyl cyclotrisiloxane ($DPSiO_3$), octaphenyl cyclotetrasiloxane ($DPSiO_4$), and 2,8-bis(diphenylphosphoryl)dibenzofuran (PPF), or any combination thereof.

For example, the dopant may include a styryl derivative (e.g., 1,4-bis[2-(3-N-ethylcarbazolyl)vinyl]benzene (BCzVB), 4-(di-p-tolylamino)-4'-[(di-p-tolylamino)styryl] stylbene (DPAVB), N-(4-((E)-2-(6-((E)-4-(diphenylamino) styryl)naphthalen-2-yl)vinyl)phenyl)-N-phenylbenzene amine (N-BDAVBi)), perylene, or a derivative thereof (e.g., 2,5,8,11-tetra-tert-butylperylene (TBP)), pyrene or a derivative thereof (e.g., 1,1-dipyrene,1,4-dipyrenylbenzene or 1,4-bis(N,N-diphenylamino)pyrene), rubrene or a derivative thereof, coumarin and a derivative thereof, 4-dicyanomethylene-2-(p-dimethylaminostyryl)-6-methyl-4H-pyran (DCM) or a derivative thereof, an iridium complex such as bis[2-(4,6-difluorophenyl)pyridinate] picolinate iridium (III) (FIrpic), bis(1-phenylisoquinoline)(acetylacetonate)iridium(III) ($Ir(piq)_2(acac)$), tris(2-phenylpyridine)iridium (III) ($Ir(ppy)_3$), or tris(2-(3-p-xylyl)phenyl)pyridine iridium (III) (dopant), an osmium complex, or a platinum complex, but embodiments are not limited thereto.

When the emission layer includes the host and the dopant, an amount of the dopant may be selected from a range of about 0.01 parts to about 15 parts by weight based on about 100 parts by weight of the host, but embodiments are not limited thereto.

The thickness of the emission layer is not particularly limited and may be in a range about 1 nm to about 100 nm, or for example, about 10 nm to about 70 nm.

The emission wavelength of the organic light-emitting device is not particularly limited. However, the organic light-emitting device may emit light having a peak in a wavelength region of about 430 nm or greater and about 500 nm or less, about 435 nm or greater to about 490 nm or less, or about 440 nm or greater to about 480 nm or less.

The FWHM of an emission spectrum of the organic light-emitting device may be about 45 nm or less, about 40 nm or less, about 35 nm or less, or about 0 nm or greater.

Figure 4A:
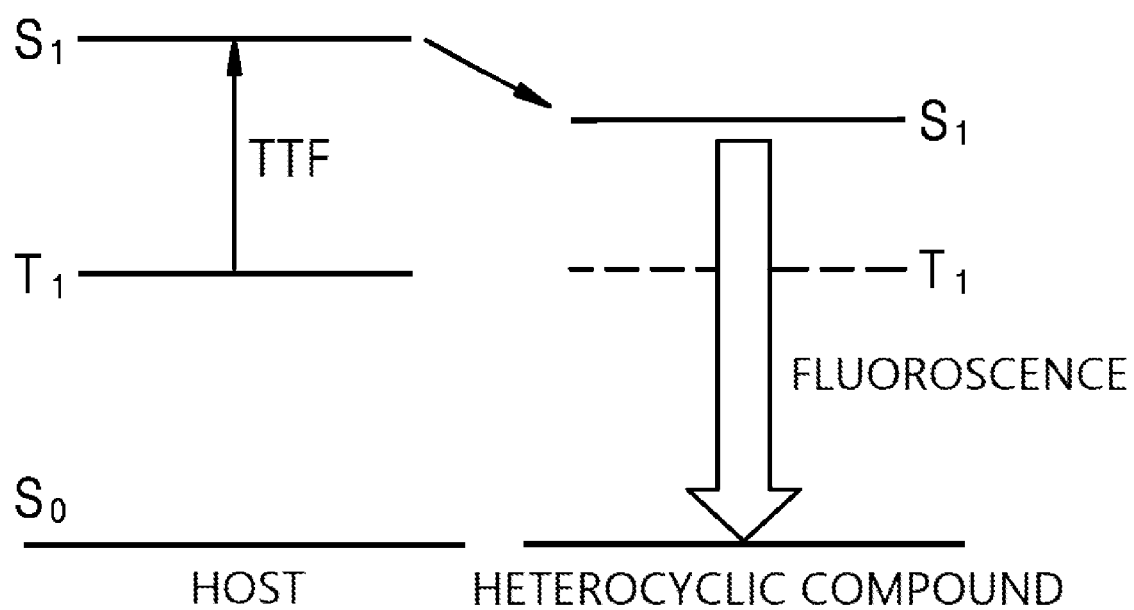
FIGS. 4A to 4E are each a schematic diagram illustrating energy levels of the organic light-emitting device according to an exemplary embodiment.

First Embodiment—Descriptions of FIG. 4A

In the First Embodiment, the heterocyclic compound may be a fluorescence emitter. According to the First Embodiment, the emission layer may further include a host (hereinafter, referred to as 'Host A', and Host A may not be identical to the heterocyclic compound). Host A may be understood by referring to the description of the host material provided herein, but embodiments are not limited thereto. Host A may be a fluorescent host.

General energy transfer of the First Embodiment may be explained according to FIG. 2A.

Singlet excitons may be produced from Host A in the emission layer, and singlet excitons produced from Host A may be transferred to a fluorescence emitter through Förster energy transfer (FRET).

A ratio of singlet excitons produced from Host A may be 25%, and thus, 75% of triplet excitons produced from Host A may be fused to one another to be converted into singlet excitons. Thus, the efficiency of the organic light-emitting device may be further improved. That is, the efficiency of an organic light-emitting device may be further improved by using a triplet-triplet fusion mechanism.

According to the First Embodiment, a ratio of emission components emitted from the heterocyclic compound to the total emission components emitted from the emission layer may be about 80% or greater, for example, about 90% or greater. In some embodiments, a ratio of emission components emitted from the heterocyclic compound may be about 95% or greater to the total emission components emitted from the emission layer.

The heterocyclic compound may emit fluorescence, and the host may not emit light.

In the First Embodiment, when the emission layer further includes Host A, in addition to the heterocyclic compound, a content of the heterocyclic compound may be about 50 parts by weight or less, e.g., about 30 parts by weight or less, based on 100 parts by weight of the emission layer, and a content of Host A in the emission layer may be about 50 parts by weight or greater, e.g., about 70 parts by weight or greater, based on 100 parts by weight of the emission layer, but embodiments are not limited thereto.

In the First Embodiment, when the emission layer further includes Host A, in addition to the heterocyclic compound, Host A and the heterocyclic compound may satisfy Condition A:

$$E(H_A)_{S1} > E_{S1} \qquad \text{Condition A}$$

wherein, in Condition A, $E(H_A)_{S1}$ indicates a lowest excited singlet energy level of Host A, and $E_{S1}$ indicates a lowest excited singlet energy level of the heterocyclic compound.

Here, $E(H_A)_{S1}$ and $E_{S1}$ may be evaluated by using Gaussian according to density functional theory (DFT) method (wherein structure optimization is performed at a degree of B3LYP, and 6-31 G(d,p)).

Figure 4B:
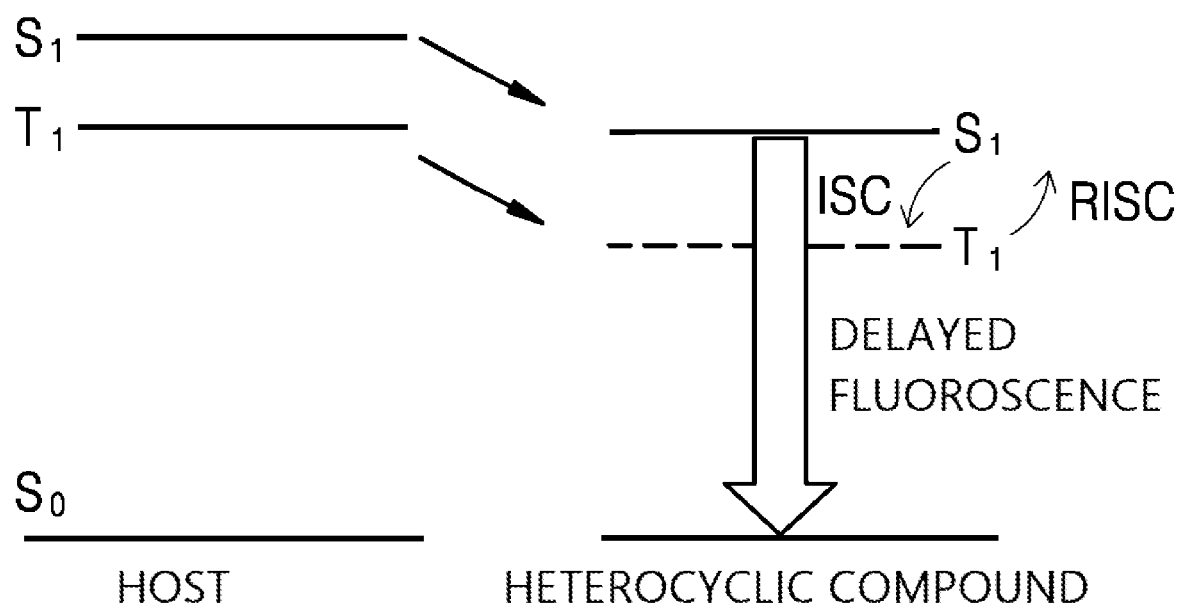

Second Embodiment—Descriptions of FIG. 4B

In the Second Embodiment, the heterocyclic compound may be a delayed fluorescence emitter. According to the Second Embodiment, the emission layer may further include a host (hereinafter, referred to as 'Host B', and Host B may not be identical to the heterocyclic compound). Host B may be understood by referring to the description of the host material provided herein, but embodiments are not limited thereto.

General energy transfer of the Second Embodiment may be explained according to FIG. 2B.

25% of singlet excitons produced from Host B in the emission layer may be transferred to a delayed fluorescence emitter through FRET. In addition, 75% of triplet excitons produced from Host B in the emission layer may be transferred to a delayed fluorescence emitter through Dexter energy transfer. Energy transferred to a triplet state of a delayed fluorescence emitter may undergo RISC to a singlet state. Accordingly, singlet excitons and triplet excitons produced from the emission layer may be transferred to the heterocyclic compound. Thus, the organic light-emitting device may have improved efficiency.

According to the Second Embodiment, a ratio of emission components emitted from the heterocyclic compound to the total emission components emitted from the emission layer may be about 80% or greater, for example, about 90% or greater. In some embodiments, a ratio of emission components emitted from the heterocyclic compound may be about 95% or greater to the total emission components emitted from the emission layer.

Here, the heterocyclic compound may emit fluorescence and/or delayed fluorescence, and the emission components of the heterocyclic compound may be a total of prompt emission components of the heterocyclic compound and delayed fluorescence components by RISC of the heterocyclic compound. In addition, Host B may not emit light.

In the Second Embodiment, when the emission layer further includes Host B, in addition to the heterocyclic compound, a content of the heterocyclic compound may be about 50 parts by weight or less, e.g., about 30 parts by weight or less, based on 100 parts by weight of the emission layer, and a content of Host B in the emission layer may be about 50 parts by weight or greater, e.g., about 70 parts by weight or greater, based on 100 parts by weight of the emission layer, but embodiments are not limited thereto.

In the Second Embodiment, when the emission layer further includes Host B, in addition to the heterocyclic compound, Host B and the heterocyclic compound may satisfy Condition B:

$$E(H_B)_{S1} > E_{S1} \qquad \text{Condition B}$$

wherein, in Condition B, $E(H_B)_{S1}$ indicates a lowest excited singlet energy level of Host B, and $E_{S1}$ indicates a lowest excited singlet energy level of the heterocyclic compound.

Here, $E(H_B)_{S1}$ and $E_{S1}$ may be evaluated by using Gaussian according to density functional theory (DFT) method (wherein structure optimization is performed at a degree of B3LYP, and 6-31 G(d,p)).

Third Embodiment and Fourth Embodiment

Figure 4C:
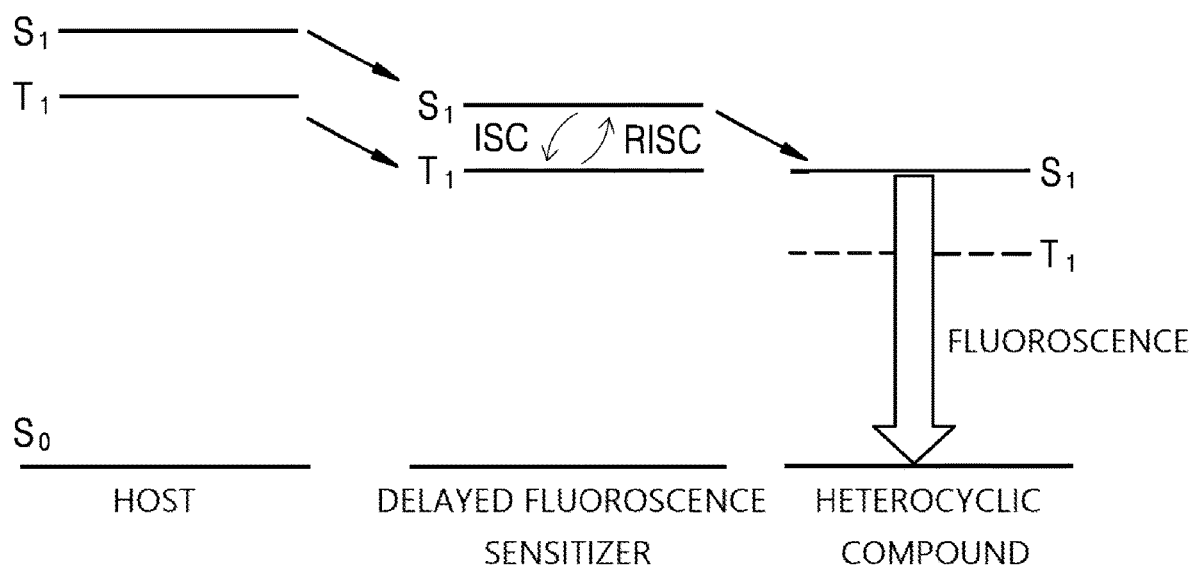

Third Embodiment—Descriptions of FIG. 4C

In the Third Embodiment, the heterocyclic compound may be used as a fluorescence emitter, and the emission layer may include a sensitizer, e.g., a delayed fluorescence sensitizer. In the Third Embodiment, the emission layer may further include a host (hereinafter, the host may be referred to as 'Host C', and Host C may not be identical to the heterocyclic compound and the sensitizer) and a sensitizer (hereinafter, the sensitizer may be referred to as 'Sensitizer A', and Sensitizer A may not be identical to Host C and the heterocyclic compound). Host C and Sensitizer A may respectively be understood by referring to the description of the host material and the sensitizer material provided herein, but embodiments are not limited thereto.

In the Third Embodiment, a ratio of emission components of the heterocyclic compound may be about 80% or greater, for example, about 90% or greater (or for example, about 95% or greater) to the total emission components emitted from the emission layer. For example, the heterocyclic compound may emit fluorescence. In addition, Host C and Sensitizer A may not each emit light.

General energy transfer of the Third Embodiment may be explained according to FIG. 2C.

Singlet and triplet excitons may be produced from Host C in the emission layer, and singlet and triplet excitons produced from Host C may be transferred to Sensitizer A and then to the heterocyclic compound through FRET. 25% of singlet excitons produced from Host C may be transferred to Sensitizer A through FRET, and energy of 75% of triplet excitons produced from Host C may be transferred to singlet and triplet states of Sensitizer A. Energy transferred to a triplet state of Sensitizer A may undergo RISC to a singlet state, and then, singlet energy of Sensitizer A may be transferred to the heterocyclic compound through FRET.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Third Embodiment, when the emission layer further includes Host C and Sensitizer A, in addition to the heterocyclic compound, Host C and Sensitizer A may satisfy Condition C-1 and/or C-2:

$$S_1(H_C) \geq S_1(S_A) \qquad \text{Condition C-1}$$

$$S_1(S_A) \geq S_1(HC) \qquad \text{Condition C-2}$$

wherein, in Conditions C-1 and C-2, $S_1(H_C)$ indicates a lowest excited singlet energy level of Host C, $S_1(S_A)$ indicates a lowest excited singlet energy level of Sensitizer A, and $S_1(HC)$ indicates a lowest excited singlet energy level of the heterocyclic compound.

$S_1(H_C)$, $S_1(S_A)$, and $S_1(HC)$ may be evaluated according to the DFT method, wherein structure optimization is performed at a degree of B3LYP, and 6-31G(d,p), for example, according to Gaussian according to DFT method.

When Host C, Sensitizer A, and the heterocyclic compound satisfy Condition C-1 and/or C-2, FRET from Sensitizer A to the heterocyclic compound may be facilitated, and accordingly, the organic light-emitting device may have improved luminescence efficiency.

Figure 4D:
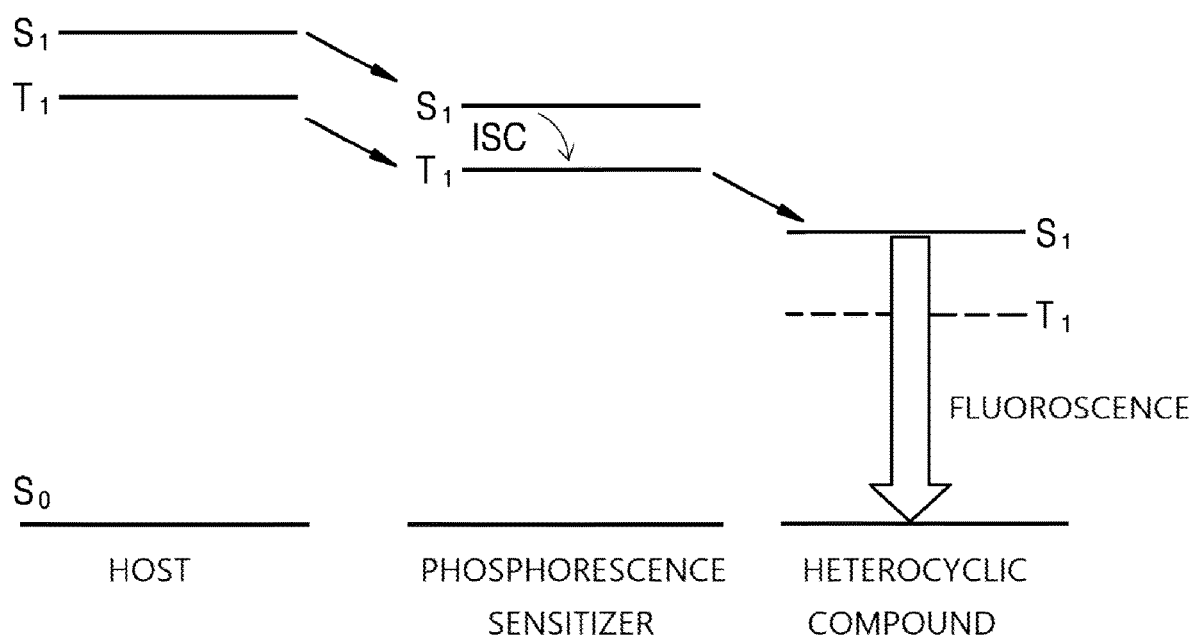
Figure 4E:
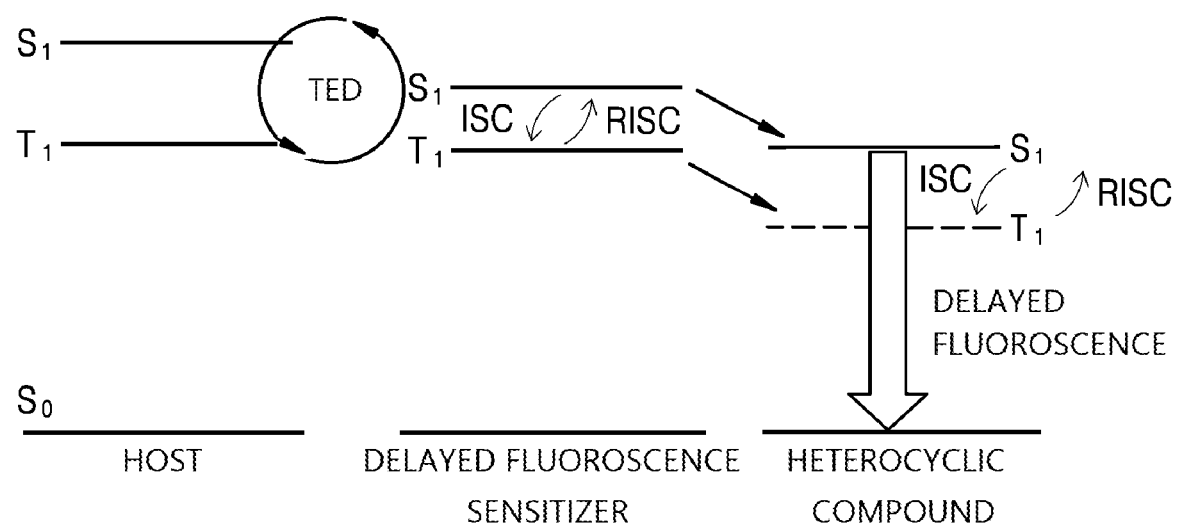

Fourth Embodiment—Descriptions of FIG. 4D

In the Fourth Embodiment, the heterocyclic compound may be used as a fluorescence emitter, and the emission layer may include a sensitizer, e.g., a phosphorescence sensitizer. In the Fourth Embodiment, the emission layer may further include a host (hereinafter, the host may be referred to as 'Host D', and Host D may not be identical to the heterocyclic compound and the sensitizer) and a sensitizer (hereinafter, the sensitizer may be referred to as 'Sensitizer B', and Sensitizer B may not be identical to Host D and the heterocyclic compound). Host D and Sensitizer B may respectively be understood by referring to the description of the host material and the sensitizer material provided herein, but embodiments are not limited thereto.

In the Fourth Embodiment, a ratio of emission components of the heterocyclic compound may be about 80% or greater, for example, about 90% or greater (or for example, about 95% or greater) to the total emission components emitted from the emission layer. For example, the heterocyclic compound may emit fluorescence. In addition, Host D and Sensitizer B may not each emit light.

General energy transfer of the Fourth Embodiment may be explained according to FIG. 2D.

75% of triplet excitons produced from Host D in the emission layer may be transferred to Sensitizer B through Dexter energy transfer, and energy of 25% of singlet excitons produced from Host D may be transferred to singlet and triplet states of Sensitizer B. Energy transferred to a singlet state of Sensitizer B may undergo ISC to a triplet state, and then, triplet energy of Sensitizer B may be transferred to the heterocyclic compound through FRET.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Third Embodiment, when the emission layer further includes Host D and Sensitizer B, in addition to the heterocyclic compound, Host D and Sensitizer B may satisfy Condition D-1 and/or D-2:

$$T_1(H_D) \geq T_1(S_B) \quad \text{Condition D-1}$$

$$T_1(SB) \geq S_1(H_C) \quad \text{Condition D-2}$$

wherein, in Conditions D-1 and D-2,
$T_1$(HD) indicates a lowest excited triplet energy level of Host D,
$T1(S_B)$ indicates a lowest excited triplet energy level of Sensitizer B, and
$S_1$(HC) indicates a lowest excited singlet energy level of the heterocyclic compound.

$T_1$(HD), $T_1$(SB), and $S_1$(HC) may be evaluated according to the DFT method, wherein structure optimization is performed at a degree of B3LYP, and 6-31G(d,p), for example, according to Gaussian according to DFT method.

When Host D, Sensitizer B, and the heterocyclic compound satisfy Condition D-1 and/or D-2, FRET from Sensitizer B to the heterocyclic compound may be facilitated, and accordingly, the organic light-emitting device may have improved luminescence efficiency.

In the Third Embodiment and the Fourth Embodiment, a content of the sensitizer in the emission layer may be in a range of about 5 percent by weight (wt %) to about 50 wt %, or for example, about 10 wt % to about 30 wt %. When the content is within this range, energy transfer in the emission layer may be effectively occurred. Thus, the organic light-emitting device may have high efficiency and long lifespan.

In the Third Embodiment and the Fourth Embodiment, a content of the heterocyclic compound in the emission layer may be in a range of about 0.01 wt % to about 15 wt %, or for example, about 0.05 wt % to about 3 wt %, but embodiments are not limited thereto.

In the Third Embodiment and the Fourth Embodiment, the sensitizer and the heterocyclic compound may further satisfy Condition 5:

$$0 \ \mu s < T_{decay}(HC) < 5 \ \mu s \quad \text{Condition 5}$$

wherein, in Condition 5,
$T_{decay}$(HC) indicates a decay time of the heterocyclic compound.

The decay time of the heterocyclic compound was measured from a time-resolved photoluminescence (TRPL) spectrum at room temperature of a film (hereinafter, referred to as "Film (HC)") having a thickness of 40 nm formed by vacuum-depositing the host and the heterocyclic compound included in the emission layer on a quartz substrate at a weight ratio of 90:10 at a vacuum pressure of $10^{-7}$ torr.

Fifth Embodiment—Descriptions of FIG. 5E

In the Fifth Embodiment, the heterocyclic compound may be used as a delayed fluorescence emitter, and the emission layer may include a sensitizer, e.g., a delayed fluorescence sensitizer. In the Fifth Embodiment, the emission layer may further include a host (hereinafter, the host may be referred to as 'Host E', and Host E may not be identical to the heterocyclic compound and the sensitizer) and a sensitizer (hereinafter, the sensitizer may be referred to as 'Sensitizer C', and Sensitizer C may not be identical to Host E and the heterocyclic compound). Host E and Sensitizer C may respectively be understood by referring to the description of the host material and the sensitizer material provided herein, but embodiments are not limited thereto.

In the Fifth Embodiment, a ratio of emission components of the heterocyclic compound may be about 80% or greater, for example, 90% or greater (or for example, 95% or greater) to the total emission components emitted from the emission layer. In some embodiments, the heterocyclic compound may emit fluorescence and/or delayed fluorescence. In addition, Host E and Sensitizer C may not each emit light.

Here, the heterocyclic compound may emit fluorescence and/or delayed fluorescence, and the emission components of the heterocyclic compound may be a total of prompt emission components of the heterocyclic compound and delayed fluorescence components by RISC of the heterocyclic compound.

General energy transfer of the Fifth Embodiment may be explained according to FIG. 2E.

25% of singlet excitons produced from Host E in the emission layer may be transferred to a singlet state of Sensitizer C through FRET, and energy of 75% of triplet excitons produced from Host E may be transferred to a triplet state of Sensitizer C, and then singlet energy of Sensitizer C may be transferred to the heterocyclic compound through FRET. Subsequently, the triplet energy of Sensitizer C may be transferred to the heterocyclic compound through Dexter energy transfer. Energy transferred to a triplet state of Sensitizer C may undergo RISC to a singlet state. Further, in a case of Sensitizer C, energy of triplet excitons produced from Sensitizer C may undergo reverse transfer to Host E and then to the heterocyclic compound, thus emitting by reverse intersystem transfer.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Fifth Embodiment, when the emission layer further includes Host E and Sensitizer C, in addition to the heterocyclic compound, Host E and Sensitizer C may satisfy Condition E-1, E-2, and/or E-3:

$$S_1(H_E) \geq S_1(S_C) \quad \text{Condition E-1}$$

$$S_1(S_C) \geq S_1(HC) \quad \text{Condition E-2}$$

$$T_1(S_C) \geq T_1(HC) \quad \text{Condition E-3}$$

wherein, in Conditions E-1, E-2, and E-3, $S_1(H_E)$ indicates a lowest excited singlet energy level of Host E, $S_1(S_C)$ indicates a lowest excited singlet energy level of Sensitizer C, $S_1(HC)$ indicates a lowest excited singlet energy level of the heterocyclic compound, $T_1(S_C)$ indicates a lowest excited triplet energy level of Sensitizer C, and $T_1(HC)$ indicates a lowest excited triplet energy level of the heterocyclic compound.

$S_1(H_E)$, $S_1(SC)$, $S_1(HC)$, $T_1(S_C)$, and $T_1(HC)$ may be evaluated according to the DFT method, wherein structure optimization is performed at a degree of B3LYP, and 6-31 G(d,p), for example, according to Gaussian according to DFT method.

When Host E, Sensitizer C, and the heterocyclic compound satisfy Condition E-1, E-2, and/or E-3, Dexter transfer FRET from Sensitizer C to the heterocyclic compound may be facilitated, and accordingly, the organic light-emitting device may have improved luminescence efficiency.

In the Fifth Embodiment, a content of Sensitizer C in the emission layer may be in a range of about 5 wt % to about 50 wt %, or for example, about 10 wt % to about 30 wt %. When the content is within this range, energy transfer in the emission layer may be effectively occurred. Thus, the organic light-emitting device may have high efficiency and long lifespan.

In the Fifth Embodiment, a content of the heterocyclic compound in the emission layer may be in a range of about 0.01 wt % to about 15 wt %, or for example, about 0.05 wt % to about 3 wt %, but embodiments are not limited thereto.

Hereinafter, each region and each layer other than the emission layer 4 will be described in detail.

Substrate 1

The organic light-emitting device 10 may include the substrate 1. The substrate 1 may be any suitable substrate generally used in organic light-emitting devices. For example, the substrate 1 may be a glass substrate, a silicon substrate, or a transparent plastic substrate having excellent mechanical strength, thermal stability, transparency, surface smoothness, ease of handling, and water repellency, but embodiments are not limited thereto.

First Electrode 2

The first electrode 2 may be formed on the substrate 1. The first electrode 2 may be an anode and be formed of a material with a relatively high work function selected from a metal, an alloy, a conductive compound, and a combination thereof, for facilitating hole injection. The first electrode 2 may be a pixel electrode. The first electrode 2 may be a reflective electrode, a semi-transmissive electrode, or a transmissive electrode. The materials for forming the first electrode 2 are not particularly limited and may be, for example, indium tin oxide (ITO), indium zinc oxide (IZO), tin oxide (SnO$_2$), zinc oxide (ZnO), indium tin zinc oxide (ITZO), or the like, having excellent transparency and conductivity, when the first electrode 2 is a transparent electrode. When the first electrode 2 is a semi-transmissive or reflective electrode, Ag, Mg, Cu, Al, Pt, Pd, Au, Ni, Nd, Ir, Cr, Li, Ca, In, LiF/Ca, LiF/, Mo, Ti, or a mixture thereof (e.g., a mixture of Ag and Mg or a mixture of Mg and In) may be included.

The first electrode 2 may be a single layer including a single material or a single layer including a plurality of different materials. In some embodiments, the first electrode 2 may have a multi-layer structure including a plurality of layers including various different materials.

The thickness of the first electrode 2 is not particularly limited and may be about 10 nm or greater and about 1,000 nm or lower, or about 100 nm or greater and about 300 nm or lower.

Hole Transport Region 3

The hole transport region 3 may be disposed on the first electrode 2.

The hole transport region 3 may include at least one of a hole injection layer 31, a hole transport layer 32, an electron blocking layer (33), a hole buffer layer (not shown), or any combination thereof.

The hole transport region 3 may be a single layer including a single material or a single layer including a plurality of different materials. In some embodiments, the hole transport region 3 may have a multi-layer structure including a plurality of layers including various different materials.

The hole transport region 3 may include the hole injection layer 31 only or the hole transport layer 32 only. In some embodiments, the hole transport region 3 may be a single layer including a hole injection material and a hole transporting material. The hole transport region 3 may have a hole injection layer/hole transport layer structure, a hole injection layer/hole buffer layer structure, a hole injection layer/hole transport layer/hole buffer layer structure, or a hole injection layer/hole transport layer/electron blocking layer structure, wherein layers of each structure are sequentially stacked on the first electrode 2 in each stated order.

Layers forming the hole injection layer 31 and other layers included in the hole transport region 3 are not particularly limited, and a known hole injection material and/or a hole transporting material may be included. The hole injection material and/or the hole transporting material may include at least one of, for example, poly(ether ketone)-containing triphenylamine (TPAPEK), 4-isopropyl-4'-methyldiphenyliodonium tetrakis(pentafluorophenyl) borate (PPBI), dipyrazino[2,3-f:2',3'-h]quinoxaline-2,3,6,7,10,11-hexacarbonitrile (HAT-CN), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino) triphenylamine (m-MTDATA), N,N'-di(1-naphthyl)-N,N'-diphenylbenzidine (NPB), 4,4',4"-tris(diphenylamino) triphenylamine (TDATA), 4,4',4"-tris(N,N-2-naphthylphenylamino) triphenylamine (2-TNATA), polyaniline/dodecylbenzenesulphonic acid (PANI/DBSA), poly(3,4-ethylenedioxythiophene)/poly(4-styrenesulfonate) (PEDOT/PSS), polyaniline/10-camphorsulfonic acid (PANI/CSA), polyaniline/poly(4-styrenesulfonate) (PANI/PSS), 1,1-bis[(di-4-tolylamino)phenyl] cyclohexane (TAPC), a carbazole derivative such as N-phenylcarbazole or polyvinylcarbazole, a fluorene-based derivative, N,N'-bis (3-methylphenyl)-N,N'-diphenyl-[1,1-biphenyl]-4,4'-diamine (TPD), 4,4',4"-tris(N-carbazolyl) triphenylamine (TCTA), N,N'-di(1-naphthyl)-N,N'-diphenylbenzidine (NPB), 4,4'-bis[N,N'-(3-tril)amino]-3,3'-dimethyl phenyl (HMTPD), 1,3-bis(carbazol-9-yl)benzene (mCP), poly(9,9-dioctyl-fluorene-co-N-(4-butylphenyl)-diphenylamine (TFB), Compound HTP1, Compound AD1, Compound P-1, Compound FA-14, or any combination thereof:

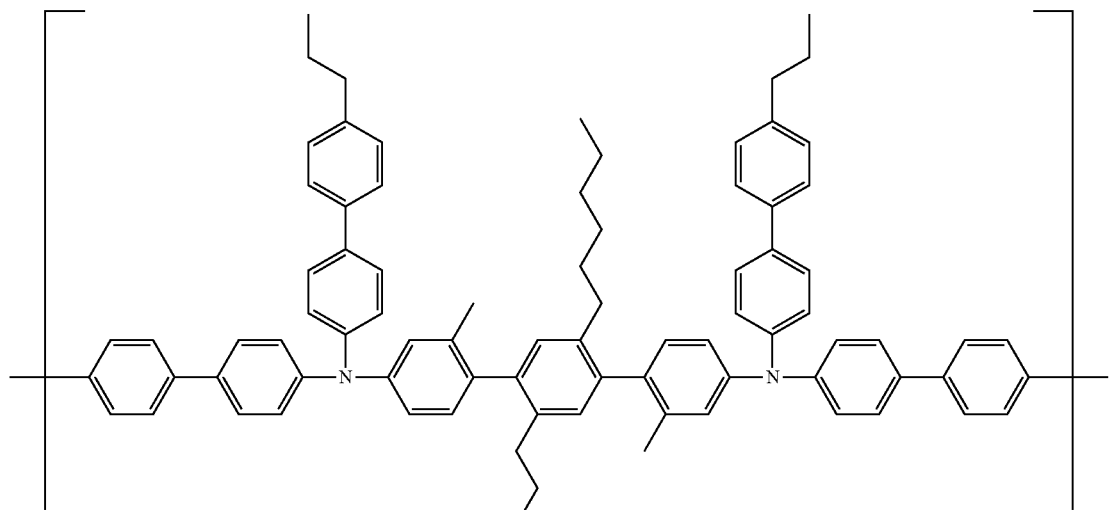
HTP1
(n is a integer of 1 or more)
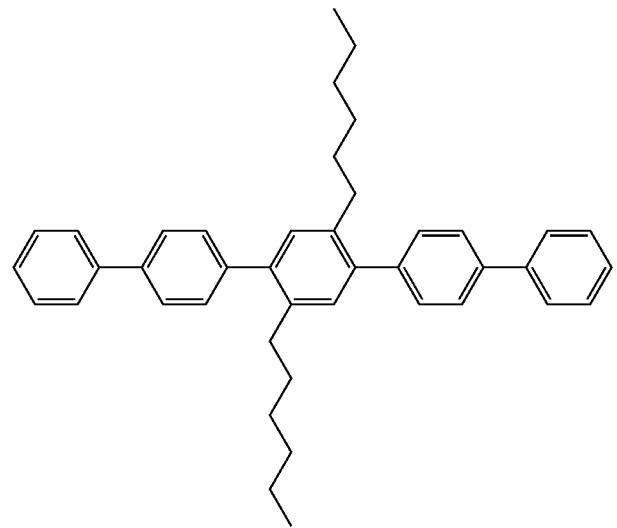
AD1

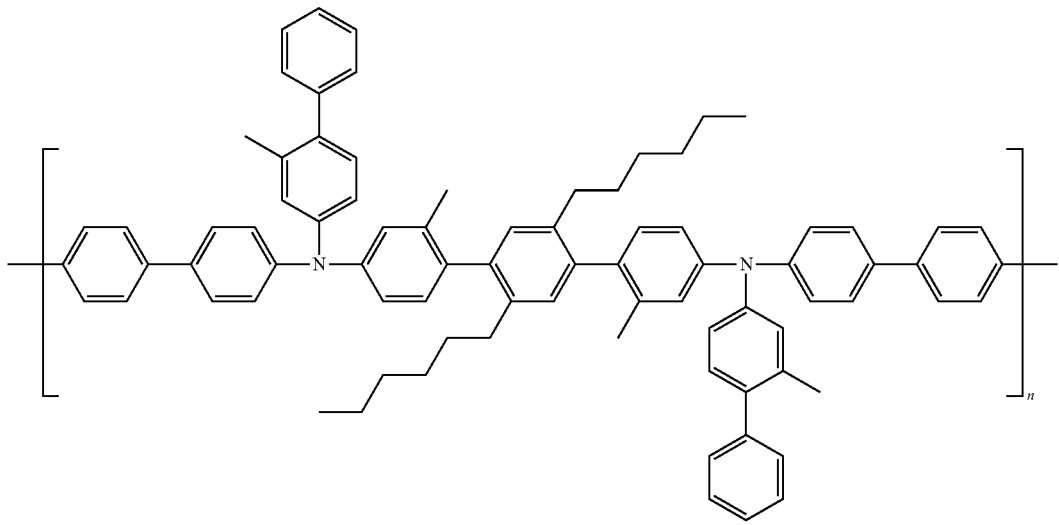

P-1 n is a integer of 1 or more)

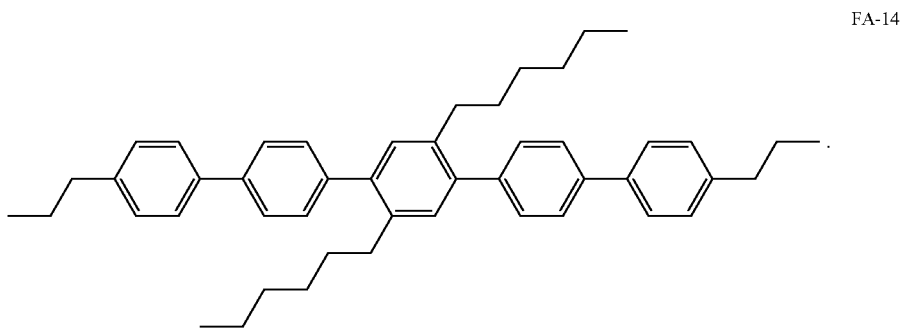 [SMILES: CCCCCCc1cc(-c2ccc(-c3ccc(CCC)cc3)cc2)c(CCCCCC)cc1-c1ccc(-c2ccc(CCC)cc2)cc1]

FA-14

The hole transport region 3 may include a charge generating material as well as the aforementioned materials, to improve conductive properties of the hole transport region. The charge generating material may be substantially homogeneously or non-homogeneously dispersed in the hole transport region 3.

The charge generating material is not particularly limited and may be, for example, a p-dopant. Examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, but embodiments are not limited thereto:

The hole buffer layer (not shown) may increase luminescence efficiency by compensating for an optical resonance distance according to the wavelength of light emitted by the emission layer 4. Materials for forming the hole buffer layer (not shown) are not particularly limited, and a known hole buffer layer material may be used, e.g., the compounds that may be included in the hole transport region 3.

The electron blocking layer 33 may prevent electron injection from the electron transport region 5 to the hole transport region 3. Materials for forming the electron blocking layer 33 are not particularly limited, and a known electron blocking layer material may be used, e.g., the compounds that may be included in the hole transport region 3.

The thickness of the hole transport region 3 is not particularly limited and may be about 1 nm or greater and about 1,000 nm or lower, or for example, about 10 nm or greater and about 500 nm or lower. In addition, the thickness of the hole injection layer 31 is not particularly limited and may be about 3 nm or greater and about 100 nm or lower. In addition, the thickness of the hole transport layer 32 is not particularly limited and may be about 3 nm or greater and about 100 nm or lower. In addition, the thickness of the electron blocking layer 33 is not particularly limited and may be about 1 nm or greater and about 100 nm or lower. In addition, the thickness of the hole buffer layer (not shown) is not particularly limited, as long as the hole buffer layer may not adversely effect on functions of an organic light-emitting device. When the thicknesses of the hole transport region 3, the hole injection layer 31, the hole transport layer 32, or the electron blocking layer 33 are within these ranges, excellent hole transport characteristics may be obtained without a substantial increase in driving voltage.

Emission Layer 4

The hole transport region 3 may be disposed on the mission layer 4. The emission layer 4 may be understood by referring to the description of the emission layer 4 described above.

Electron Transport Region 5

The electron transport region 5 may be disposed on the emission layer 4. The electron transport region 5 may include at least one of a hole blocking layer 53, the electron transport layer 52, the electron injection layer 51, or any combination thereof.

The electron transport region 5 may be a single layer including a single material or a single layer including a plurality of different materials. In some embodiments, the electron transport region 5 may have a multi-layer structure including a plurality of layers including various different materials.

The electron transport region 5 may include the electron transport layer 52 only or the electron injection layer 51 only. In some embodiments, the electron transport region 5 may be a single layer including an electron injection material and an electron transporting material. In some embodiments, the electron transport region 5 may include an electron transport layer/electron injection layer structure or a hole blocking layer/electron transport layer/electron injection layer structure, which are sequentially stacked on the emission layer 4.

The electron injection layer 51 is not particularly limited and may include, for example, a known electron injection material. For example, the electron injection layer material may include Yb, a lithium compound, e.g., (8-hydroxyquinolinato)lithium (Liq) and lithium fluoride (LiF), sodium chloride (NaCl), cesium fluoride (CsF), rubidium fluoride (RbCl), lithium oxide ($Li_2O$), or barium oxide (BaO).

In some embodiments, the electron injection layer 51 may include the electron transport material and an insulating organic metal salt. The metal salt is not particularly limited and may be, for example, a material having an energy band gap of about 4 eV or higher. The organic metal salt may include, for example, an acetate metal salt, a benzoate metal salt, an acetate metal salt, an acetyl acetonate metal salt, or a stearate metal salt.

The electron transport layer 52 is not particularly limited and may include, for example, a known electron transport material. The electron transport material may be, for example, tris(8-quinolinato) aluminium ($Alq_3$), Balq, 1,3,5-tri[(3-pyridyl)-phen-3-yl]benzene, beryllium bis(benzoquinoline-10-olate (Bebq2), 9,10-di(naphthalene-2-yl)anthracene (ADN), 1,3,5-tri [(3-pyridyl)-pen-3-yl]benzene, 2,4,6-tris(3'-(pyridin-3-yl)biphenyl-3-yl)-1,3,5-triazine, 2-(4-(N-phenylbenzimidazolyl-1-yl-phenyl)-9,10-dinaphthylanthracene, 3-(4-phenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tris(N-phenyl-benzimidazol-2-yl)benzene (TPBi), 2,9-dimethyl-4,7-diphenyl-1,10-phenanthroline (BCP), 4,7-diphenyl-1,10-phenanthroline (Bphen), 2-(4-biphenyl)-5-(4-tert-butylphenyl)-1,3,4-oxadiazole (tBu-PBD), KLET-01, KLET-02, KLET-03, KLET-10, or KLET-M1 (available from Chemipro Kasei).

The hole blocking layer 53 may prevent hole injection from the hole transport region 3 to the electron transport region 5. Materials included in the hole blocking layer 53 are not particularly limited, and a known hole blocking material may be used. The hole blocking layer 53 may be, for example, 2,9-dimethyl-4,7-diphenyl-1,10-phenanthroline (BCP), 4,7-diphenyl-1,10-phenanthroline (Bphen), or the like.

The thickness of the electron transport region 5 is not particularly limited and may be about 0.1 nm or greater and about 210 nm or lower, or for example, about 100 nm or greater and about 150 nm or lower. The thickness of the electron transport layer 52 is not particularly limited and may be about 10 nm or greater and about 100 nm or lower, or for example, about 15 nm or greater and about 50 nm or lower. The thickness of the hole blocking layer 53 is not particularly limited and may be about 10 nm or greater and about 100 nm or lower, or for example, about 15 nm or greater and about 50 nm or lower. The thickness of the electron injection layer 51 is not particularly limited and may be about 0.1 nm or greater and about 10 nm or lower, or for example, about 0.3 nm or greater and about 9 nm or lower. When the thickness of the electron injection layer 51 is within any of these ranges, excellent electron injection characteristics may be obtained without a substantial increase in driving voltage. When the thicknesses of the electron transport region 5, the electron injection layer 51, the electron transport layer 52, or the hole blocking layer 53 are within these ranges, excellent hole transport characteristics may be obtained without a substantial increase in driving voltage.

Second Electrode 6

The second electrode 6 may be formed on the electron injection layer 51. The second electrode 6 may be a cathode and be formed of a material with a relatively low work function selected from a metal, an alloy, or a conductive compound, for facilitating electron injection. The second electrode 6 may be a common electrode. The second electrode 6 may be a reflective electrode, a semi-transmissive electrode, or a transmissive electrode. The second electrode 6 may have a single-layered structure or a multi-layered structure including a plurality of layers. Materials for forming the second electrode 6 are not particularly limited, and for example, the second electrode 6 may include a transparent metal oxide, e.g., ITO, IZO, ZnO, or ITZO, when the second electrode 6 is a transparent electrode. When the second electrode 6 is a semi-transmissive or reflective electrode, Ag, Mg, Cu, Al, Pt, Pd, Au, Ni, Nd, Ir, Cr, Li, Ca, In, LiF/Ca, LiF/, Mo, Ti, or a mixture thereof (e.g., a mixture of Ag and Mg or a mixture of Mg and In) may be included.

The second electrode 6 may be a single layer including a single material or a single layer including a plurality of different materials. In some embodiments, the second electrode 6 may have a multi-layer structure including a plurality of layers including various different materials.

In addition, the thickness of the second electrode 6 is not particularly limited and may be about 10 nm or greater and about 1,000 nm or lower.

The second electrode 6 may be further connected to an ancillary electrode (not shown). When the second electrode 6 is connected to an ancillary electrode, a resistance of the second electrode 6 may be further reduced.

An encapsulation layer (not shown) may be further on the second electrode 6.

The encapsulation layer (not shown) may be, for example, α-NPD, NPB, TPD, m-MTDATA, Alq3, CuPc, N4,N4,N4', N4'-tetra(phenyl-4-yl)biphenyl-4,4'-diamine (TPD15), TCTA, or N,N'-bis(naphthalene-1-yl).

Furthermore, a stacking structure of the organic light-emitting device 10 according to an embodiment is not limited to the foregoing description. The organic light-emitting device 10 according to an embodiment may have a different stacking structure known in the art. For example, the organic light-emitting device 10 may not include at least one selected from the hole injection layer 31, the hole transport layer 32, the electron transport layer 52, and the electron injection layer 51 or may further include another layer. In some embodiments, each layer of the organic light-emitting device 10 may be formed as a single layer or as multiple layers.

Methods of forming each layer of the organic light-emitting device 10 according to one or more embodiments are not particularly limited. For example, vacuum-deposition, solution coating, a laser printing method, Langmuir-Blodgett (LB) method, or laser induced thermal imaging (LITI), may be used in forming each layer thereof.

The solution coating may include spin coating, casting, micro-gravure coating, gravure coating, bar coating, roll coating, wire bar coating, dip coating, spray coating, screen printing, flexographic printing, offset printing, or ink-jet printing.

The solvent used in the solution coating may include toluene, xylene, diethyl ether, chloroform, ethyl acetate, dichloromethane, tetrahydrofuran, acetone, acetonitrile, N,N-dimethyl form amide, dimethyl sulfoxide, anisole, hexamethylphosphoric acid triamide, 1,2-dichloroethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol monobutyl ether, ethylene glycol monoethyl ether, ethylene glycol monomethyl ether, dimethoxy ethane, propylene glycol, diethoxy methane, triethylene glycol monoethyl ether, glycerine, 1,2-hexanediol, methanol, ethanol, propanol, isopropanol, cyclohexanol, N-methyl-2-pyrrolidone, or any combination thereof. However, the solvent is not particularly limited. Any suitable solvent that may dissolve materials for forming each layer may be used.

In consideration of coatability or the like, a concentration of the composition may be about 0.1 percent by weight (wt %) or greater and 10 wt % or less, and more particularly, about 0.5 wt % or greater and 5 wt % or less, but embodiments are not limited thereto.

The vacuum deposition may be performed at a deposition temperature in a range of about 100° C. to about 500° C., at a vacuum pressure in a range of about $10^{-8}$ torr to about $10^{-3}$ torr, and at a deposition rate in a range of about 0.01 nm per second (nm/sec) to about 10 nm/sec, though the conditions may vary depending on a compound that is used and a structure and thermal properties of a desired layer.

In some embodiments, the first electrode 2 may be an anode, and the second electrode 6 may be a cathode.

For example, the first electrode 2 may be an anode, the second electrode 6 may be a cathode, and an organic layer may include the emission layer 4 between the first electrode 2 and the second electrode 6 and may further include a hole transport region between the first electrode 2 and the emission layer 4 and an electron transport region between the emission layer 4 and the second electrode 6, wherein the hole transport region 3 may include at least one of a hole injection layer 31, a hole transport layer 32, a hole buffer layer, an electron blocking layer, or any combination thereof, and the electron transport region 5 may include at least one of a hole blocking layer, the electron transport layer 52, the electron injection layer 51, or any combination thereof.

In some embodiments, the first electrode 2 may be a cathode, and the second electrode 6 may be an anode.

Hereinbefore, the organic light-emitting device 10 has been described with reference to FIGS. 1 to 3, but embodiments are not limited thereto.

Hereinafter, the Examples in which the heterocyclic compound is included in the emission layer 4 will be described in detail.

Electronic Apparatus

The organic light-emitting device may be included in various electronic apparatuses.

The electronic apparatus may further include a thin-film transistor, in addition to the organic light-emitting device. The thin-film transistor may include a source electrode, a drain electrode, and an activation layer, wherein one of the source electrode and the drain electrode may be electrically connected to one of the first electrode and the second electrode of the organic light-emitting device.

Hereinafter, an organic light-emitting device, according to an embodiment, will be described in more detail with reference to Synthesis Examples and Examples; however, the present disclosure is not limited thereto. The wording "B was used instead of A" used in describing Synthesis Examples means that an identical molar equivalent of B was used in place of A.

EXAMPLES

Mass Analysis

A compound was dissolved in tetrahydrofuran (THF) at a concentration of 0.1 wt % and mass-analysis was performed by using LC-MS measurement apparatus 1260 Infinity-4 Quadrupole 6100MS (available from Agilent technologies).

Measurement of NMR Spectrum

THF substituted deuterium (THF-d8) was used to dissolve the compound, and $^1$H-NMR spectrum of the compound was measured at room temperature by using Avance III (300 MHz at Bruker).

Example 1

Synthesis Example 1: Synthesis of Intermediate (11)

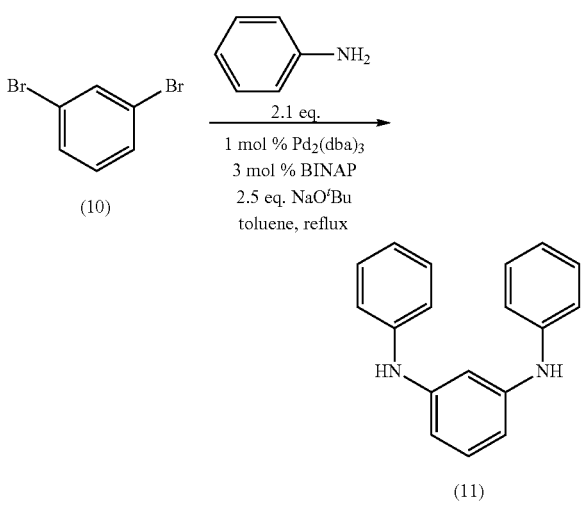

21 grams (g) (89 millimoles (mmol)) of m-dibromobenzene (10), 17.4 g (187 mmol) of aniline, 21.4 g (223 mmol) of sodium tert-butoxide, 815 mg (0.89 mmol) of tris(dibenzylideneacetone)palladium(0), and 1.66 g (2.67 mmol) of (±)2,2'-bis(diphenylphosphino)-1,1'-binaphthyl (BINAP) were added to a 1 L 3-neck flask, followed by addition of 300 mL of toluene and heating under reflux for 3 hours in a nitrogen atmosphere. After cooling to room temperature, the reaction solution was passed through Florisil and a silica gel pad, and the solvent was distilled off. The obtained residue was purified by column chromatography (eluent: hexane-ethyl acetate) to obtain Intermediate (11) (yield: 7.5 g, 32%).

Synthesis Example 2: Synthesis of Intermediate (13)

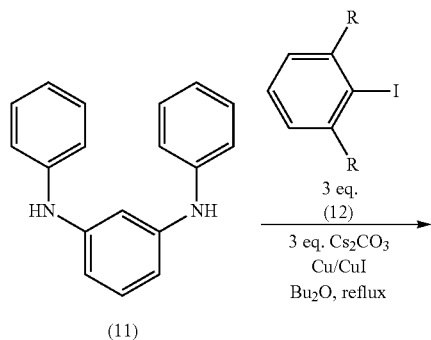

1.56 g (6.0 mmol) of Intermediate (11), 5.8 g (18 mmol) of dimethyl 2-iodo-1,3-benzene dicarboxylate (Compound (12)), 5.5 g (18 mmol) of cesium carbonate, 114 mg (1.8 mmol) of copper powder, 228 mg (1.2 mmol) of copper iodide, and 24 mL of dibutyl ether were added to a 100 mL of Schlenk tube, followed by heating under reflux for 5 days in a nitrogen atmosphere. After cooling to room temperature, water was added to the reaction solution. After separating the organic layer, the water layer was extracted by using ethyl acetate. The organic layer was washed with saturated brine and dried using anhydrous sodium sulfate. After removing the desiccant, the organic solvent was distilled off. The obtained residue was purified by silica gel column chromatography (eluent: dichloromethane-ethyl acetate) to obtain Intermediate (13) (yield: 1.65 g, 43%).

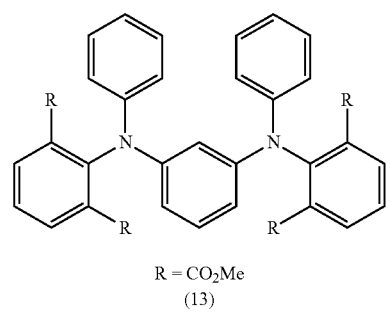

Synthesis Example 3: Synthesis of Intermediate (14)

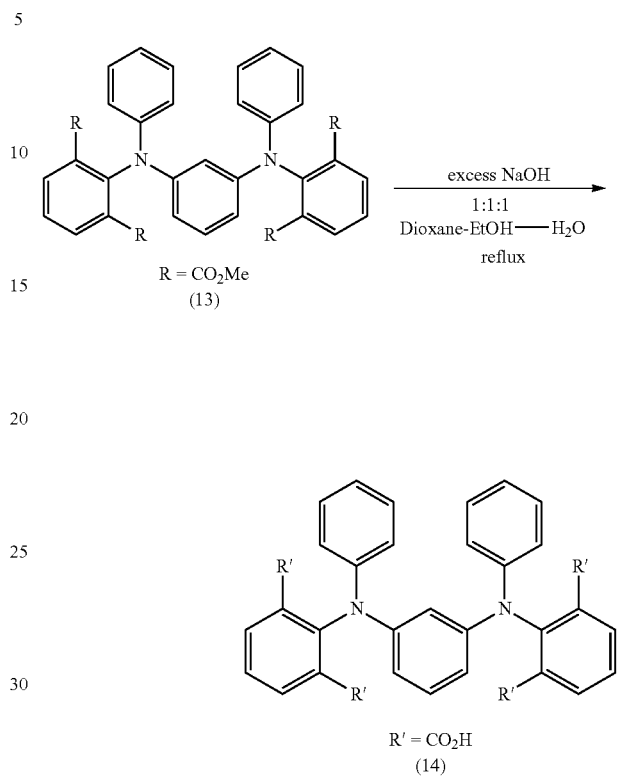

1.62 g (2.5 mmol) of Intermediate (13) was added to a 100 mL-flask, followed by adding 20 mL of dioxane, 20 mL of ethanol, and 10 mL of water. After adding 10 g (100 mmol) of 10 molar (M) aqueous sodium hydroxide solution, the mixture was heated and refluxed under nitrogen atmosphere for 2 hours. After cooling to room temperature, the organic solvent was distilled off. After the residue was cooled to a temperature of 0° C., the solution was acidified by adding hydrochloric acid until the pH reached 2 to 3. The precipitated solid was filtered off, washed repeatedly with water, and vacuum-dried to obtain Intermediate (14) (yield 1.48 g, 100%).

Synthesis Example 4: Synthesis of Compound 15 and Compound 16

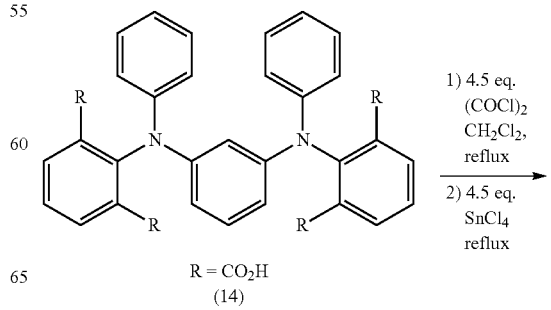

-continued

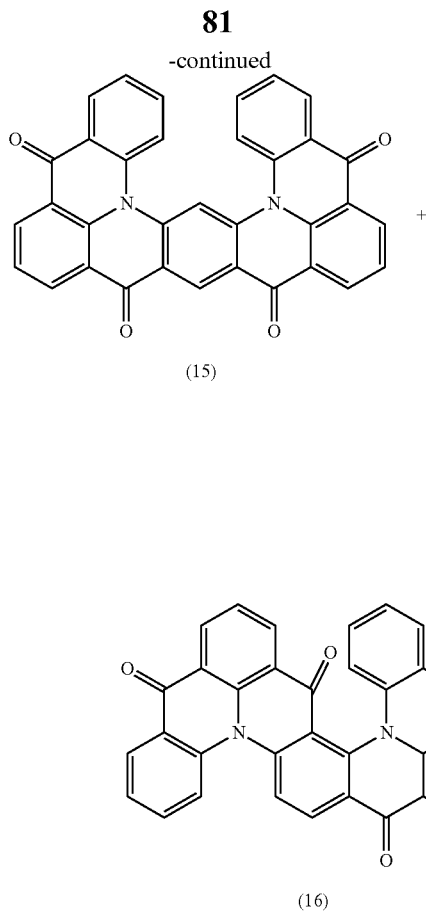

(15)

(16)

1.38 g (2.34 mmol) of Intermediate (14) was added to a 300 mL 3-neck flask, followed by adding 120 mL of dichloromethane. Subsequently, N,N'-dimethyl formamide (3 droplets) and 0.90 mL (10.5 mmol) of oxalyl chloride were added thereto, followed by heating under reflux. After 2 hours, tin (IV) tetrachloride (10.5 mL of 1 M dichloromethane solution, 10.5 mmol) was added thereto, and then the mixture was heated under reflux for additional 5 hours. After cooling to 0° C., 100 mL of 1 M aqueous hydrochloric acid solution was added. After separating the organic layer, the water layer was extracted by using dichloromethane. The organic layer was washed with a saturated aqueous ammonium chloride solution and dried over anhydrous sodium sulfate. After passing the resulting mixture through a silica gel pad to remove the desiccant, the organic solvent was distilled off. The obtained residue was suspended in dichloromethane, and the solid was isolated by filtration to obtain Compound 15. In addition, the obtained residue was purified using silica gel column chromatography (eluent: dichloromethane-ethyl acetate) to obtain Compound 16.

Figure 5:
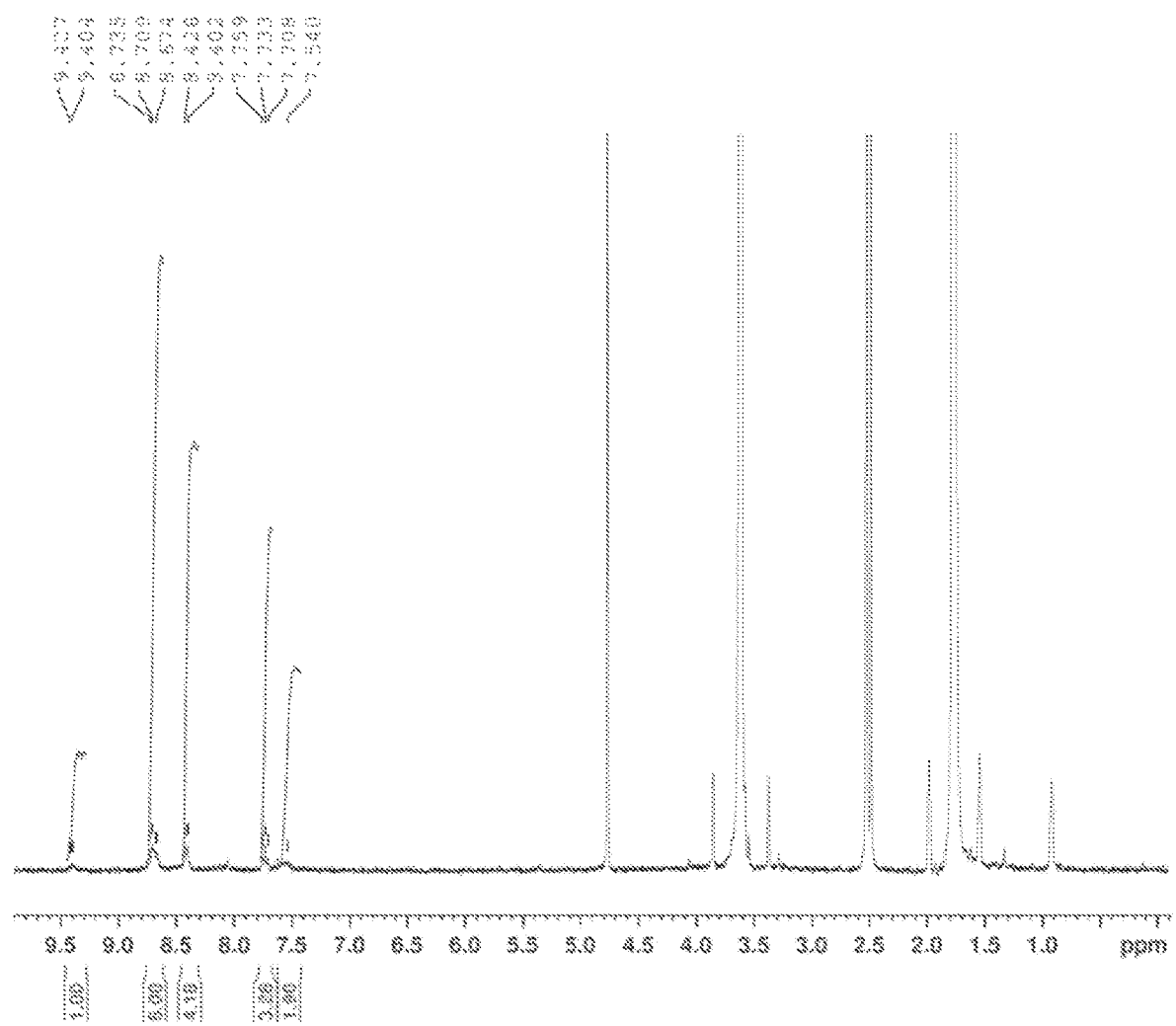
FIG. 5 is a view showing a 1H-NMR spectrum of Compound 15.

Compound 15: yield: 0.35 g, 30%; 1H-NMR: δ 7.54 (brs, 2H), 7.70-7.56 (m, 3H), 8.40-8.43 (m, 4H), 8.65-8.74 (m, 6H), 9.40-9.43 (brs, 1H) (see FIG. 5); LC-MS: 517 (M+H+)

Figure 6:
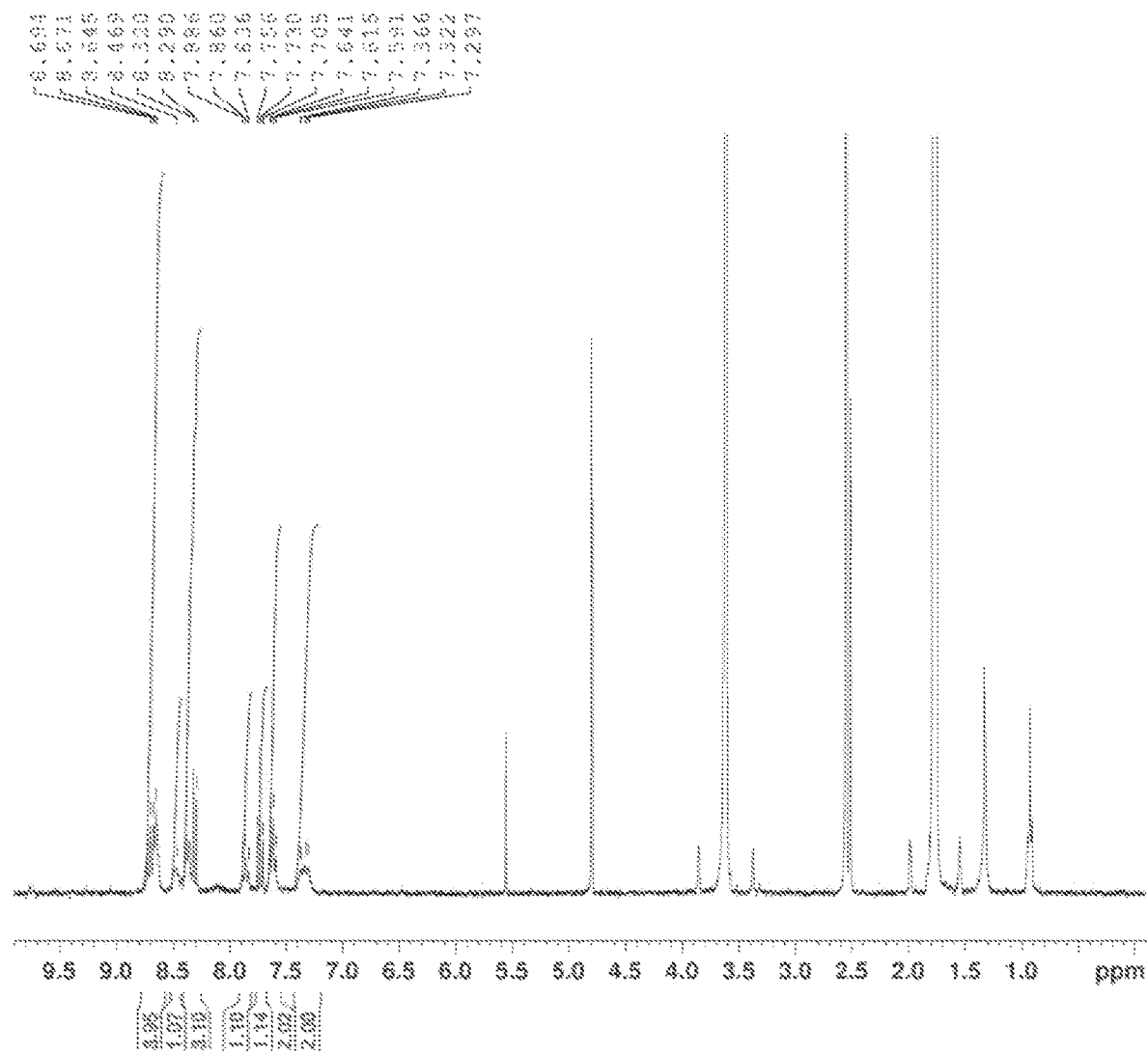
FIG. 6 is a view showing a 1H-NMR spectrum of Compound 16.

Compound 16: yield 0.33 g, 26%; 1H-NMR: δ 7.25-7.40 (m, 2H), 7.58-7.68 (m, 2H), 7.73 (t, 1H, J=7.8 Hz) 7.82-7.89 (m, 1H), 8.30 (d, 1H, J=9 Hz), 8.34-8.40 (m, 2H), 8.45-9.50 (m, 1H), 8.62-8.75 (m, 4H) (see FIG. 6); LC-MS: 517 (M+H+).

Example 2

Synthesis Example 5: Synthesis of Intermediate (17)

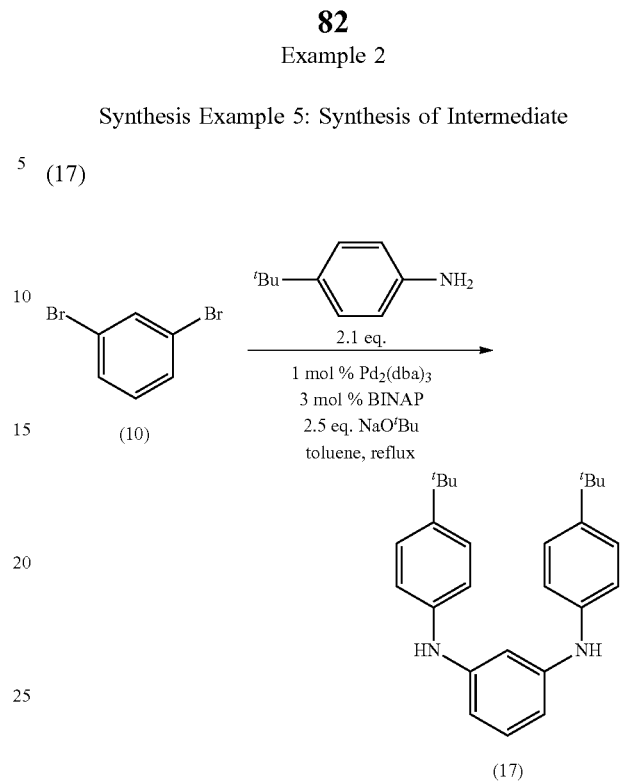

(17)

Intermediate (17) was obtained in the same manner as in Synthesis Example 1, except that 4-tert-butyl amine was used instead of aniline (yield 86%).

Synthesis Example 6: Synthesis of Intermediate (19)

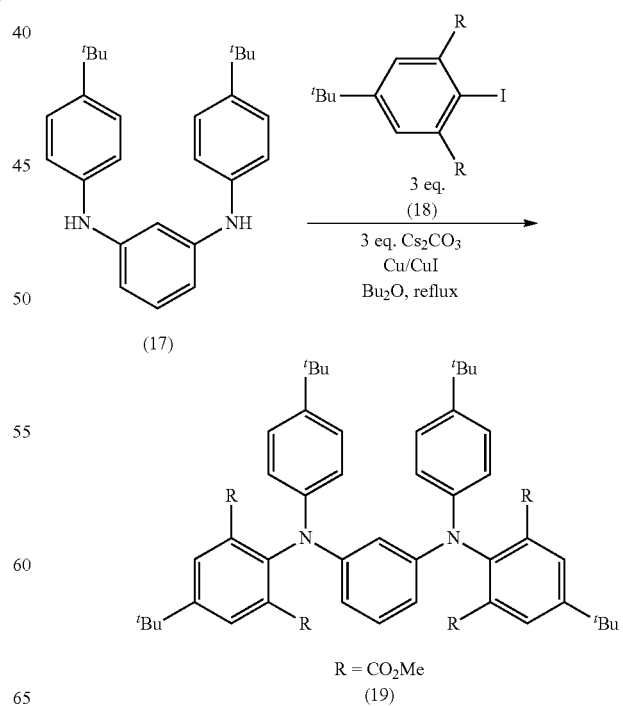

R = CO$_2$Me
(19)

Intermediate (19) was obtained in the same manner as in Synthesis Example 2, except that Intermediate (17) was used instead of Intermediate (11), and Compound (18) was used instead of Compound (12) (yield 73%).

Synthesis Example 7: Synthesis of Intermediate (20)

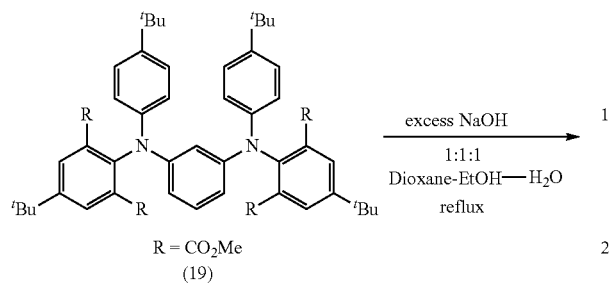

Intermediate (20) was obtained in the same manner as in Synthesis Example 3, except that Intermediate (19) was used instead of Intermediate (13) (yield 100%).

Synthesis Example 8: Synthesis of Compound 21 and Compound 22

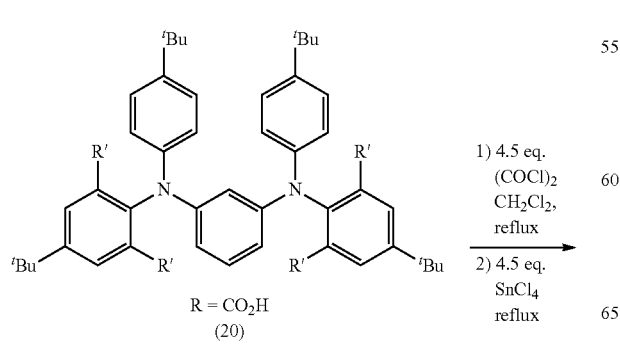

-continued

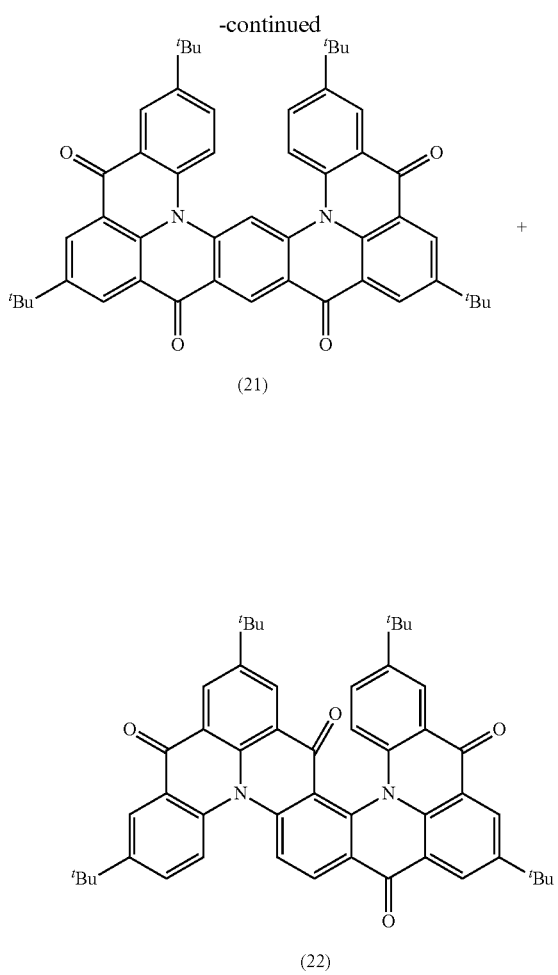

Compound 21 and Compound 22 were obtained in the same manner as in Synthesis Example 4, except that Intermediate (20) was used instead of Intermediate (14).

Compound 21: yield 30%, LC-MS: 741 (M+H+)

Compound 22: yield 36%, LC-MS: 741 (M+H+).

Example 3

Synthesis Example 9: Synthesis of Intermediate (23)

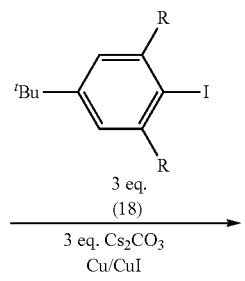

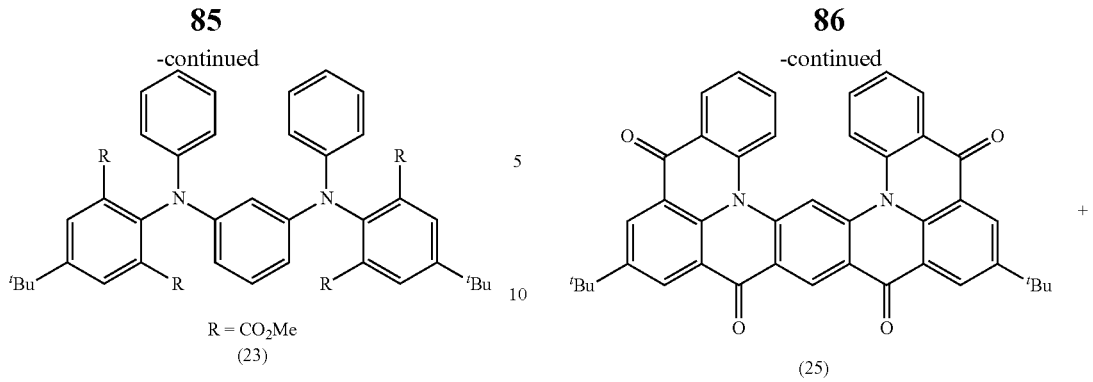

Intermediate (23) was obtained in the same manner as in Synthesis Example 2, except that Compound (18) was used instead of Compound (12) (yield 62%).

Synthesis Example 10: Synthesis of Intermediate (24)

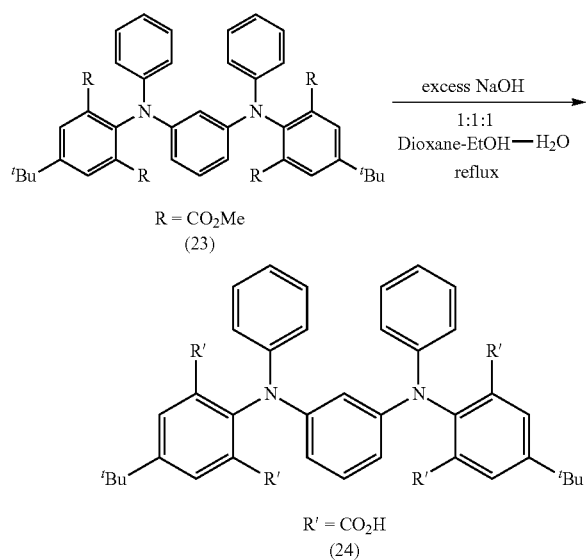

Intermediate (24) was obtained in the same manner as in Synthesis Example 3, except that Intermediate (23) was used instead of Intermediate (13) (yield 100%).

Synthesis Example 11: Synthesis of Compound 25 and Compound 26

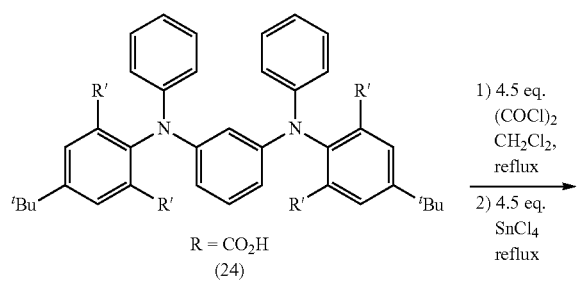

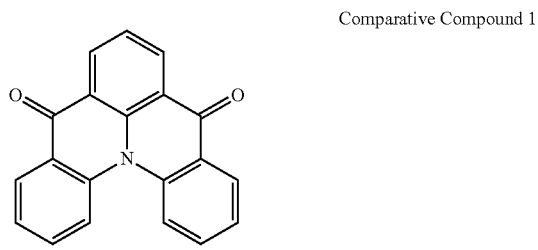 [SMILES: O=c1c2ccccc2n2c3ccccc3c(=O)c3cccc1c32]

Compound 25 and Compound 26 were obtained in the same manner as in Synthesis Example 4, except that Intermediate (24) was used instead of Compound (14):
Compound 25: yield 20%, LC-MS: 629 (M+H+)
Compound 26: yield 33%, LC-MS: 629 (M+H+).

Comparative Example 1: Preparation Comparative Compound 1

Quinolino[3,2,1-de]acridine-5.9-dione represented by the following Formula was prepared as Comparative Compound 1.

Evaluation Example 1: Measurement of HOMO Level and LUMO Level

The Compounds and Comparative Compound obtained above were each prepared as sample solids. Next, the HOMO and LUMO levels were measured as follows.
1. Preparation of Measurement Sample
(1) A sample solution was prepared such that a sample solid was 4 parts by weight based on 100 parts by weight of methyl benzoate as a solvent.
(2) The sample solution prepared in Section (1) was coated on each of an ITO substrate and a quartz substrate by a spin-coating method to form a coating film having a dry film thickness of 50 nm. The resulting coating film was heated under vacuum of $10^{-1}$ Pa or lower at 120° C. for 1 hour. Then, under vacuum of $10^{-1}$ Pa or lower, the coating film was cooled to room temperature to form a thin film layer (thin film sample).

2. Measurement of HOMO Level

The HOMO level of each compound was measured using the thin film sample on the ITO substrate prepared in Section 1.(2) by a photoelectron spectrometer AC-3 (available from Rikoki Co., Ltd.).

3. Measurement of LUMO Level

An energy gap value (Eg) at an absorption end of ultraviolet visible absorption spectrum was measured using the thin film sample on the quartz substrate prepared in Section 1.(2) by a spectrophotometer U-3900 (available from Hitachi High-Technologies), and the LUMO level was calculated by Equation A. The calculation results are shown in Table 1.

$$\text{LUMO=HOMO+Eg} \qquad \text{Equation A}$$

Evaluation Example 2: Measurement of Photoluminescence (PL) of Solution

The resulting Compounds and the Comparative Compound were each dissolved in toluene to prepare a $1 \times 10^{-5}$ M solution. This solution was filled in a 1 cm square four-sided transmission cell, and PL measurement was performed at room temperature using a spectrofluorometer F7000 (available from Hitachi High-Technologies Corporation). A peak wavelength, a FWHM, and a Stokes shift were computed from the obtained emission spectrum. The results of evaluation are shown in Table 1.

Evaluation Example 3: Measurement of S1 Value, T1 Value, and $\Delta E_{ST}$ Value 1. Preparation of Measurement Samples (1) The resulting Compounds and the Comparative Compound (sample solids) and polymethyl methacrylate (PMMA) were dissolved in toluene, followed by mixing PMMA and sample solids at a weight ratio of 99.5:0.5, to prepare 5 wt % of a toluene solution.

(2) The sample solutions prepared in Section (1) was spin-coated by using a spin coater MS-B100 (Mikasa Corporation) on an ITO substrate and a quartz substrate to form a spin-coating film having a dried film thickness of 500 nm. Subsequently, by 1 hour of heating at a temperature of 120° C., a thin film sample was prepared.

2. Measurement of S1 Value, T1 Value, and $\Delta E_{ST}$ Value

A fluorescence spectrum and a phosphorescence spectrum were measured using the thin film sample on the quartz substrate prepared in Section 1.(2) by a spectrophotometer (available from Hitachi High-Tech Co., Ltd.) at 77 Kelvin (K)., Ltd. The singlet energy S1 was calculated from the obtained fluorescence spectrum, and the triplet energy T1 was calculated from the phosphorescence spectrum. $\Delta E_{ST}$ was obtained according to Equation B. The results of evaluation are shown in Table 1.

$$\Delta E_{ST}=S1-T1 \qquad \text{Equation B}$$

Evaluation Example 4: Measurement of PLQY

The compounds shown in Table 1 were vacuum-deposited on a quartz substrate at a weight ratio of 1 wt % with respect to the host compound mCP at a vacuum pressure of $10^{-5}$ Pa to prepare a thin film having a thickness of 50 nm. The emission spectrum of each of the prepared thin film was measured by using Quantaurus-QY Absolute PL quantum yield (PLQY) measurement system C11347-01 (Hamamatsu Photonics Co., Ltd) to measure PLQY. In the measurement, the excitation wavelength was scanned at intervals of 10 nm from 300 nm to 400 nm, and the excitation wavelength region in which the compound absorption value showed 10% or more of the excitation light intensity ratio was adopted. The value of PLQY was taken as the highest value in the adopted excitation wavelength region. The results of evaluation are shown in Table 1.

TABLE 1

| | Compound No. | HOMO (eV) | LUMO (eV) | Emission peak wavelength (nm) | FWHM (nm) | Stokes shift (nm) | S1 (eV) | T1 (eV) | $\Delta E_{ST}$ (eV) | PLQY |
|---|---|---|---|---|---|---|---|---|---|---|
| Example 1 | Compound 15 | −6.40 | −3.67 | 448 | 27 | 18 | 2.82 | 2.65 | 0.18 | 56 |
| Example 2 | Compound 21 | −6.40 | −3.74 | 452 | 20 | 10 | 2.81 | 2.58 | 0.23 | 86 |
| Example 3 | Compound 25 | −6.30 | −3.58 | 446 | 18 | 10 | 2.84 | 2.61 | 0.23 | 90 |
| Comparative Example 1 | Comparative Compound 1 | −6.30 | −3.59 | 454 | 31 | 22 | 2.76 | 2.57 | 0.18 | 37 |

Example 4: Manufacture of Organic Light-Emitting Device

Polymer P-1 represented by the following Formula was synthesized according to the preparation of Compound T 5 described in WO 2011/159872. The number average molecular weight (Mn) of P-1 measured by gel permeation chromatography (GPC) was 141,000, and the weight average molecular weight (Mw) was 511,000.

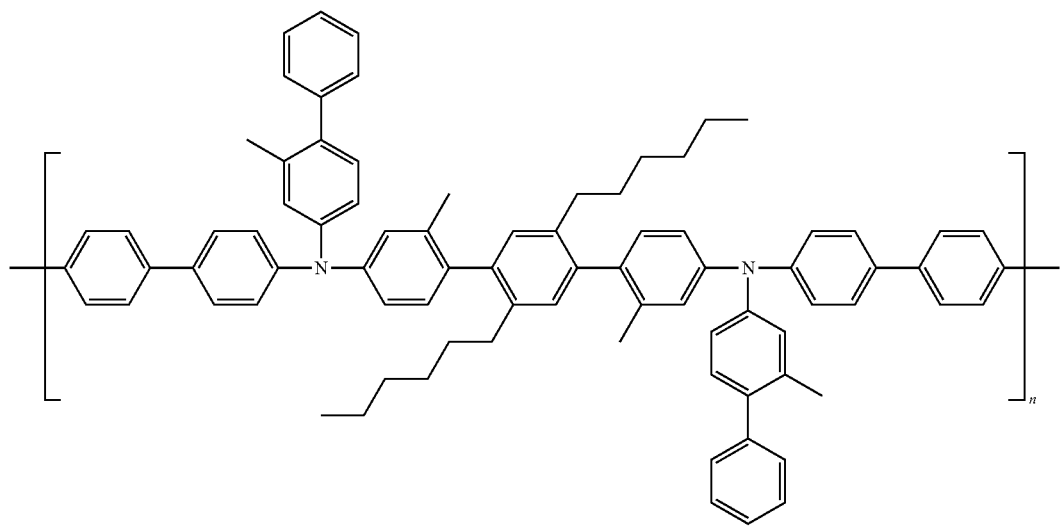

P-1

In addition, FA-14 (see Formula below) was synthesized using the method described in the specification of US 2016/0315259, herein incorporated by reference.

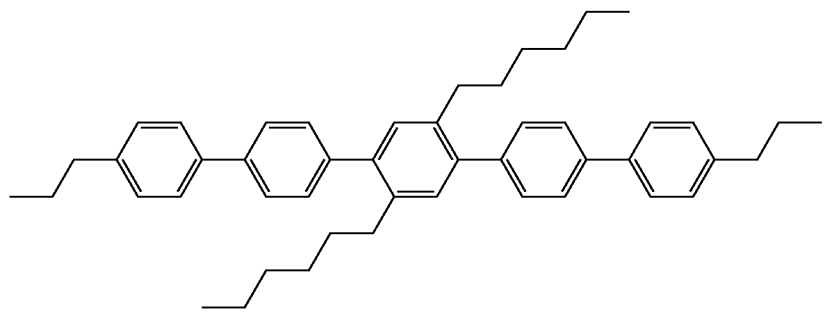

FA-14

As a first electrode (anode), a glass substrate on which indium tin oxide (ITO) in the form of a stripe was deposited to a film thickness of 150 nm was prepared. Poly(3,4-ethylenedioxythiophene)/poly(4-styrene sulfonate) (PEDOT/PSS) (available from Sigma-Aldrich) was applied by spin-coating on this glass substrate to a dry film thickness of 30 nm, thereby forming a hole injection layer.

Next, a hole transport layer coating solution was prepared by dissolving P-1 and FA-14 in anisole as a solvent. The hole transport layer coating solution was prepared such that an amount of P-1 was 80% by weight based on the total weight of the hole transport layer, and an amount of FA-14 was 20% by weight based on the total weight of the hole transport layer. Subsequently, the resulting hole transport layer coating solution was coated on the hole injection layer by a spin-coating method to form a coating film such that a thickness of the dry film was 125 nm. The resulting coating film was heated under vacuum of $10^{-1}$ Pa or lower at 230° C. for 1 hour. Then, under a vacuum pressure of $10^{-1}$ Pa or lower, the coating film was cooled to room temperature to form a hole transport layer.

Next, mCP as a host material and Compound 15 as a dopant material were co-deposited at a weight ratio of 98.5:1.5 on the hole transport layer to form an emission layer having a thickness of 55 nm.

Then, Liq and KLET-03 (Chemipro Kasei Kaisha Ltd) were co-deposited at a mass ratio of 2:8 on the emission layer to form an electron transport layer having a thickness of 20 nm.

Liq was deposited on the electron transport layer using a vacuum deposition apparatus to form an electron injection layer having a thickness of 3.5 nm.

Subsequently, aluminum was deposited on the electron injection layer using a vacuum deposition apparatus to form a second electrode (cathode) having a thickness of 100 nm.
Evaluation of Organic Light-Emitting Device Emission peak wavelength, FWHM, and Max external quantum efficiency (EQE) were evaluated according to the following method. The organic light-emitting device was allowed to emit light by continuously changing the voltage applied to the organic light-emitting device using a DC constant voltage power supply (2400 source meter from KEITHLEY), and the brightness and emission spectrum at this time were measured with a luminance meter (a multichannel spectrometer PMA12 available from Hamamatsu Photonics. Co., Ltd.). In addition, the current value and the EQE (%) were calculated from the measurement results. In addition, the wavelength showing the maximum value in the EQE graph for the wavelength was defined as the emission peak wavelength (nm), and the wavelength width corresponding to a half of the emission peak wavelength (nm) was defined as the FWHM (nm). In addition, the Max EQE shown here is an EQE value at a current density of 0.1 (mA/m²) calculated from the area of the organic light-emitting device, while driving. However, EQE (relative value) in Table 2 is shown as a relative value relative to the value of Comparative Example 2 of 100.

Examples 5 and 6 and Comparative Example 2

Organic light-emitting devices were manufactured in the same manner as in Example 4, except that Compound 15 was changed with compounds shown in Table 2 in formation of the emission layer. Evaluation was performed on the organic light-emitting devices. The results of evaluation are shown in Table 2.

TABLE 2

| | Emission layer | | Emission peak wavelength (nm) | FWHM (nm) | EQE (relative value) |
|---|---|---|---|---|---|
| | Host material | Dopant material | | | |
| Example 4 | mCP | Compound 15 | 457 | 38 | 150 |
| Example 5 | mCP | Compound 21 | 461 | 32 | 210 |
| Example 6 | mCP | Compound 25 | 454 | 29 | 220 |
| Comparative Example 2 | mCP | Comparative Compound 1 | 470 | 37 | 100 |

Referring to the results of Table 1, the heterocyclic compound according to embodiments was found to have a narrow emission spectrum having a peak wavelength of a blue wavelength region and to emit blue light with a high colorimetric purity. In addition, the heterocyclic compound according to embodiments was found to have a narrow $\Delta E_{ST}$ and exhibit high efficiency in emission.

Referring to the results of Table 2, the organic light-emitting device including the heterocyclic compound according to embodiments was found to have a narrow emission spectrum having a peak wavelength of a blue wavelength region and to emit blue light with a high colorimetric purity.

In addition, as shown in Table 2, in the organic light-emitting devices using the Compounds belonging to the scope of the present disclosure of Examples 4 to 6, the EQE was improved by 1.5 fold, and the luminescence efficiency was remarkably excellent, as compared with the organic light-emitting device using Comparative Compound 1, which may not belong to the scope of the present disclosure.

As apparent from the foregoing description, an organic light-emitting device including the heterocyclic compound may have improved efficiency and/or colorimetric purity.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by one of Formulae 1-11, 1-13, 1-21, 1-23, 1-31, or 1-41:

Formula 1-11
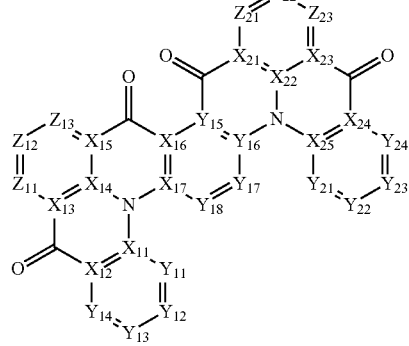

Formula 1-13
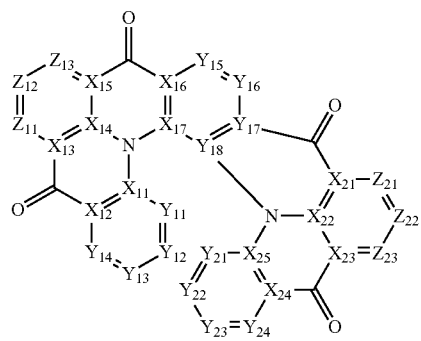

Formula 1-21
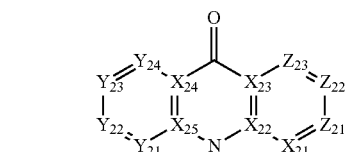
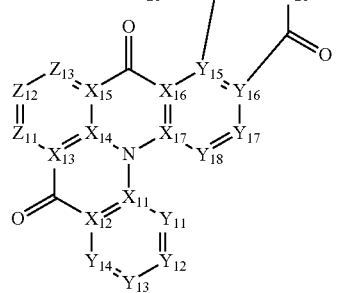

Formula 1-23
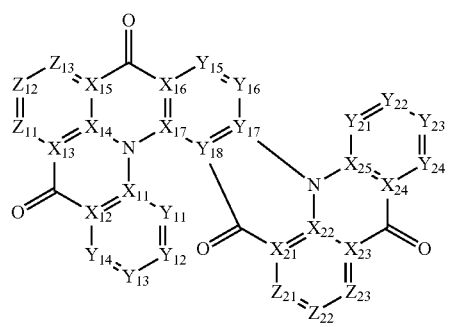

Formula 1-31
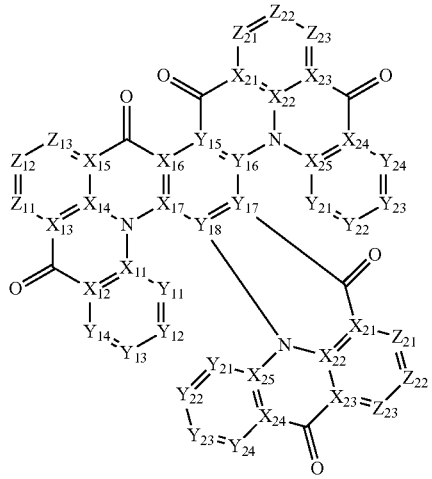

Formula 1-41
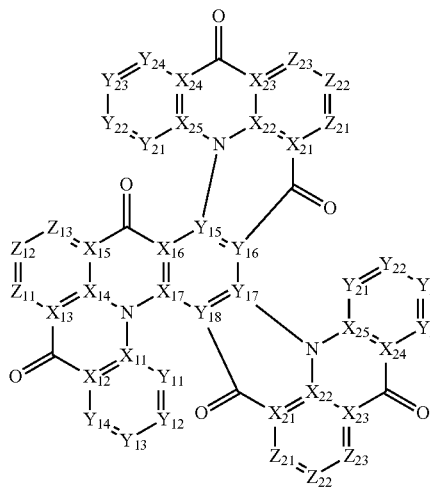

wherein, in Formulae 1-11, 1-13, 1-21, 1-23, 1-31, and 1-41, $X_{11}$ to $X_{17}$ and $X_{21}$ to $X_{25}$ are each independently a carbon atom, a bond between $X_{11}$ and $X_{12}$, a bond between $X_{13}$ and $X_{14}$, a bond between $X_{14}$ and $X_{15}$, a bond between $X_{16}$ and $X_{17}$, a bond between $X_{21}$ and $X_{22}$, a bond between $X_{22}$ and $X_{23}$, and a bond between $X_{24}$ and $X_{25}$ are each independently a single bond or a double bond, $Y_{11}$ is $C(R_{101})$ or N, $Y_{12}$ is $C(R_{102})$ or N, $Y_{13}$ is $C(R_{103})$ or N, $Y_{14}$ is $C(R_{104})$ or N, $Y_{15}$ is $C(R_{105})$ or N, $Y_{16}$ is $C(R_{106})$ or N, $Y_{17}$ is $C(R_{107})$ or N, $Y_{18}$ is $C(R_{108})$ or N, $Z_{11}$ is $C(R_{111})$ or N, $Z_{12}$ is $C(R_{112})$ or N, $Z_{13}$ is $C(R_{113})$ or N, $Y_{21}$ is $C(R_{201})$ or N, $Y_{22}$ is $C(R_{202})$ or N, $Y_{23}$ is $C(R_{203})$ or N, $Y_{24}$ is $C(R_{204})$ or N, $Z_{21}$ is $C(R_{211})$ or N, $Z_{22}$ is $C(R_{212})$ or N, and $Z_{23}$ is $C(R_{213})$ or N, and $R_{101}$ to $R_{108}$, $R_{111}$ to $R_{113}$, $R_{201}$ to $R_{204}$, and $R_{211}$ to $R_{21}$ are each a deuterium atom, a halogen atom, a substituted or unsubstituted alkyl group, a substituted or unsubstituted haloalkyl group, a substituted or unsubstituted alkoxy group, a substituted or unsubstituted alkylthio group, a substituted or unsubstituted aryl group, a substituted or unsubstituted heteroaryl group, a substituted or unsubstituted aryloxy group, a substituted or unsubstituted heteroaryloxy group, a substituted or unsubstituted arylthio group, a substituted or unsubstituted heteroarylthio group, or a substituted or unsubstituted amino group.

2. The heterocyclic compound of claim 1, wherein $R_{101}$ to $R_{108}$, $R_{111}$ to $R_{113}$, $R_{201}$ to $R_{204}$, and $R_{211}$ to $R_{21}$ are each independently a deuterium atom, a halogen atom, a linear or branched unsubstituted alkyl group having 1 or more and 20 or fewer carbon atoms, a substituted or unsubstituted cycloalkyl group having 3 or more and 10 or fewer carbon atoms, a linear or branched unsubstituted alkenyl group having 2 or more and 20 or fewer carbon atoms, a linear or branched unsubstituted alkynyl group having 2 or more and 20 or fewer carbon atoms, a substituted or unsubstituted cycloalkyl group having 3 or more and 10 or fewer carbon atoms, a substituted or unsubstituted alkyl cycloalkyl group having 4 or more and 10 or fewer carbon atoms, a substituted or unsubstituted cycloalkenyl group having 3 or more and 10 or fewer carbon atoms, a substituted or unsubstituted alkyl cycloalkenyl group having 4 or more and 10 or fewer carbon atoms, a substituted or unsubstituted heterocycloalkyl group having 2 or more and 10 or fewer carbon atoms, a substituted or unsubstituted alkyl heterocycloalkyl group having 3 or more and 10 or fewer carbon atoms, a linear or branched unsubstituted haloalkyl group having 1 or more and 20 or fewer carbon atoms, a substituted or unsubstituted halocycloalkyl group having 3 or more and 10 or fewer carbon atoms, a linear or branched unsubstituted alkoxy group having 1 or more and 20 or fewer carbon atoms, a substituted or unsubstituted cycloalkoxy group having 3 or more and 10 or fewer carbon atoms, a substituted or unsubstituted cycloalkylthio group having 3 or more and 10 or fewer carbon atoms, a substituted or unsubstituted aryl group having 6 or more and 30 or fewer carbon atoms, a substituted or unsubstituted alkyl aryl group having 6 or more and 30 or fewer carbon atoms, a substituted or unsubstituted aryloxy group having 6 or more and 30 or fewer carbon atoms, a substituted or unsubstituted arylthio group having 6 or more and 30 or fewer carbon atoms, a substituted or unsubstituted heteroaryl group having 3 or more and 30 or fewer carbon atoms, a substituted or unsubstituted alkyl heteroaryl group having 3 or more and 30 or fewer carbon atoms, a substituted or unsubstituted heteroaryloxy group having 3 or more and 30 or fewer carbon atoms, a substituted or unsubstituted heteroarylthio group having 3 or more and 30 or fewer carbon atoms, or a bisubstituted amino group represented by —NRR', and R and R' are each independently a monovalent group derived from an aromatic hydrocarbon ring having 6 or more and 30 or fewer ring-forming atoms or a monovalent group derived from a heteroaromatic ring having 5 or more and 30 or fewer ring-forming atoms.

3. The heterocyclic compound of claim 1, wherein $R_{101}$ to $R_{108}$, $R_{111}$ to $R_{113}$, $R_{201}$ to $R_{204}$, and $R_{211}$ to $R_{21}$ are each independently a deuterium atom, —F, —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen atom is substituted with a deuterium atom, a group represented by one of Formulae 9-1 to 9-39 in which at least one hydrogen atom is substituted with —F, a group represented by one of Formulae 10-12 to 10-130, a group represented by one of Formulae 10-12 to 10-130 in which at least one hydrogen atom is substituted with a deuterium atom, a group represented by one of Formulae 10-12 to 10-130 in which at least one hydrogen atom is substituted with —F, a group represented by one of Formulae 10-359 to 10-380, a group represented by one of Formulae 10-359 to 10-380 in which at least one hydrogen atom is substituted with a deuterium atom, a group represented by one of Formulae 10-359 to 10-380 in which at least one hydrogen atom is substituted with —F:

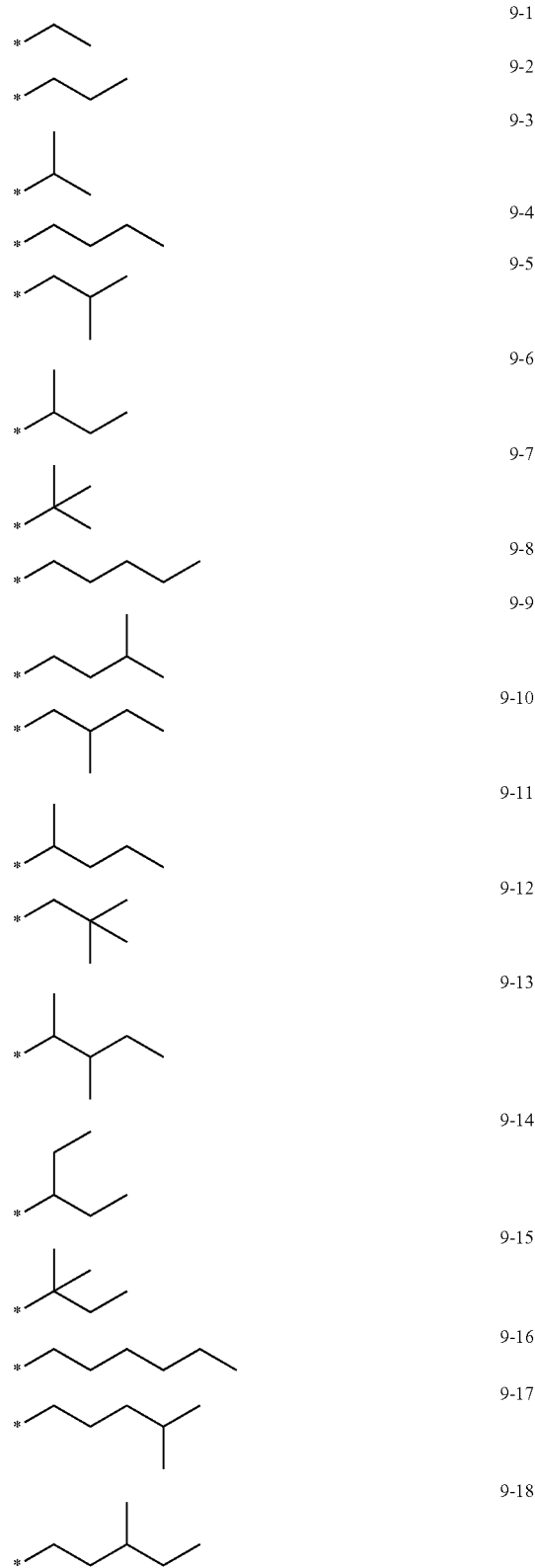

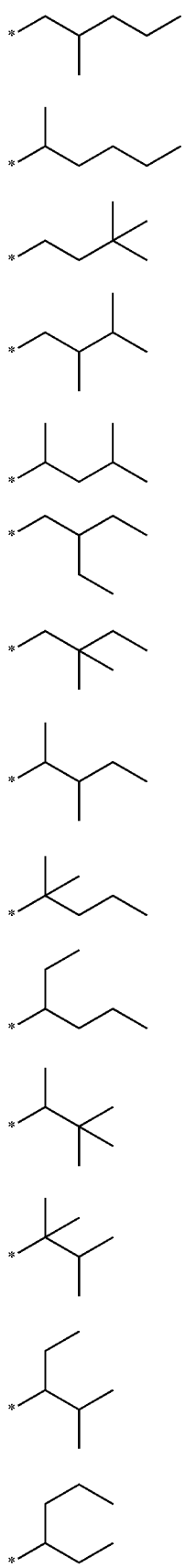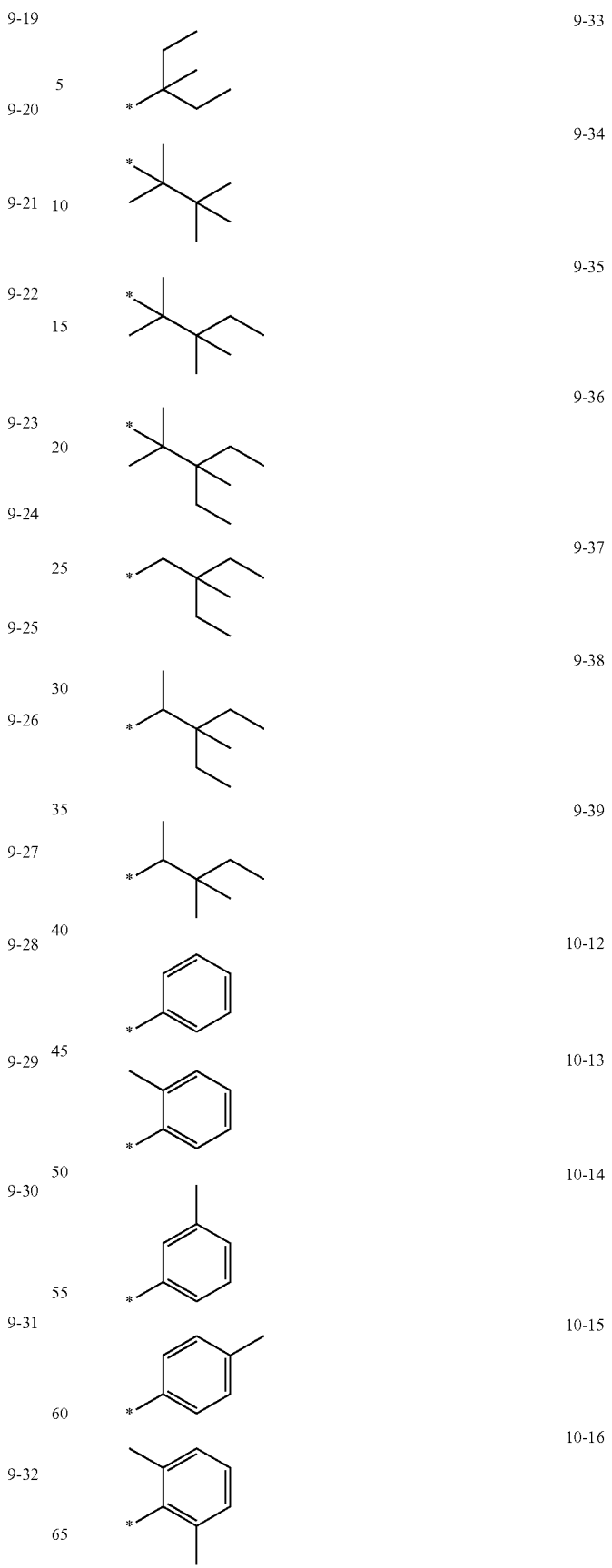

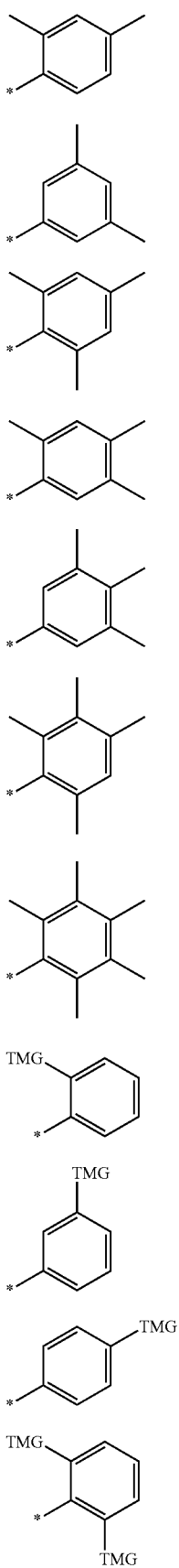
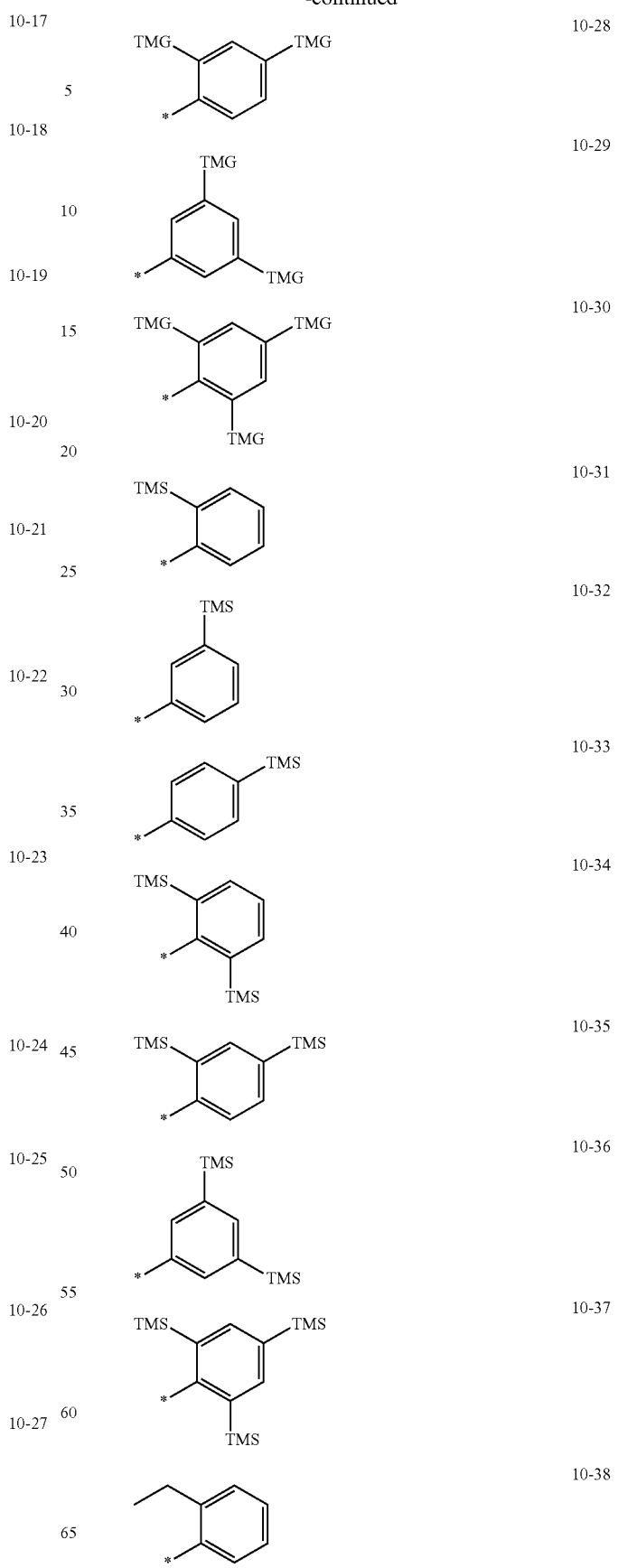

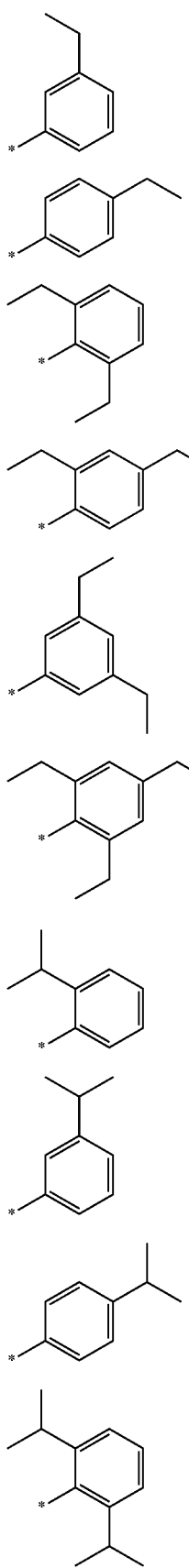
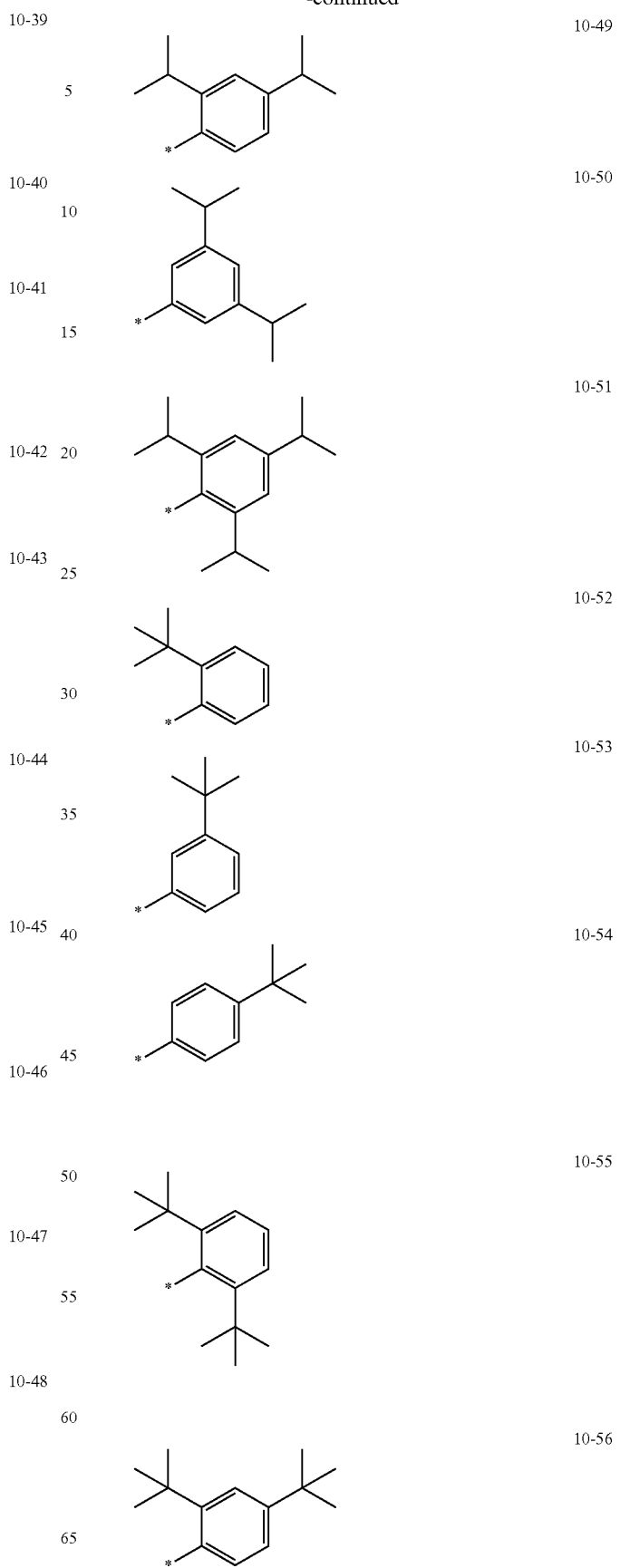

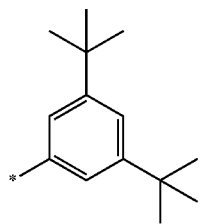
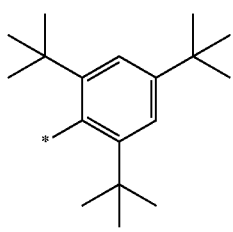
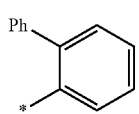
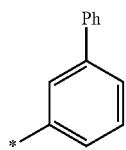
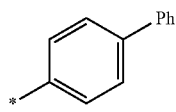
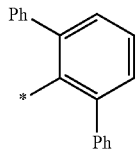
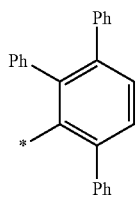
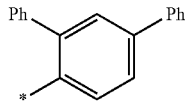
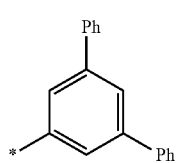
10-57
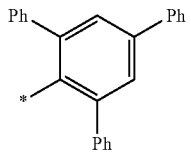
10-58
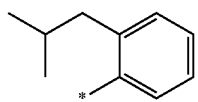
10-59
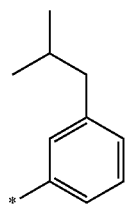
10-60
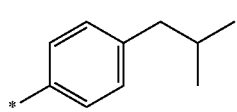
10-61
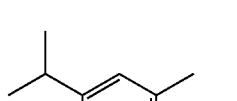
10-62
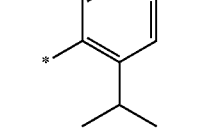
10-63
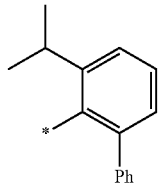
10-64
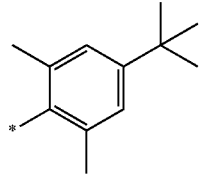
10-65
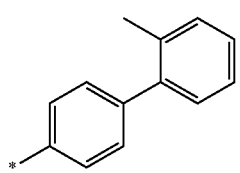
10-66
10-67
10-68
10-69
10-70
10-71
10-72
10-73
10-74
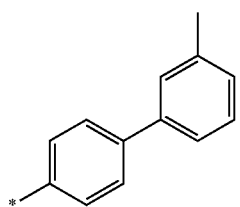

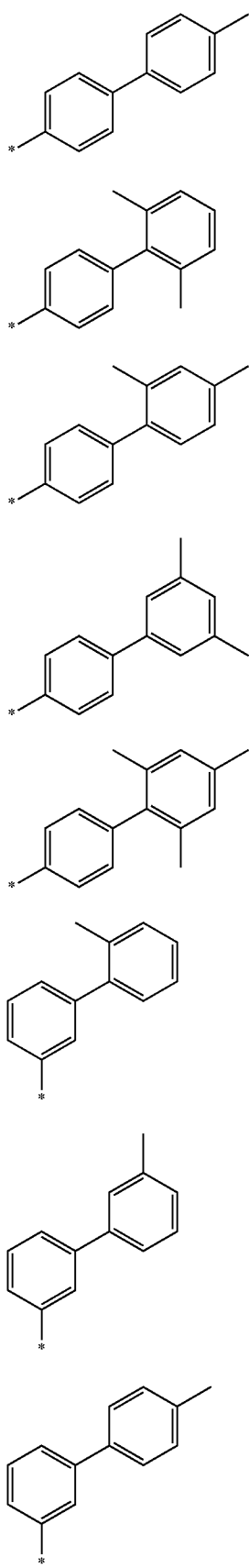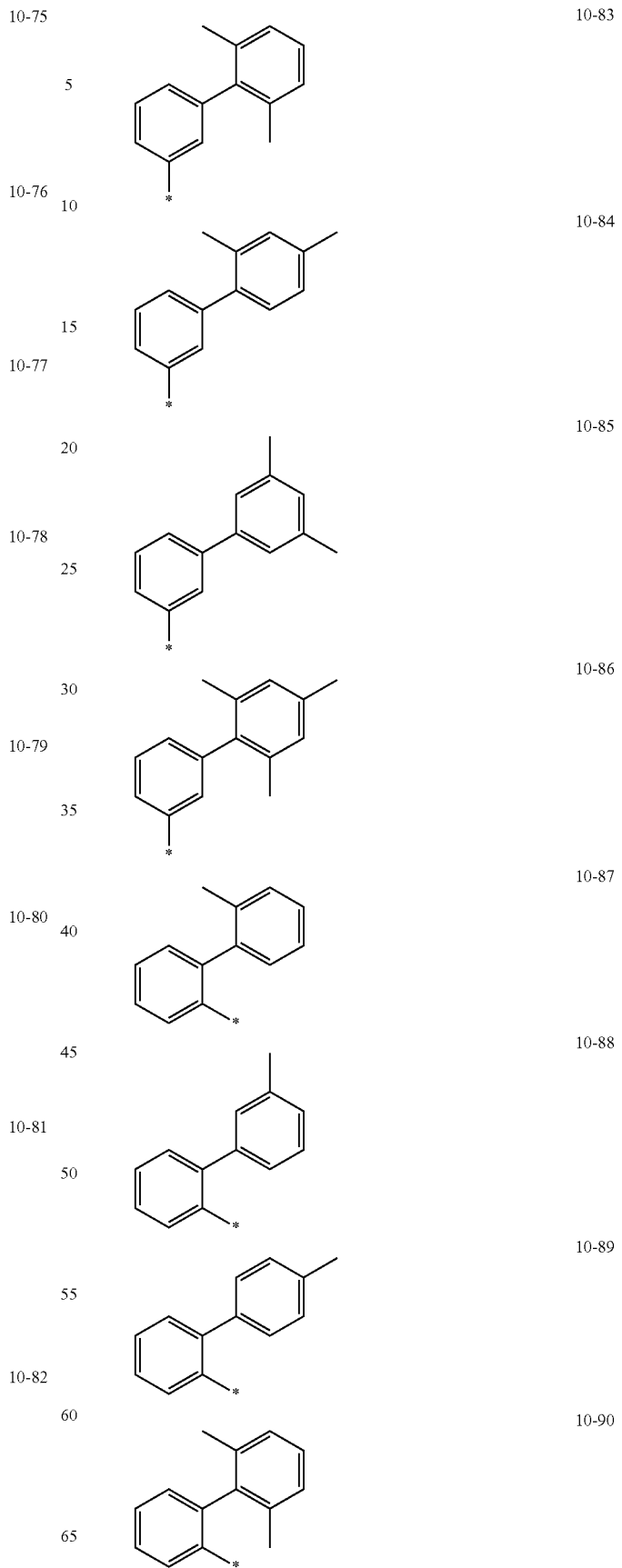

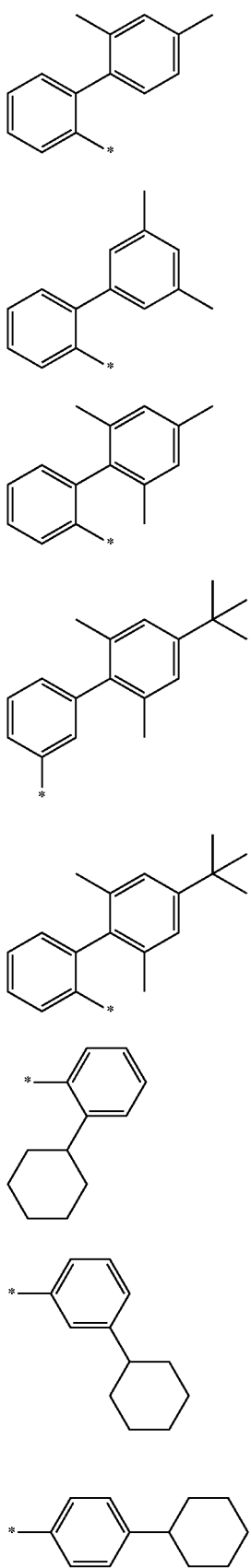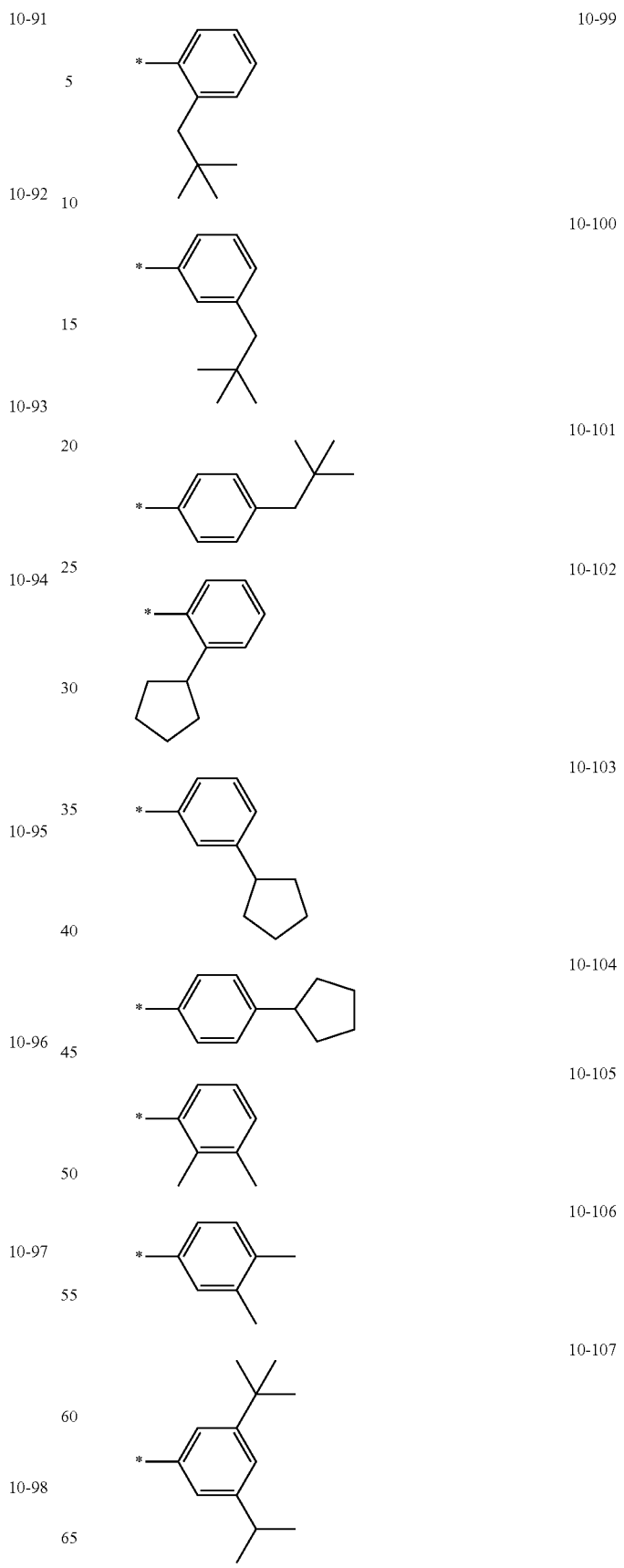

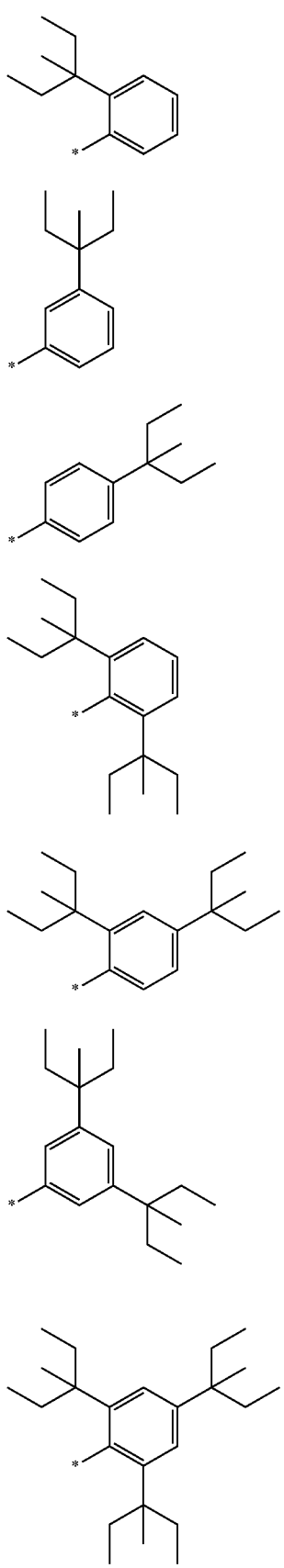
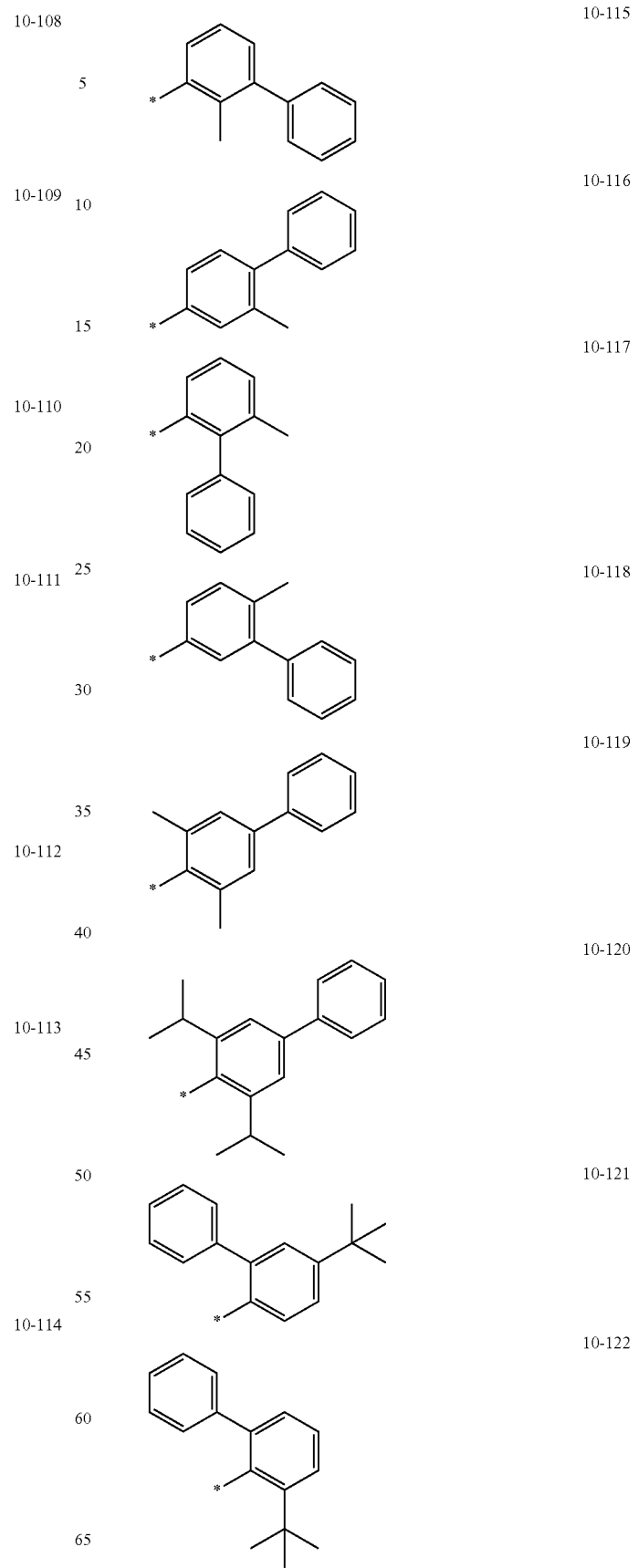

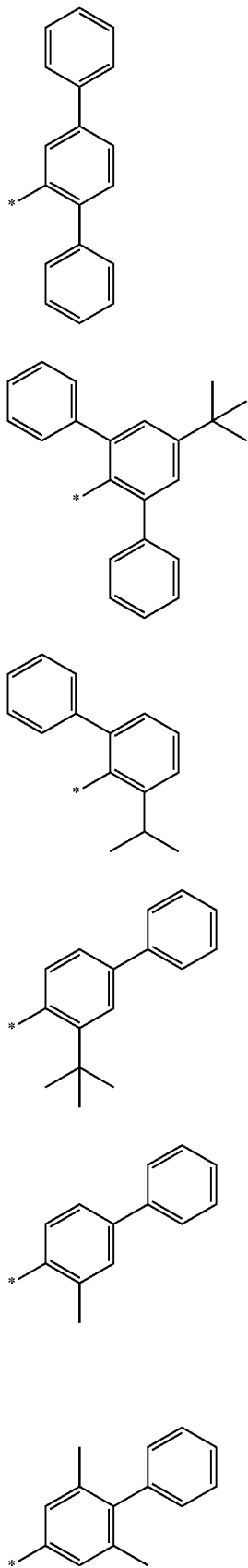
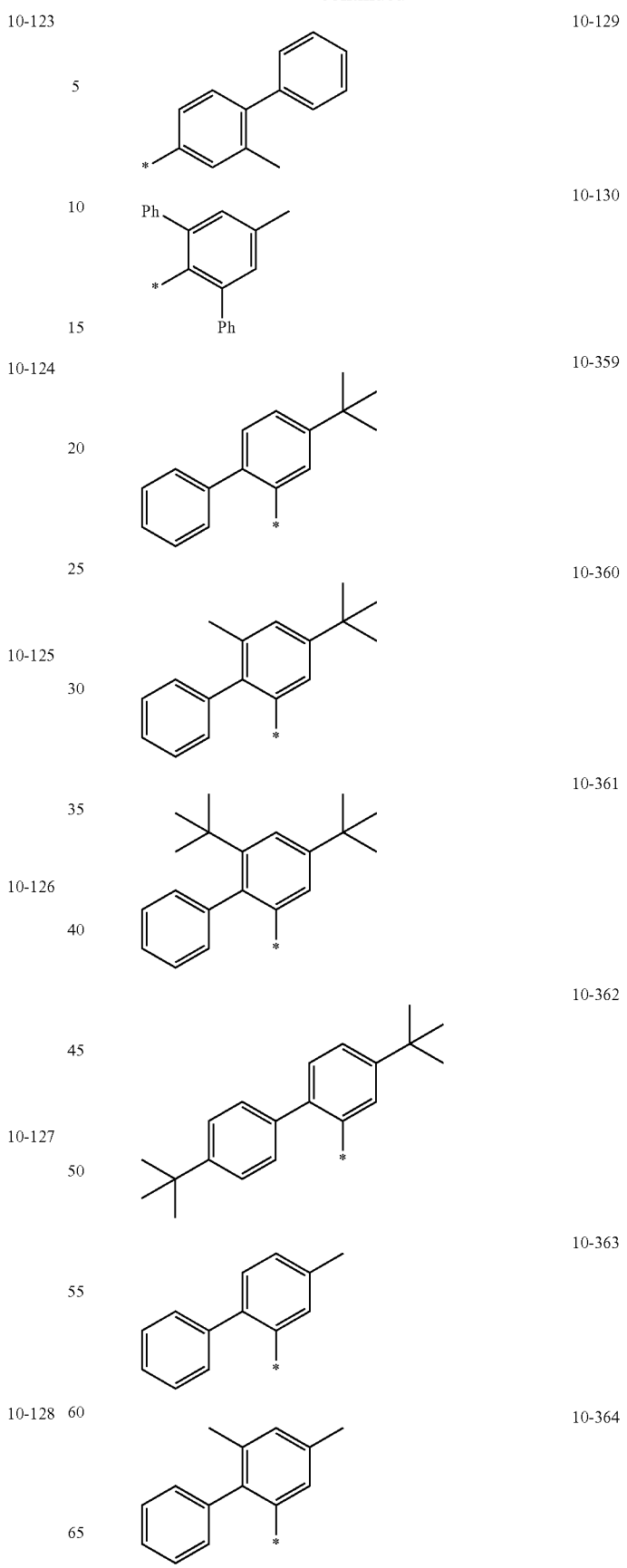

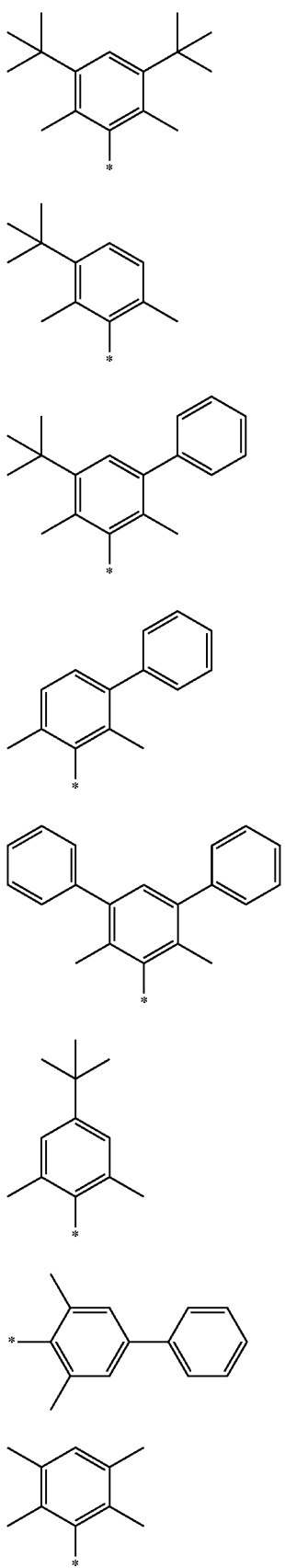
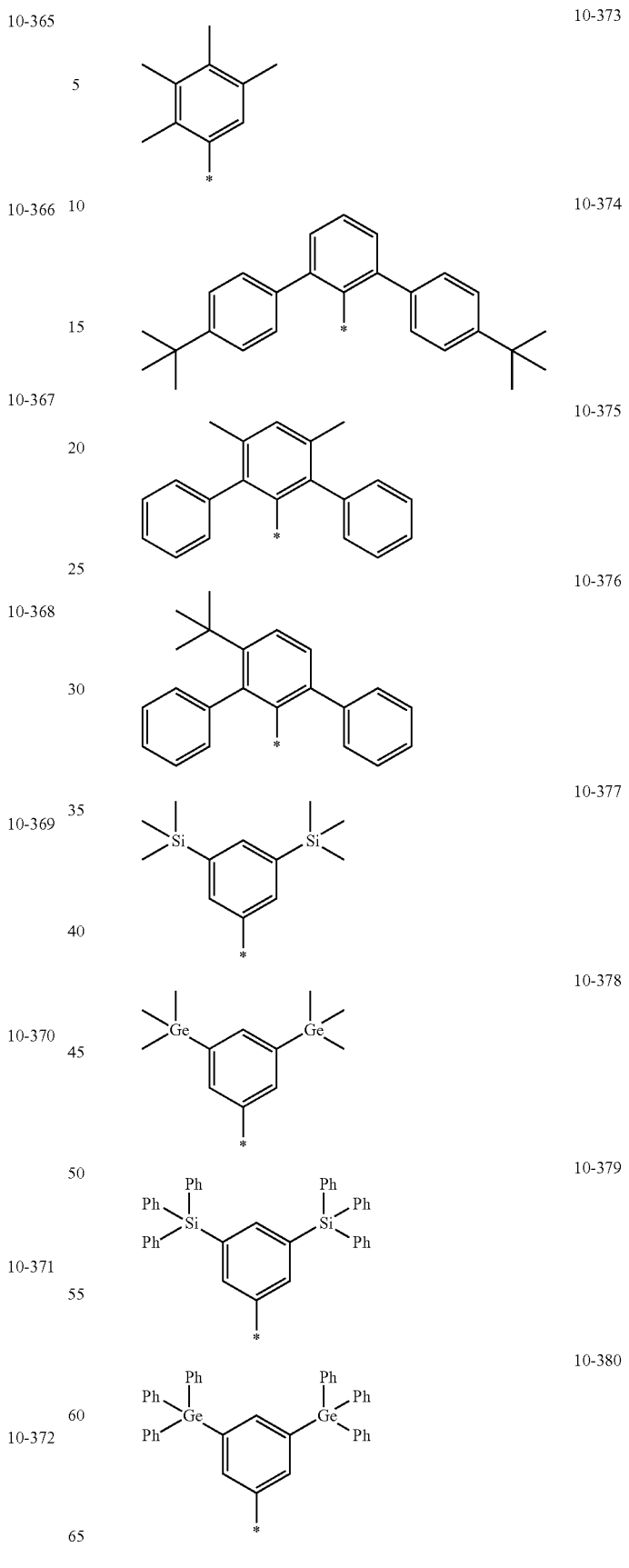

wherein, in Formulae 9-1 to 9-39, 10-12 to 10-130, and 10-359 to 10-380,

* indicates a binding site to an adjacent atom, "Ph" represents a phenyl group, "TMS" and "SiMe$_3$" each represent a trimethylsilyl group, and "TMG" and "GeMe$_3$" each represent a trimethylgermyl group.

4. The heterocyclic compound of claim 1, wherein the heterocyclic compound represented by Formula 1 and Formula 2 is selected from Compounds 4, 8, 11, or 23 to 27:

4
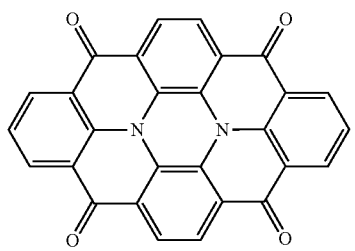

8
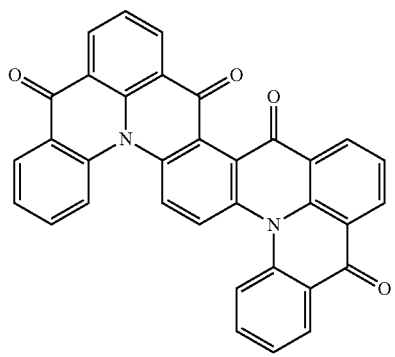

11
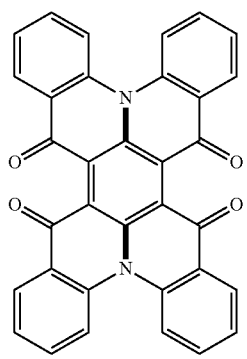

23
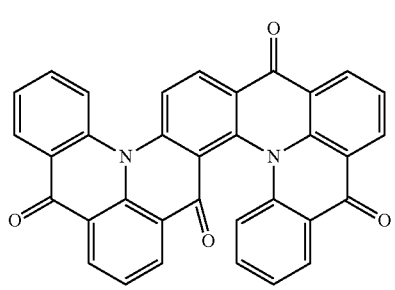

24
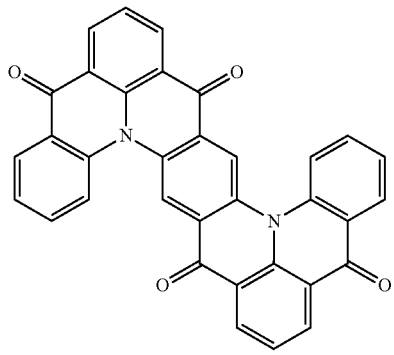

25

26

-continued

27

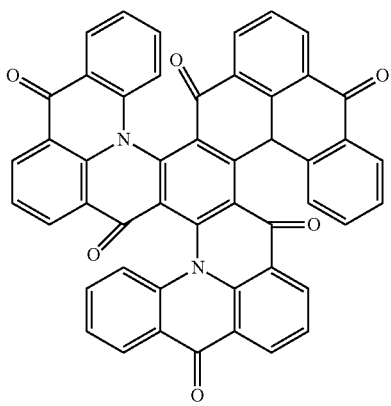

wherein, "Ph" in Compounds 16 and 17 represents an unsubstituted phenyl group.

5. The heterocyclic compound of claim 1, wherein the heterocyclic compound satisfy Conditions 1 to 4:

$\Delta E_{ST} > \Delta E_{ST2} + \Delta E'_{TT}$  Condition 1

$0\ eV < \Delta E_{ST2} + \Delta E'_{TT} \leq 1.0\ eV$  Condition 2

$0\ eV < \Delta E'_{TT} \leq 0.15\ eV$  Condition 3

$\Delta E_{ST2} > 0\ eV$  Condition 4 wherein, in Conditions 1 to 4, $\Delta E_{ST}$ indicates a difference between a lowest excited singlet energy level calculated in an $S_1$ equilibrium structure of the heterocyclic compound and a lowest excited triplet energy level calculated in a $T_1$ equilibrium structure of the heterocyclic compound, $\Delta E_{ST2}$ indicates a difference between a lowest excited singlet energy level calculated in an $S_1$ equilibrium structure of the heterocyclic compound and a second lowest excited triplet energy level calculated in a $T_2$ equilibrium structure of the heterocyclic compound, and $\Delta E'_{TT}$ indicates a difference between a second lowest excited triplet energy level calculated in an $T_2$ equilibrium structure of the heterocyclic compound and a lowest excited triplet energy level calculated in a $T_2$ equilibrium structure of the heterocyclic compound.

6. The heterocyclic compound of claim 1, wherein the heterocyclic compound further satisfies Equation 5:

$\Delta E_{ST2} \leq 0.1\ eV$  Condition 5 wherein, in Condition 5, $\Delta E_{ST2}$ indicates a difference between a lowest excited singlet energy level calculated in an $S_1$ equilibrium structure of the heterocyclic compound and a second lowest excited triplet energy level calculated in a $T_2$ equilibrium structure of the heterocyclic compound.

7. An organic light-emitting device comprising: a first electrode; a second electrode; and an organic layer between the first electrode and the second electrode and comprising an emission layer, wherein the organic light-emitting device comprises the heterocyclic compound of claim 1.

8. The organic light-emitting device of claim 4, wherein the emission layer comprises the heterocyclic compound.

9. The organic light-emitting device of claim 8, wherein the emission layer further comprises a host, the host and the heterocyclic compound are different from each other, and the emission layer consists of the host and the heterocyclic compound.

10. The organic light-emitting device of claim 9, wherein the host does not emit light, and the heterocyclic compound emits light.

11. The organic light-emitting device of claim 8, wherein the emission layer further comprises a host and a dopant, the host, the dopant, and the heterocyclic compound are different from each other, and the emission layer consists of the host, the dopant, and the heterocyclic compound.

12. The organic light-emitting device of claim 11, wherein the host and the heterocyclic compound each do not emit light, and the dopant emits light.

13. An electronic apparatus comprising the organic light-emitting device of claim 7.

* * * * *